US012428474B2

(12) United States Patent
Charpentier et al.

(10) Patent No.: US 12,428,474 B2
(45) Date of Patent: *Sep. 30, 2025

(54) ANTIBODIES COMPRISING A COMMON LIGHT CHAIN AND USES THEREOF

(71) Applicant: Integral Molecular, Inc., Philadelphia, PA (US)

(72) Inventors: Thomas Charpentier, Philadelphia, PA (US); Ross Stewart Chambers, Philadelphia, PA (US); Lewis J. Stafford, Philadelphia, PA (US); Trevor Barnes, Philadelphia, PA (US); Jonathan T. Sullivan, Philadelphia, PA (US)

(73) Assignee: Integral Molecular, Inc., Philadelphia, PA (US)

( * ) Notice: Subject to any disclaimer, the term of this patent is extended or adjusted under 35 U.S.C. 154(b) by 708 days.

This patent is subject to a terminal disclaimer.

(21) Appl. No.: 17/649,889

(22) Filed: Feb. 3, 2022

(65) Prior Publication Data

US 2022/0372121 A1    Nov. 24, 2022

Related U.S. Application Data

(63) Continuation of application No. 16/789,626, filed on Feb. 13, 2020, now Pat. No. 11,254,736.

(60) Provisional application No. 62/806,052, filed on Feb. 15, 2019.

(51) Int. Cl.
   *C07K 16/18* (2006.01)
   *A61K 38/00* (2006.01)

(52) U.S. Cl.
   CPC .............. *C07K 16/18* (2013.01); *A61K 38/00* (2013.01); *C07K 2317/24* (2013.01); *C07K 2317/565* (2013.01); *C07K 2317/622* (2013.01)

(58) Field of Classification Search
   CPC ................ C07K 16/18; C07K 2317/24; C07K 2317/565; C07K 2317/622; C07K 16/2803; C07K 16/2818; C07K 16/2896; C07K 16/32; C07K 16/28; C07K 2317/515; A61K 38/00
   See application file for complete search history.

(56) References Cited

U.S. PATENT DOCUMENTS

| | | |
|---|---|---|
| 4,376,110 A | 3/1983 | David et al. |
| 4,699,880 A | 10/1987 | Goldstein |
| 4,816,567 A | 3/1989 | Cabilly et al. |
| 4,946,778 A | 8/1990 | Ladner et al. |
| 5,260,203 A | 11/1993 | Ladner et al. |
| 5,475,096 A | 12/1995 | Gold et al. |
| 5,831,012 A | 11/1998 | Nilsson et al. |
| 6,004,746 A | 12/1999 | Brent et al. |
| 6,005,079 A | 12/1999 | Casterman et al. |
| 6,794,144 B1 | 9/2004 | Saksela et al. |
| 6,818,418 B1 | 11/2004 | Lipovsek et al. |
| 6,994,982 B1 | 2/2006 | Watt et al. |
| 7,105,653 B2 | 9/2006 | Shanafelt et al. |
| 7,166,697 B1 | 1/2007 | Galanis et al. |
| 7,186,524 B2 | 3/2007 | Kolmar et al. |
| 7,250,297 B1 | 7/2007 | Beste et al. |
| 7,417,130 B2 | 8/2008 | Stumpp et al. |
| 7,763,258 B2 | 7/2010 | Doms et al. |
| 7,803,907 B2 | 9/2010 | Stemmer et al. |
| 7,838,629 B2 | 11/2010 | Fiedler et al. |
| 8,158,130 B2 | 4/2012 | Doms et al. |
| 8,377,691 B2 | 2/2013 | Doranz |
| 9,074,002 B2 | 7/2015 | Tonks et al. |
| 9,428,567 B2 | 8/2016 | Garcia et al. |
| 9,580,486 B2 | 2/2017 | Gavin et al. |
| 9,616,106 B2 | 4/2017 | Basile |
| 10,336,818 B2 | 7/2019 | Chamberlain et al. |
| 11,254,736 B2 * | 2/2022 | Charpentier ....... C07K 16/2896 |
| 2004/0023334 A1 | 2/2004 | Prior |
| 2004/0132094 A1 | 7/2004 | Etzerodt et al. |
| 2004/0141980 A1 | 7/2004 | Ignjatovic et al. |
| 2004/0146938 A1 | 7/2004 | Nguyen et al. |
| 2004/0157209 A1 | 8/2004 | Mlmaz et al. |
| 2004/0209243 A1 | 10/2004 | Nixon et al. |
| 2005/0123563 A1 | 6/2005 | Doranz et al. |
| 2006/0269515 A1 | 11/2006 | Denis-Mize et al. |
| 2010/0119446 A1 | 5/2010 | Grabulovski et al. |
| 2010/0239633 A1 | 9/2010 | Strome et al. |
| 2012/0195882 A1 | 8/2012 | Doms et al. |
| 2012/0301476 A1 | 11/2012 | Okano et al. |
| 2014/0120092 A1 * | 5/2014 | Gros ...................... A61P 37/02 530/387.3 |

(Continued)

FOREIGN PATENT DOCUMENTS

| | | |
|---|---|---|
| CN | 102746397 A | 10/2012 |
| CN | 103483449 A | 1/2014 |

(Continued)

OTHER PUBLICATIONS

Almagro, "Identification of differences in the specificity-determining residues of antibodies that recognize antigens of differenct size: implications for the rational design of antibody repertoires", J. Mol. Reconit. (2004); 17:132-143.

Baert, et al., "Influence of Immunogenicity on the Long-Term Efficacy of Infliximab in Crohn's Disease", New Engl. J. Med. (2003) 348:601-608.

Better et al., "*Escherichia coli* Secretion of an Active Chimeric Antibody Fragment", Science (1988) 240 (4855, 1041-1043.

Bird, et al., "Single-Chain Antigen-Binding Proteins", Science, (1998) vol. 242, pp. 432-426.

Boulianne, et al., "Production of functional chimaeric mouse/human antibody", Nature (1984) 312:643 646.

Cabilly, et al., "Generation of antibody activity from immunoglobulin polypeptide chaings produced in *Escherichia coli*", (1984) Proc. Natl. Acad. Sci USA 81:3273-3277.

(Continued)

Primary Examiner — Joanne Hama
Assistant Examiner — Joshua T Sally
(74) Attorney, Agent, or Firm — Goodwin Procter LLP

(57) ABSTRACT

Peptides and uses thereof, such as a common light chain in an antibody, are provided.

9 Claims, No Drawings
Specification includes a Sequence Listing.

(56) References Cited

U.S. PATENT DOCUMENTS

| | | | |
|---|---|---|---|
| 2014/0127219 | A1 | 5/2014 | Sahin et al. |
| 2014/0286898 | A1 | 9/2014 | Gavin et al. |
| 2017/0003712 | A1 | 1/2017 | Funk et al. |
| 2017/0051029 | A1 | 2/2017 | Greve |
| 2017/0355756 | A1 | 12/2017 | Julien et al. |
| 2018/0044434 | A1 | 2/2018 | Sato et al. |
| 2020/0262898 | A1 | 8/2020 | Charpentier et al. |
| 2020/0262915 | A1 | 8/2020 | Chambers et al. |

FOREIGN PATENT DOCUMENTS

| | | | | |
|---|---|---|---|---|
| EA | 0171496 | | 2/1986 | |
| EP | 0125023 | A1 | 11/1984 | |
| EP | 0173494 | A2 | 3/1986 | |
| EP | 0184187 | A2 | 6/1986 | |
| EP | 0404097 | A2 | 12/1990 | |
| TW | 201125580 | A | 8/2011 | |
| WO | 1986001533 | | 3/1986 | |
| WO | 1987002671 | A1 | 5/1987 | |
| WO | 1988001649 | A1 | 3/1988 | |
| WO | 1993011161 | A1 | 6/1993 | |
| WO | 1994004678 | A1 | 3/1994 | |
| WO | 1994025591 | A1 | 11/1994 | |
| WO | 2008068048 | A2 | 6/2008 | |
| WO | 2009025759 | A1 | 2/2009 | |
| WO | 2010085495 | A1 | 7/2010 | |
| WO | WO-2010126590 | A1 * | 11/2010 | ............ C07K 16/40 |
| WO | 2014016737 | | 1/2014 | |
| WO | 2014153111 | A3 | 11/2014 | |
| WO | 2016025385 | A1 | 2/2016 | |
| WO | 2016014428 | A3 | 3/2016 | |
| WO | WO-2016164468 | A2 * | 10/2016 | ......... A61K 38/4886 |
| WO | 2016164937 | A3 | 1/2017 | |
| WO | 2017192567 | A1 | 11/2017 | |
| WO | 2018067198 | | 4/2018 | |
| WO | 2019031965 | A1 | 2/2019 | |

OTHER PUBLICATIONS

Chen, et al., "Enhancement and destruction of antibody function by somatic mutation: unequal occurrence if controlled by V gene combinatorial associates", The EMBO Journal (1995) vol. 14, No. 12, pp. 2784-2794.

Chothia, et al., "Canonical Structures for the Hypervariable Regions of Immunoglobulins", Mol. Biol. (1987) 196:901-917.

Extended Search Report issued in 20756721.5 dated Nov. 17, 2022.

Hodgson et al., "Making Monoclonals In Microbes", BioTechnology (1991) 9:421-425.

Holliger at al., "Engineered Antibody Fragments and the Rise of Single Domains", Nat. Biotechnol. (2005) 23:1126-1136.

Holliger et al. "Diabodies": Small bivalent and bispecific antibody fragments, Proc Natl. Acad. Sci. USA (1993) 90:6444-5448.

Juston et al., "Protein engineering of antibody binding sites Recovery of specific activity in an anti-digoxin single-chain Fv analogue produced in Escherichia coli", Proc. Nat. Acad. Sci. (1988) 85:5879-5883.

Koenig, et al., "Mutational landscape of antibody variable domains reveals a switch modulating the interdomain conformational dynamics and antigen binding", PNAS (2017) pp. E486-E495, www.pnas.org/cgi/doi/10.1073/pnas.1613231114.

Kohler, et al., "Continuous cultures of fused cells secreting antibody of predefined specificity", Nature (1975) vol. 256: pp. 495 497.

Kozbor, et al., "The production of monoclonal antibodies from human lymphocytes", Immunol. Today (1983) 4:72 79.

Kussie, et al., "A Single Engineered Amino Acid Substituion Changes Antibody Fine Specificity1", J immunol (1994) 152(1): pp. 146-152.

Lathe et al., "Synthetic oligonucleotide probes deduced from amino acid sequence data. Theroetical and practical considerations", J. Molec. Biol. (1985) 183:1-12.

Lefranc et al., "IMGT unique numbering for immunoglobulin and T cell receptor variable domains and Ig superfamily V-like domains" Developmental & Comparative Immunology (2003) 27:55-77.

Liu et al., "Production of a mouse-human chimeric monoclonal antibody to CD20 with potent Fc-dependent biologic activity", J. Immunolo. (1987) 139(10):3521-6.

Liu, et al., "Chimeric mouse-human IgG1 antibody that can mediate lysis of cancer cells", Proc. Nationl. Acad. Sci. (1987) 84:3439-3433.

Milgrom et al., "Treatment of Allergic Asthma with Monoclonal Anti-IgE Antibody", (1999) New Engl. J. Med. 341:1966-1973.

Morrison, et al., "Chimeric human antibody molecules: Mouse antigen-binding domains with humane constant region domains", (1984) Proc. Natl. Acad. Sci. USA 81:6851-6855.

Muller et al., "Determination of Affinity and Specificity of Anti-Hapten Antibodies by Competitive Radioimmunoassay", Meth. Enzymol. (1983) 92:589-601.

Neuberger, et al., "A hapten-specific chimaeric IgE antibody with human physiological effector function", Nature (1985) vol. 314 pp. 268-270.

Nishibori, et al., "Humanization of chicken monoclonal antibody using phage-display system", Molecular Immunology (2006) 43 pp. 634-642.

Non-final Office Action received in U.S. Appl. No. 16/789,626, mailed Mar. 30, 2021.

Queen, et al., "A humanized antibody that binds to the interleukin 2 receptor", Proc. Natil. Acad. Sci (1989), 86:10029-10032.

Reichmann et al., "Single domain antibodies: comparison of camel VH and camelised human VH domains", J. Immunol Method (1999) 231:25.

Riechmann, et al., "Reshaping human antibodies for therapy", Nature (1988) 332 (6162): vol. pp. 323-327.

Sahagan, et al., "A genetically engineered murine/human chimeric antibody retains specificity for human tumor-associated antigen.", J. Immunol. (1986) 137:pp. 1066-1074.

Slamon et al. "Use of Chemotherapy Plus a Monoclonal Antibody Against HER2 for Metastatic Breast Cancer that Overexpresses HER2", New Engl. J. Med. (2001) 344:783-792.

Storz et al., "Intellectual property protection Strategies for future antibody inventions", MAbs. (2011) 3(3): 310-317.

Sun, et al., "Chimeric antibody with human constant regions and mouse variable regions directed against carcinoma-associated antigen 7-1A", Proc. Natil. Acad. Sci. (1987) 84:214-218.

Tsurushita, et al., "Humanization of a chicken anti-IL-12 monoclonal antibody", Journal of Immunological methods, 2004) 295, pp. 9-19.

UniProtKB Accession No. A0A2V9M896_9BACT, Sialidase domain-containint protein, (2018).

Wahl et al., "Improved Radioimingin and Tumor Localizaton with Monoclonal F(ab')2", J. Nucl. Med. (1983) 24:316 325.

Ward, et al., "Binding activities of a repertoire of single immunoglobulin variable domains secreted from Escherichia coli", Nature (1989) vol. 341 pp. 544-546.

Wu et al., "An analysis of the sequences of the variable regions of bence jones proteins and myeloma light chains and their implications for anti-body complementarity", Journal of Experimental Medicine (1970) 132: pp. 211-250.

U.S. Appl. No. 16/789,626, filed Feb. 13, 2020, Thomas Charpentier, et al.

Krah S, et al., Generation of human bispecific common light chain antibodies by combining animal immunization and yeast display, Protein Eng Des Sel, 30(4):291-301 (2017).

Krah S, et al., Engineering bispecific antibodies with defined chain pairing, New Biotechnology, 39:167-173 (2017).

* cited by examiner

ANTIBODIES COMPRISING A COMMON LIGHT CHAIN AND USES THEREOF

CROSS-REFERENCE TO RELATED APPLICATIONS

This application is a continuation of and claims priority to U.S. patent application Ser. No. 16/789,626, filed Feb. 13, 2020 (now U.S. Pat. No. 11,254,736, issued Feb. 22, 2022), which claims priority to U.S. Provisional Patent Application No. 62/806,052, filed Feb. 15, 2019, the entire contents of each of which are hereby incorporated by reference in their entireties.

BACKGROUND

Antibodies have a well-defined structure and will often have a combination of what are referred to $V_H$ and $V_L$ domains. The domains can be in the traditional "Y" type structure where the antibody has two $V_H$ and two $V_L$ peptides. Alternatively, antibodies can be in a scFv format where the $V_H$ and $V_L$ peptides are expressed as a fusion protein and there may be only one each of $V_H$ and $V_L$. It has been thought that binding specificity of antibodies is determined by the CDRs in each peptide that bind to the antigen of interest. However, it would be helpful to generate a generic peptide that can be used irrespective of the target, which will allow greater flexibility in generating antibodies with different specificities for the same or different targets. The present disclosure provides for these needs as well as others.

SUMMARY

In some embodiments, peptides, antibodies, compositions, nucleic acid molecules and other types of molecules as described herein are provided.

In some embodiments, a protein comprising a first amino acid sequence or a first CDR selected from the group consisting of: SEQ ID NOs: 19, 49, 50, 51, 52, 57, 58, 62, 63, 66, 69, 70, 71, 74, 75, and 76; a second amino acid sequence or second CDR selected from the group consisting of: 21, 54, 60, 64, 67, 72, 77, and 79; and a third amino acid sequence or third CDR selected from the group consisting of: 23, 47, 48, 56, 61, 65, 68, 73, 78, and 80 are provided.

In some embodiments, a protein comprising a sequence that is at least, or about, 60%, 70%, 80%, 85%, 90%, 91%, 92%, 93%, 94%, 95%, 96%, 97%, 98%, or 99% identical to, SEQ ID NO: 2 (F10h). SEQ ID NO: 1 (F10), SEQ ID NO: 3 (B9), SEQ ID NO: 4 (B9h), SEQ ID NO: 5 (N6-G3), SEQ ID NO: 6 (N6-C5), SEQ ID NO: 7 (N6-F11), SEQ ID NO: 8 (N5-B4), or SEQ ID NO: 9 (N5-B7) is provided or a sequence of SEQ ID NO: 18-80 and 84.

DETAILED DESCRIPTION

Here it is described and disclosed peptides that can act as light chains for antibodies and can be combined with a variety of heavy chains regardless of the target that the heavy chain binds to.

The heavy chain can be referred to as variable heavy chain ($V_H$). In some embodiments, the $V_H$ can be a human, mouse, chicken, or humanized $V_H$ peptide.

The term "antibody" as used herein is meant in a broad sense and includes immunoglobulin or antibody molecules including polyclonal antibodies, monoclonal antibodies including murine, human, humanized and chimeric monoclonal antibodies and antibody fragments.

The term "humanized antibody", "engineered antibody", "human framework adapted", and "HFA" as used herein, is intended to include antibodies having variable region frameworks derived from sequences of human origin. Furthermore, if the antibody contains a constant region, the constant region can be derived from such human sequences, e.g., human germline sequences, or naturally occurring (e.g., allotypes) or mutated versions of human germline sequences. The humanized antibodies may include amino acid residues not encoded by human sequences (e.g., mutations introduced by random or site-specific mutagenesis in vitro or by somatic mutation in vivo).

In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa and lambda, based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

A "Fab fragment" is comprised of one light chain and the $C_{H1}$ and variable regions of one heavy chain. The heavy chain of a Fab molecule cannot form a disulfide bond with another heavy chain molecule.

An "Fc" region contains two heavy chain fragments comprising the $C_{H1}$ and $C_{H2}$ domains of an antibody. The two heavy chain fragments are held together by two or more disulfide bonds and by hydrophobic interactions of the $C_H3$ domains.

A "Fab' fragment" contains one light chain and a portion or fragment of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form a F(ab') 2 molecule.

A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab') 2 fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

In certain embodiments, monoclonal antibodies herein also include camelized single domain antibodies. See, e.g., Muyldermans et al. (2001) Trends Biochem. Sci. 26:230; Reichmann et al. (1999) J. Immunol. Methods 231:25; WO 94/04678; WO 94/25591; U.S. Pat. No. 6,005,079). In some embodiments, provided single domain antibodies comprising two $V_H$ domains with modifications such that single domain antibodies are formed. In some embodiments the $V_H$ domain is combined with a $V_L$ domain, such as those provided herein.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

The term "antigen" as used herein means any molecule that has the ability to generate antibodies either directly or indirectly. Included within the definition of "antigen" is a protein-encoding nucleic acid. The antigen can also refer to the target being bound by the antibody or a protein.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived. In some embodiments, the CDRs present in the $V_H$ domain determine what the antibody binds to and the CDRs present in the common light chain do not significantly contribute to binding specificity to the target.

The term "homolog" means protein sequences having between 40% and 100% sequence identity to a reference sequence. Percent identity between two peptide chains can be determined by pair wise alignment using the default settings of the AlignX module of Vector NTI v.9.0.0 (Invitrogen Corp., Carslbad, Calif.). In some embodiments, the antibody or fragment thereof has at least 50, 60, 70, 80, 90, 91, 92, 93, 94, 95, 96, 97, 98, or 99% identity to a sequence described herein, such as SEQ ID NOs: 1-9 or a sequence of SEQ ID NO: 18-80, or 84. These can also be referred to as variants. In some embodiments, the sequences or variants have 1, 2, 3, 4, 5, 6, 7, 8, or 9 substitutions as compared to the sequences provided for herein. In some embodiments, the substitution is a conservative substitution. In some embodiments, the mutation or substitution is in the framework region of the light chain. In some embodiments, the substitution is in the CDR regions, such as CDR1, CDR2, or CDR3. In some embodiments, the mutation or substitution is in CDR1 and not in CDR2 or CDR3. In some embodiments, the light chain comprises substitutions or changes in the framework region and not in the CDR regions as provided herein. In some embodiments, light chains or proteins are provided wherein the sequence is at least, or about 50, 60, 70, 80, 90, 91, 92, 93, 94, 95, 96, 97, 98, or 99% identical to SEQ ID NOs: 1-9, provided that the sequence comprise a first amino acid sequence or a first CDR selected from the group consisting of: SEQ ID NOs: 19, 49, 50, 51, 52, 57, 58, 62, 63, 66, 69, 70, 71, 74, 75, 76, and 84; a second amino acid sequence or second CDR selected from the group consisting of: 21, 54, 60, 64, 67, 72, 77, and 79; and a third amino acid sequence or third CDR selected from the group consisting of: 23, 47, 48, 56, 61, 65, 68, 73, 78, and 80. Thus, in some embodiments, the CDRs are not variants of those provided herein. In some embodiments, the antibody has conservative substitutions as compared to a sequence described herein. Antibodies having conservative substitutions in the heavy and light chain sequences shown in Table 1 are encompassed within the scope of the disclosed subject matter. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in the table below.

TABLE 1

Exemplary Conservative Substitutions:

| Original Residue | Exemplary Conservative Substitutions |
|---|---|
| Ala | Val, Leu, Ile |
| Arg | Lys, Gin, Asn |

TABLE 1-continued

Exemplary Conservative Substitutions:

| Original Residue | Exemplary Conservative Substitutions |
| --- | --- |
| Asn | Gin |
| Asp | Glu |
| Cys | Ser, Ala |
| Gin | Asn |
| Gly | Pro,Ala |
| His | Asn, Gin, Lys, Arg |
| Ile | Leu, Val, Met, Ala, Phe |
| Leu | Ile, Val, Met, Ala, Phe |
| Lys | Arg, Gin, Asn |
| Met | Leu, Phe, He |
| Phe | Leu, Val, lie, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | He, Met, Leu, Phe, Ala |

The term "in combination with" as used herein means that the described agents can be administered to an animal together in a mixture, concurrently as single agents or sequentially as single agents in any order.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495 497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES: A Laboratory Manual Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb may be cultivated in vitro, in situ or in vivo. Production of high titers of mAbs in vivo or in situ makes this the presently preferred method of production.

Chimeric antibodies are molecules different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273 3277 (1984); Morrison et al., Proc. Natl. Acad. Sci. USA 81:6851 6855 (1984); Boulianne et al., Nature 312:643 646 (1984); Cabilly et al., European Patent Application 125023 (published Nov. 14, 1984); Neuberger et al., Nature 314:268 270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066 1074 (1986); Robinson et al., International Patent Publication No. WO1987/002671 (published May 7, 1987); Liu et al., Proc. Natl. Acad. Sci. USA 84:3439 3443 (1987); Sun et al., Proc. Natl. Acad. Sci. USA 84:214 218 (1987); Better et al., Science 240:1041 1043 (1988); and Harlow and Lane Antibodies, a Laboratory Manual Cold Spring Harbor Laboratory (1988)). These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., Nature 256:495-497 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., Proc. Natl. Acad. Sci. (USA), 86:10029-10032 (1989) and Hodgson et al., Bio/Technology, 9:421 (1991).

As used herein, the term "humanized antibody" refers to forms of antibodies that contain sequences from both human and non-human (e.g., murine, rat, chicken) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only. Similarly, "chicken antibody" refers to an antibody that comprises chicken immunoglobulin sequences only. For example, the term "chicken antibody" refers to an antibody that was raised in a chicken. For example, a protein of interest can be introduced into a chicken, such as in a VLP, to stimulate an immune response against the protein of interest to produce antibodies in the chicken. The antibody can then be humanized or otherwise modified as desired.

In addition to the antibodies described herein, exemplary human framework sequences useful for humanization are disclosed at, e.g., www"dot"ncbi"dot"nlm"dot"nih"dot"gov/entrez/query"dot"fcgi; www"dot"ncbi"dot"nih"dot"gov/igblast; www"dot"atcc"dot"org/phage/hdb"dot"html; www"dot"mrc-cpe"dot"cam"dot"ac"dot"uk/ALIGNMENTS"dot"php; "dot" www"dot"kabatdatabase"dot"com/top"dot"html; ftp"dot"ncbi"dot"nih"dot"gov/repository/kabat; www"dot"sciquest"dot"com; www"dot"abcam"dot"com; www"dot"antibodyresource-"dot"com/onlinecomp"dot"html; www"dot"public"dot"i-astate"dot"edu/"dot"about"dot"pedro/research_tools"dot"html; www"dot"whfreeman"dot"com/immunology/CH05/kuby05"dot"htm; www"dot"hhmi"dot"org/grants/lectures/1996/vlab; www"dot"path"dot"cam"dot"ac"dot"uk/"dot"about-"dot"mrc7/mikeimages"dot"html; mcb"dot"harvard"dot"edu/BioLinks/Immunology"dot"html; www"dot"immunologylink"dot"com; pathbox"dot"wustl"dot"edu/"dot"about"dot"hcenter/index"dot"html; www"dot"appliedbiosystems"dot"com; www"dot"nal"dot"usda"dot"gov/awic/pubs/antibody; www"dot"m"dot"e-hime-u"dot"ac"dot"jp/"dot"about"dot"yasuhito/Elisa-"dot"html; www"dot"biodesign"dot"com; www"dot"cancerresearchuk"dot"org; www"dot"biotech-"dot"ufl"dot"edu; www"dot"isac-net"dot"org; baserv"dot"uci"dot"kun"dot"nl/"dot"about"dot"jraats/links1"dot"html; www"dot"recab"dot"uni-hd"dot"de/immuno"dot"bme"dot"nwu"dot"edu; www"dot"mrc-cpe"dot"cam"dot"ac"dot"uk; www"dot"ibt"dot"unam"dot"mx/vir/V_mice"dot"html; http://www"dot"bioinf"dot"org"dot"uk/abs; antibody"dot"bath"dot"ac"dot"uk; www"dot"unizh"dot"ch; www"dot"cryst"dot"bbk"dot"ac"dot"uk/"dot"about"dot"ubcg07s; www"dot"nimr"dot"mrc"dot"ac"dot"uk/CC/ccaewg/ccaewg"dot"html; www"dot"path"dot"cam"dot"ac"dot"uk/"dot"about"dot"mrc7/humanisation/TAHHP"dot"html; www"dot"ibt"dot"unam"dot"mx/vir/structure/stat_aim"dot"html; www"dot"biosci"dot"missouri"dot"edu/smithgp/index"dot"html; www"dot"jerini"dot"de; imgt"dot"cines"dot"fr; and Kabat et al., Sequences of Proteins of Immunological Interest, U.S. Dept. Health (1987), each entirely incorporated herein by reference. The "dot" in the world wide web addresses referenced herein can be replaced with a "." as appropriate.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

As used herein, the term "hypervariable region" refers to the amino acid residues of an antibody that are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). As used herein, the term "framework" or "FR" residues refers to those variable domain residues other than the hypervariable region residues defined herein as CDR residues. CDRs provide the majority of contact residues for the binding of the antibody to the antigen or epitope. CDRs of interest can be derived from donor antibody variable heavy and light chain sequences, and include analogs of the naturally occurring CDRs, which analogs also share or retain the same antigen binding specificity and/or neutralizing ability as the donor antibody from which they were derived.

Additionally, in some embodiments, the antibodies can take the form of a full length antibody, single-domain antibody, a single-chain antibody (scFv), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a F(ab')2, a peptide mimetic molecule, or a synthetic molecule, as described in U.S. Pat. Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004, 746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of each of which are hereby incorporated by reference in their entireties. See also, Storz MAbs. 2011 May-June; 3(3): 310-317, which is hereby incorporated by reference.

In some embodiments, the antibodies described herein can include, but are not limited to, at least one of a heavy chain constant region ($H_c$), a heavy chain variable region (H$_v$), a light chain variable region (L$_v$) and a light chain constant region (L$_c$), wherein a polyclonal Ab, monoclonal Ab, fragment and/or regions thereof include at least one heavy chain variable region (H$_v$) or light chain variable region (L$_v$). The L$_v$ can also be referred to as V$_L$. The H$_v$ can also be referred to as V$_H$. The antibodies can also be monoclonal antibodies that are made by immunizing chickens. The variable chains from the nucleic acid sequences encoding the isolated monoclonal antibodies can be isolated by using techniques, such as but not limited to, PCR. The variable chains isolated by these techniques can then be placed in a scFv vector with a human Fc. Accordingly, the antibodies can be antibodies that have a human Fc and two scFv arms. The antibodies, such as those described here and throughout the present disclosure can then be modified to be human or humanized antibodies. Examples of how to modify an antibody, including chicken antibodies, can be found in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vásquez M, Kumar S. (2004); and "Humanization of a chicken anti-IL-12 monoclonal antibody" Immunol Methods 295 (1-2): 9-19; Nishibori N, Horiuchi H, Furusawa S, Matsuda H. (2006) "Humanization of chicken monoclonal antibody using phage display system" Mol Immunol. 43 (6): 634-42, each of which is incorporated by reference in its entirety.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in chickens, goats, rabbits, or other small animals.

As used herein, the term "antigen binding region" refers to that portion of an antibody molecule which contains the amino acid residues that interact with an antigen (e.g. a target protein) and confer on the antibody its specificity and affinity for the antigen. The antibody region includes the "framework" amino acid residues necessary to maintain the proper conformation of the antigen-binding residues. In some embodiments, the antigen binding region will be of murine origin. In some embodiments, the antigen binding region can be derived from other animal species, in particular rodents such as rabbit, rat or hamster, or birds such as chickens. It has been shown that the antigen-binding function of an antibody can be performed by fragments of a full-length antibody. Examples of binding fragments encompassed within the term "antigen-binding portion" of an antibody include a Fab fragment, a monovalent fragment having the V$_L$, V$_H$, CL and CH1 domains; a F(ab)$_2$ fragment, a bivalent fragment comprising two Fab fragments linked by a disulfide bridge(s) at a hinge region; a Fd fragment having the V$_H$ and CH1 domains; a Fv fragment having the V$_L$ and V$_H$ domains of a single arm of an antibody; a domain antibody or dAb fragment (Ward et al., 1989 Nature 341: 544-546), which consists of a V$_H$ domain; and an isolated complementarity determining region (CDR), especially a CDR3 (See for example the WO03/025019, the contents of which are incorporated herein by reference).

The term "Complementarity Determining Regions (CDRs)" is based on sequence variability (Wu and Kabat, J. Exp. Med. 132:211-250, 1970). There are six CDRs—three in the variable heavy chain, or V$_H$, and are typically designated H-CDR1, H-CDR2, and H-CDR3, and three CDRs in the variable light chain, or V$_L$, and are typically designated L-CDR1, L-CDR2, and L-CDR3 (Kabat et al., Sequences of Proteins of Immunological Interest, 5th Ed. Public Health Service, National Institutes of Health, Bethesda, Md., 1991). "Hypervariable region", "HVR", or "HV" refer to the regions of an antibody variable domain which are variable in structure as defined by Chothia and Lesk (Chothia and Lesk, Mol. Biol. 196:901-917, 1987). There are six HVRs, three in V$_H$ (H1, H2, H3) and three in V$_L$ (L1, L2, L3). Chothia and Lesk refer to structurally conserved HVs as "canonical structures." Another method of describing the regions that form the antigen-binding site has been proposed by Lefranc (Lefranc et al., Developmental & Comparative Immunology 27:55-77, 2003) based on the comparison of V domains from immunoglobulins and T-cell receptors (Lefranc et al., Developmental & Comparative Immunology 27:55-77, 2003). The antigen-binding site can also be delineated based on "Specificity Determining Residue Usage (SDRU)", according to Almagro (Almagro, Mol. Recognit. 17:132-43, 2004), where SDRU refers to amino acid residues of an immunoglobulin that are directly involved in antigen contact.

Furthermore, although the two domains of the Fv fragment, V$_L$ and V$_H$, are encoded by separate genes naturally, they can be joined, using recombinant methods, by a synthetic linker that enables them to be made as a single protein chain in which the V$_L$ and V$_H$ regions pair to form monovalent molecules (known as single chain Fv (scFv); see e.g., Bird et al., 1988 Science 242:423-426; and Huston et al., 1988 Proc. Nat. Acad. Sci. 85:5879-5883). Such single chain antibodies are encompassed by the term "antigen-binding portion" of an antibody. These antibody fragments are obtained using conventional techniques known to those of skill in the art, and can be used in the same manner as intact antibodies.

An "isolated antibody," as used herein, refers to an antibody that is substantially free of other antibodies having different antigenic specificities. Moreover, an isolated antibody may be substantially free of other cellular material and/or chemicals. An isolated antibody can also be sterile or pyrogen free or formulated as injectable pharmaceutical as described herein.

In some embodiments, the source for the DNA encoding a non-human antibody include cell lines which produce antibody, such as hybrid cell lines commonly known as hybridomas.

An "antigen" can be a molecule or a portion of a molecule capable of being bound by an antibody which can be additionally capable of inducing an animal to produce antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens. In some embodiments, antigens that bind antibodies, fragments and regions of the antibodies include at least 5 amino acids. In some embodiments, the antigen is a target protein expressed on the surface of a cell or particle. In some embodiments, the cell is an intact cell. An intact cell is a cell that has not been lysed or broken open with the use of detergents or other reagents. A cell that has been treated with detergents or other reagents that breaks up the cellular membrane or punches holes in a cellular membrane is not an intact cell. By expressing the receptor on the surface of the cell or particle, e.g. lipoparticle, the receptor can present conformational epitopes that may otherwise not be present if purified protein is used. An example is provided herein. In some embodiments, an adjuvant is not used, but an adjuvant can be used. In some embodiments, the particles are injected into a bird (e.g. chicken) to stimulate an immune response and generate antibodies against the protein present on the surface of the particle. Particles suitable for the generation of antibodies are described in U.S. Pat. Nos. 8,377,691, 7,763,258, 8,158,130 and U.S. Patent Application Publication Nos. 20050123563 and 20120195882, each of which is hereby incorporated by reference. These publications and patents describe the generation of various particles, including lipoparticles, that can be used to express membrane spanning proteins (e.g. multiple-membrane spanning proteins, ion channels, and the like).

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. Example of epitopes include, but are not limited to, The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC CRL1581) and the myeloma P3X63Ag8 (ATCC TIB9), or its derivatives. See, e.g., Ausubel infra, Harlow infra, and Colligan infra, the contents of which references are incorporated entirely herein by reference.

The antibodies can be generated according the examples provided herein. Once the sequences are known, the antibodies can also be generated according to known methods. The antibodies can also be converted to different types, such as being converted to Human IgGs and the like. By converting the antibodies to a human antibody, a human subject should not identify the antibodies as foreign. This will lead to a more effective response. The conversion of a non-human IgG antibody to a human IgG antibody is well known and can routinely be done once the native sequence is known. As discussed herein, the antibodies can be modified according to known methods. Such methods are described in, for example, Riechmann L, Clark M, Waldmann H, Winter G (1988). Reshaping human antibodies for therapy". Nature 332 (6162): 332-323; Tsurushita N, Park M, Pakabunto K, Ong K, Avdalovic A, Fu H, Jia A, Vásquez M, Kumar S. (2004); and "Humanization of a chicken anti-IL-12 monoclonal antibody" Immunol Methods 295 (1-2): 9-19; Nishibori N, Horiuchi H, Furusawa S, Matsuda H. (2006) "Humanization of chicken monoclonal antibody using phage display system" Mol Immunol. 43 (6): 634-42, each of which is incorporated by reference in its entirety.

The antibody-producing cell contributing the nucleotide sequences encoding the antigen-binding region of the chimeric antibody can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g., Ausubel infra, Harlow infra, and Colligan infra, the contents of which references are incorporated entirely herein by reference.

The cell fusions are accomplished by standard procedures well known to those skilled in the field of immunology. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

The antigen-specific murine or chimeric mAb can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In some embodiments, the antibody is a MAb which binds to a target protein. In some embodiments, the antibody binds to amino acids of an epitope of the target protein.

In some embodiments, the antibody comprises a sequence as provided for herein.

The sequences of the antibodies can be modified to yield human IgG antibodies. The conversion of the sequences provided herein can be modified to yield other types of antibodies. The CDRs can also be linked to other antibodies, proteins, or molecules to create antibody fragments that bind to a target protein. The CDRs and antibody sequences provided herein also be humanized or made fully human according to known methods. The sequences can also be made into chimeric antibodies as described herein.

In some embodiments, the antibody comprises an amino acid sequence comprising a sequence provided for herein or a fragment thereof. In some embodiments, the antibody comprises one or more amino acid sequences as provided herein, an antigen binding fragments, thereof, or a human IgG variant thereof. "A human IgG variant thereof" refers to an antibody that has been modified to be a human IgG when the starting antibody is not a human IgG antibody.

As described herein the production of antibodies with a known sequence is routine and can be done by any method. Accordingly, in some embodiments, a nucleic acid encoding an antibody or fragment thereof is provided. In some embodiments, the nucleic acid encodes a sequence provided for herein. The antibodies can also be modified to be chimeric antibodies or human antibodies. The antibodies can also be used in injectable pharmaceutical compositions. As also described herein, the antibodies can be isolated antibodies or engineered antibodies.

In some embodiments, "derivatives" of the antibodies, fragments, regions or derivatives thereof, which term includes those proteins encoded by truncated or modified genes to yield molecular species functionally resembling the immunoglobulin fragments are provided. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

Fragments include, for example, Fab, Fab', F(ab')$_2$ and Fv. These fragments lack the Fc fragment of intact antibody, clear more rapidly from the circulation, and can have less non-specific tissue binding than an intact antibody (Wahl et al., J. Nucl. Med. 24:316 325 (1983)). These fragments are produced from intact antibodies using methods well known in the art, for example by proteolytic cleavage with enzymes such as papain (to produce Fab fragments) or pepsin (to produce F(ab')$_2$ fragments).

The identification of these antigen binding region and/or epitopes recognized by Abs described herein provide the information necessary to generate additional monoclonal antibodies with similar binding characteristics and therapeutic or diagnostic utility that parallel the embodiments of this application.

The proteins or antibodies can also be provided as nucleic acid sequences/molecules. The nucleic acid sequence encoding an antibody or protein described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize a target protein or antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions can be derived from a human fetal liver library, by known methods. Human C region genes can be derived from any human cell including those which express and produce human immunoglobulins. The human $C_H$ region can be derived from any of the known classes or isotypes of human H chains, including gamma, µ, α, δ or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG$_1$), gamma 3 (IgG$_3$), gamma 4 (IgG$_4$), or µ (IgM). The human $C_L$ region can be derived from either human L chain isotype, kappa or lambda.

Genes encoding human immunoglobulin C regions can be obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CH$_1$ domain and hinge region of the H chain, followed by a translational stop codon to yield the truncated molecule.

Generally, the murine, human or murine and chimeric antibodies, fragments and regions of the antibodies described herein are produced by cloning DNA segments encoding the H and L chain antigen-binding regions of the antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the chimeric antibody according to some of the embodiments described herein involve several steps, as exemplified below: 1. isolation of messenger RNA (mRNA) from the cell line producing an anti-antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region (Cγ-1). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human Cγ-1 region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions.

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w) pure, 90-95% pure; and, at least 95%, 96%, 97%, 98%, 99%, or 100% (w/w) pure. In some embodiments, the antibody is purified.

The terms "specific binding," "specifically binds," and the like, mean that two or more molecules form a complex that is measurable under physiologic or assay conditions and is selective. An antibody or antigen binding protein or other molecule is said to "specifically bind" to a protein, antigen, or epitope if, under appropriately selected conditions, such binding is not substantially inhibited, while at the same time non-specific binding is inhibited. Specific binding is characterized by a high affinity and is selective for the compound, protein, epitope, or antigen. Nonspecific binding usually has a low affinity. Binding in IgG antibodies for example is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody or antigen binding protein carrying the antigen-binding domain will generally not bind other antigens. In some embodiments, the capture reagent has a Kd equal or less than $10^{-9}$M, $10^{-10}$M, or $10^{-11}$M for its binding partner (e.g. antigen). In some embodiments, the capture reagent has a Ka greater than or equal to $10^9 M^{-1}$ for its binding partner.

Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain ($V_L$) and a constant (C) domain (CL). Each heavy chain is composed of an N-terminal V domain ($V_H$), three or four C domains (CHs), and a hinge region. The CH domain most proximal to $V_H$ is designated CH1. The $V_H$ and $V_L$ domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, $V_H$, CL, $V_L$, CDR, and/or FR structure, comprises active fragments. For example, active fragments may consist of the portion of the $V_H$, $V_L$, or CDR subunit that binds the antigen, i.e., the antigen-binding fragment, or the portion of the CH subunit that binds to and/or activates an Fc receptor and/or complement.

In addition to the fragments described herein, non-limiting examples of binding fragments encompassed within the term "antigen-specific antibody" used herein include: (i) an Fab fragment, a monovalent fragment consisting of the $V_L$, $V_H$, CL and CH1 domains; (ii) an F(ab')2 fragment, a bivalent fragment comprising two Fab fragments linked by a disulfide bridge at the hinge region; (iii) an Fd fragment consisting of the $V_H$ and CH1 domains; (iv) an Fv fragment consisting of the $V_L$ and $V_H$ domains of a single arm of an antibody, (v) a dAb fragment, which consists of a $V_H$ domain; and (vi) an isolated CDR. Furthermore, although the two domains of the Fv fragment, $V_L$ and $V_H$, are coded for by separate genes, they may be recombinantly joined by a synthetic linker, creating a single protein chain in which the $V_L$ and $V_H$ domains pair to form monovalent molecules (known as single chain Fv (scFv)). The most commonly used linker is a 15-residue (Gly4Ser)$_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof.

These antibodies can be obtained using conventional techniques known to those skilled in the art and described herein, and the fragments are used in the same manner as intact antibodies. Antibody diversity is created by multiple germline genes encoding variable domains and a variety of somatic events. The somatic events include recombination of variable gene segments with diversity (D) and joining (J) gene segments to make a complete $V_H$ domain, and the recombination of variable and joining gene segments to make a complete $V_L$ domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random $V_H$-$V_L$ pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and biosensor analysis, to identify one or more hybridomas that produce an antibody that specifically interacts with a molecule or compound of interest.

As an alternative to preparing monoclonal antibody-secreting hybridomas, a monoclonal antibody to a polypeptide may be identified and isolated by screening a recombinant combinatorial immunoglobulin library (e.g., an antibody phage display library) with a polypeptide described herein to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

Administration, Compositions, and Kits Comprising the Antibodies

The antibodies comprising the peptides provided for herein can be used in therapeutic antibodies or antibodies that are used to detect or bind to different targets.

In the case of therapeutic administration, any active form of the antibody can be administered, including, but not limited to scFv, Fab and F(ab')2 fragments. These are just examples and are not intended to be limited and any antibody form as provided herein or known can be used.

In some embodiments, the antibodies used are compatible with the recipient species such that the immune response to the MAbs does not result in an unacceptably short circulating half-life or induce an immune response to the MAbs in the subject. In some embodiments, the MAbs administered exhibit some secondary functions such as binding to Fc receptors of the subject and activation of antibody dependent cell mediated cytotoxicity (ADCC) mechanisms.

Treatment of individuals may comprise the administration of a therapeutically effective amount of the antibodies described herein. The antibodies can be provided in a kit as described below. The antibodies can be used or administered alone or in admixture with another therapeutic, analgesic, or diagnostic agent. In providing a patient with an antibody, or fragment thereof, capable of binding to the target protein, the dosage of administered agent will vary depending upon such factors as the patient's age, weight, height, sex, general medical condition, previous medical history, etc.

Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41). Additional pharmaceutical methods may be employed to control the duration of action. Controlled release preparations may be achieved through the use of polymers to complex or absorb the compounds. Another possible method to control the duration of action by controlled release preparations is to incorporate the compounds of into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly(methylmethacylate)-microcapsules, respectively, or in colloidal drug delivery systems, for example, liposomes, albumin microspheres, microemulsions, nanoparticles, and nanocapsules or in macroemulsions.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the antibody may be given which is not based upon the weight of the patient such as an amount in the range of 1 ug-100 ug, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

The antibody compositions described herein can be prepared for use for parenteral (subcutaneous, intramuscular or intravenous) or any other administration particularly in the form of liquid solutions or suspensions. The formulation can also be suitable for an injectable formulation. In some embodiments, the injectable formulation is sterile. In some embodiments, the injectable formulation is pyrogen free. In some embodiments, the formulation is free of other antibodies that bind to other antigens other than an antigen described herein.

The antibody that may comprise a common light chain as provided for herein can be administered as a therapeutically effective amount. An amount is said to be sufficient or a "therapeutically effective amount" to "affect" the reduction of symptoms if the dosage, route of administration, and dosing schedule of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient.

The antibodies can be formulated according to known methods to prepare pharmaceutically useful compositions, whereby these materials, or their functional derivatives, are combined in admixture with a pharmaceutically acceptable carrier vehicle. The treatment may be given in a single dose schedule, or a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Kits are also provided which are useful for carrying out embodiments described herein. The present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

Yet another aspect provided for herein is a kit for detecting a protein in a biological sample. The kit includes a container holding one or more antibodies which comprise a common light chain (e.g. one of SEQ ID NO: 1-9 or a sequence of SEQ ID NO: 18-80 or 84) and instructions for using the antibody for the purpose of binding to a target protein or antigen to form an immunological complex and detecting the formation of the immunological complex such that the presence or absence of the immunological complex correlates with presence or absence of the target protein (or antigen) in the sample. Examples of containers include multiwell plates which allow simultaneous detection of a target protein in multiple samples.

In some embodiments, antibodies that bind to a target protein are provided. In some embodiments, the antibody is isolated. In some embodiments, the antibody binds specifically. In some embodiments, the antibody binds to a target protein that is properly folded. In some embodiments, the antibody binds to a target protein in a cell membrane. In some embodiments, the antibody is a multiple membrane spanning protein. In some embodiments, the protein is a seven transmembrane protein. In some embodiments, the protein is a four transmembrane protein. In some embodiments, the antibody binds to a target protein that is in a cell membrane in an intact cell. In some embodiments, the antibody inhibits or neutralizes the function of a target protein. As used herein, the term "neutralize" means that the activity or function of the protein is inhibited. In some embodiments, the antibody is used as a targeting moiety to deliver another therapeutic to the cells expressing the target protein. In some embodiments, the antibody comprising the common light chain is part of a multi-specific therapeutic where one part of the molecule binds to the target protein and another part of the therapeutic binds to another target. In some embodiments, the other part is a CD3 binding molecule (e.g. CD3 antibody) or another molecule that facilitates ADC, ADCC, or CAR-T therapy. The inhibition can be complete or partial. In some embodiments, the activity or function of the target protein is inhibited, modulated, or enhanced at least 10, 20, 30, 40, 50, 60, 70, 80, 90, 95, or 99%. The percent modulation can be based upon the function or activity of the protein in the absence of the antibody.

In some embodiments, the antibody comprises a sequence as provided for herein or antigen binding fragment thereof. In some embodiments, the antibody comprises a heavy chain CDR or an antigen binding fragment thereof described herein. The heavy chain may be one or more of the heavy chains described herein. In some embodiments, the antibody comprises a light chain, or an antigen binding fragment thereof as described herein.

In some embodiments, methods of detecting the presence or absence of a target protein in a sample are provided, the method comprising contacting a sample with one or more antibodies described herein detecting the binding of the target protein by the antibody. In some embodiments, the detection of the binding indicates the presence of the target protein or molecule; or the absence of the detection of the binding to the target protein (antigen) indicates the absence of the target protein (antigen). The detecting can be done with any known method, such as using a biosensor, ELISA, sandwich assay, flow cytometry, and the like. However, in some embodiments, the method comprises detecting the presence of the protein in non-denaturing conditions. The non-denaturing conditions can be used so that the protein of interest is detected in its native, or properly folded form.

In some of the embodiments of the methods provided herein, the antibody is any antibody or fragment thereof as provided herein.

In some embodiments, the protein or an antibody comprises a sequence as set forth in the following table:

| Clone Name | SEQ ID NO: | Sequence |
|---|---|---|
| F10-V$_L$ | SEQ ID NO: 1 | ALTQPSSVSANPGETVKITCSGGY NGHYGWYQQKSPGSAPVTVIYSNN QRPSNIPSRFSGSTSGSTSTLTIT GVRAEDEAVYFCGGYDSSAGIFGA GTTLTVL |
| F10h-V$_L$ | SEQ ID NO: 2 | SYELTQPPSVSVSPGQTARITCSG GYNGHYGWYQQKPGQAPVLVIYSN NQRPSGIPERFSGSSSGTTVTLTI SGVQAEDEADYYCGGYDSSAGIFG GGTKLTVL |
| B9-V$_L$ | SEQ ID NO: 3 | ALTQPSSVSANPGETVKITCSGGG SSNYYGWYQQKSPGSAPVTLIYGT NKRPSDIPSRFSGSKSGSTGTLTI TGVQADDEAVYFCGSADSSTNAGI FGAGTTLTVL |
| B9h-V$_L$ | SEQ ID NO: 4 | SYELTQPPSVSVSPGQTARITCSG GGSSNYAGWYGYYQQKPGQAPVTV IYGTNKRPSGIPERFSGSSSGTTV TLTISGVQAEDEAVYYCGSADSST NAGIFGAGTKLTVL |
| N6-G3 | SEQ ID NO: 5 | SYELTQPPSVSVSPGQTARITCSG GSGSYGYYGWYQQKPGQAPVLVIY GTNKRPSGIPERFSGSSSGTTVTL TISGVQAEDEADYYCGSTDSNYVG IFGGGTKLTVL |
| N6-C5 | SEQ ID NO: 6 | SYELTQPPSVSVSPGQTARITCSG GYNGHYGWYQQKPGQAPVLVIYSN NQRPSGIPERFSGSSSGTTVTLTI SGVQAEDEADYYCGNADSNYVGIF GGGTKLTVL |
| N6-F11 | SEQ ID NO: 7 | SYELTQPPSVSVSPGQTARITCSG GGSSNYYGWYQQKPGQAPVLVIYS NNQRPSGIPERFSGSSSGTTVTLT ISGVQAEDEADYYCGSADSSTNAG IFGGGTKLTVL |
| N5-B4 | SEQ ID NO: 8 | SYELTQPPSVSVSPGQTARITCSG GSGSYGYYGWYQQKPGQAPVLVIY SNNQRPSGIPERFSGSSSGTTVTL TISGVQAEDEADYYCGSADSSTNA GIFGGGTKLTVL |
| N5-B7 | SEQ ID NO: 9 | SYELTQPPSVSVSPGQTARITCSG GSGSYGYYGWYQQKPGQAPVLVIY GTNKRPSGIPERFSGSSSGTTVTL TISGVQAEDEADYYCGSADSSTNA GIFGGGTKLTVL |

In some embodiments, an antibody comprises a V$_L$ protein of any one of SEQ ID NOs: 1-9 or one or more sequences of SEQ ID NOs:18-80 or 84. In some embodiments, the protein comprises a sequence that is at least, or about, 60%, 70%, 80%, 85%, 90%, 91%, 92%, 93%, 94%, 95%, 96%, 97%, 98%, or 99% identical to the sequence. In some embodiments, a protein is provided that comprises a sequence of any one of SEQ ID NOs: 1-9 or SEQ ID NOs:18-80 or 84. In some embodiments, the protein comprises 1, 2, 3, 4, 5, 6, 7, 8, 9, or 10 substitutions. In some embodiments, the substitution is a conservative substitution. In some embodiments, the substitution is a conservative substitution. In some embodiments, the mutation or substitution is in the framework region of the light chain. In some embodiments, the substitution is in the CDR regions, such as CDR1, CDR2, or CDR3. In some embodiments, the mutation or substitution is in CDR1 and not in CDR2 or CDR3. In some embodiments, the light chain comprises substitutions or changes in the framework region and not in the CDR regions as provided herein. In some embodiments, light chains or proteins are provided wherein the sequence is at least, or about 50, 60, 70, 80, 90, 91, 92, 93, 94, 95, 96, 97, 98, or 99% identical to SEQ ID NOs: 1-9, provided that the sequence comprise a first amino acid sequence or a first CDR selected from the group consisting of: SEQ ID NOs: 19, 49, 50, 51, 52, 57, 58, 62, 63, 66, 69, 70, 71, 74, 75, 76, and 84; a second amino acid sequence or second CDR selected from the group consisting of: 21, 54, 60, 64, 67, 72, 77, and 79; and a third amino acid sequence or third CDR selected from the group consisting of: 23, 47, 48, 56, 61, 65, 68, 73, 78, and 80. Thus, in some embodiments, the CDRs are not variants of those provided herein. Percent identity can be determined as provided for herein or using the default parameters of BLASTP for aligning two sequences available through the National Center for Biotechnology Information website.

In some embodiments, a protein or antibody comprises a sequence as illustrated in the following table, Table 2 (the different segments can be linked together in a contiguous sequence):

TABLE 2

| ID | FW1 | LCDR1 | FW2 | LCDR2 | FW3 | LCDR3 | FW4 |
|---|---|---|---|---|---|---|---|
| F10 chicken | ALTQPSSVSA NPGETVKITC (SEQ ID NO: 18) | SGGYNGHYG (SEQ ID NO: 19) | WYQQKSPG SAPVTVIY (SEQ ID NO: 20) | SNNQRPS (SEQ ID NO: 21) | NIPSRFSGSTSGSTST LTITGVRAEDEAVYFC (SEQ ID NO: 22) | GGYDSSAGI (SEQ ID NO: 23) | FGAGTTLTVL (SEQ ID NO: 24) |
| F10VL3-25 | SYELTQPPSVS VSPGQTARITC (SEQ ID NO: 25) | SGGYNGHYG (SEQ ID NO: 19) | WYQQKPGQ APVLVIY (SEQ ID NO: 26) | SNNQRPS (SEQ ID NO: 21) | GIPERFSGSSSGTTVT LTISGVQAEDEADYYC (SEQ ID NO: 27) | GGYDSSAGI (SEQ ID NO: 23) | FGGGTKLTVL (SEQ ID NO: 29) |
| F10VL3-25 L46T | SYELTQPPSVS VSPGQTARITC (SEQ ID NO: 25) | SGGYNGHYG (SEQ ID NO: 19) | WYQQKPGQ APVTVIY (SEQ ID NO: 30) | SNNQRPS (SEQ ID NO: 27) | GIPERFSGSSSGTTVT LTISGVQAEDEADYYC (SEQ ID NO: 27) | GGYDSSAGI (SEQ ID NO: 23) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| F10VL3-1 | SYELTQPPSVS VSPGQTASITC (SEQ ID NO: 31) | SGGYNGHYG (SEQ ID NO: 19) | WYQQKPGQ SPVLVIY (SEQ ID NO: 32) | SNNQRPS (SEQ ID NO: 21) | GIPERFSGSNSGNTAT LTISGTQAMDEADYYC (SEQ ID NO: 33) | GGYDSSAGI (SEQ ID NO: 23) | TGTGTKLTVL (SEQ ID NO: 34) |
| F10VL3-1L46T | SYELTQPPSVS VSPGQTASITC (SEQ ID NO: 31) | SGGYNGHYG (SEQ ID NO: 19) | WYQQKPGQ SPVTVIY (SEQ ID NO: 35) | SNNQRPS (SEQ ID NO: 21) | GIPERFSGSNSGNTAT LTISGTQAMDEADYYC (SEQ ID NO: 33) | GGYDSSAGI (SEQ ID NO: 23) | TGTGTKLTVL (SEQ ID NO: 34) |
| F10VL3-21 | SYELTQPPSVS VAPGKTARITC (SEQ ID NO: 36) | SGGYNGHYG (SEQ ID NO: 19) | WYQQKPGQ APVLVIY (SEQ ID NO: 26) | SNNQRPS (SEQ ID NO: 21) | GIPERFSGSNSGNTAT LTISRVEAGDEADYYC (SEQ ID NO: 37) | GGYDSSAGI (SEQ ID NO: 23) | FGGGTKLTVL (SEQ ID NO: 29) |
| F10VL3-21L46T | SYELTQPPSVS VAPGKTARITC (SEQ ID NO: 36) | SGGYNGHYG (SEQ ID NO: 19) | WYQQKPGQ APVTVIY (SEQ ID NO: 30) | SNNQRPS (SEQ ID NO: 21) | GIPERFSGSNSGNTAT LTISRVEAGDEADYYC (SEQ ID NO: 37) | GGYDSSAGI (SEQ ID NO: 23) | FGGGTKLTVL (SEQ ID NO: 29) |
| F10VL3-19 | SYELTQDPAVS VALGQTVRITC (SEQ ID NO: 38) | SGGYNGHYG (SEQ ID NO: 19) | WYQQKPGQ APVLVIY (SEQ ID NO: 26) | SNNQRPS (SEQ ID NO: 21) | NIPDRFSGSSSGNTAS LTITGAQAEDEADYYC (SEQ ID NO: 39) | GGYDSSAGI (SEQ ID NO: 23) | FGSGTKLTVL (SEQ ID NO: 40) |
| F10VL3-19L46T | SYELTQDPAVS VALGQTVRITC (SEQ ID NO: 38) | SGGYNGHYG (SEQ ID NO: 19) | WYQQKPGQ APVTVIY (SEQ ID NO: 30) | SNNQRPS (SEQ ID NO: 21) | NIPDRFSGSSSGNTAS LTITGAQAEDEADYYC (SEQ ID NO: 39) | GGYDSSAGI (SEQ ID NO: 23) | FGSGTKLTVL (SEQ ID NO: 40) |
| F10VL3-25 93% | SYELTQPPSVS VSPGQTARITC (SEQ ID NO: 25) | SGGYNGHYG (SEQ ID NO: 19) | WYQQKPGQ APVTVIY (SEQ ID NO: 30) | SNNQRPS (SEQ ID NO: 21) | NIPERFSGSTSGSTST LTISGVQAEDEADYYC (SEQ ID NO: 41) | GGYDSSAGI (SEQ ID NO: 23) | FGGGTKLTVL (SEQ ID NO: 29) |
| F10VL3-19 93% | SYELTQDPAVS VALGQTVRITC (SEQ ID NO: 38) | SGGYNGHYG (SEQ ID NO: 19) | WYQQKPGQ APVTVIY (SEQ ID NO: 30) | SNNQRPS (SEQ ID NO: 21) | NIPDRFSGSTSGSTAS LTITGAQAEDEADYYC (SEQ ID NO: 42) | GGYDSSAGI (SEQ ID NO: 23) | FGSGTKVTVL (SEQ ID NO: 43) |
| F10VL3-1 93% | SYELTQPPSVS VSPGQTASITC (SEQ ID NO: 31) | SGGYNGHYG (SEQ ID NO: 19) | WYQQKPGQ SPVLVIY (SEQ ID NO: 32) | SNNQRPS (SEQ ID NO: 21) | NIPERFSGSTSGSTST LTISGTQAMDEADYYC (SEQ ID NO: 44) | GGYDSSAGI (SEQ ID NO: 23) | TGTGTKLTVL (SEQ ID NO: 34) |
| F10VL3-21 93% | SYELTQPPSVS VAPGKTARITC (SEQ ID NO: 36) | SGGYNGHYG (SEQ ID NO: 19) | WYQQKPGQ APVLVIY (SEQ ID NO: 26) | SNNQRPS (SEQ ID NO: 21) | NIPERFSGSTSGSTAT LTISRVEAGDEADYYC (SEQ ID NO: 45) | GGYDSSAGI (SEQ ID NO: 23) | FGGGTKLTVL (SEQ ID NO: 29) |
| F10VL3-21L46T CDR3-1 | SYVLTQPPSVS VAPGKTARITC (SEQ ID NO: 46) | SGGYNGHYG (SEQ ID NO: 19) | WYQQKPGQ APVLVIY (SEQ ID NO: 26) | SNNQRPS (SEQ ID NO: 21) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |
| F10VL3-21L46T CDR3-2 | SYVLTQPPSVS VAPGKTARITC (SEQ ID NO: 46) | SGGYNGHYG (SEQ ID NO: 19) | WYQQKPGQ APVTVIY (SEQ ID NO: 30) | SNNQRPS (SEQ ID NO: 21) | GIPERFSGSNSGNTAT LTISRVEAGDEADYYC (SEQ ID NO: 37) | GSTDSNYVGI (SEQ ID NO: 48) | FGGGTKLTVL (SEQ ID NO: 29) |
| F10VL3-21L46T CDR1-GYY | SYVLTQPPSVS VAPGKTARITC (SEQ ID NO: 46) | SGGYNGHYG (SEQ ID NO: 19)YG | WYQQKPGQ APVTVIY (SEQ ID NO: 30) | SNNQRPS (SEQ ID NO: 21) | GIPERFSGSNSGNTAT LTISRVEAGDEADYYC (SEQ ID NO: 37) | GGYDSSAGI (SEQ ID NO: 23) | FGGGTKLTVL (SEQ ID NO: 29) |
| F10VL3-21L46T Hu-VL3-21-CDR1 | SYVLTQPPSVS VAPGKTARITC (SEQ ID NO: 46) | GGNNIGSKSVH (SEQ ID NO: 49) | WYQQKPGQ APVTVIY (SEQ ID NO: 30) | SNNQRPS (SEQ ID NO: 21) | GIPERFSGSNSGNTAT LTISRVEAGDEADYYC (SEQ ID NO: 37) | GGYDSSAGI (SEQ ID NO: 23) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| F10VL3-25L46T Hu-VL3-25-CDR1 | SYELTQPPSVS VSPGQTARITC (SEQ ID NO: 25) | SGDALPKQYAY (SEQ ID NO: 50) | WYQQKPGQ APVTVIY (SEQ ID NO: 30) | SNNQRPS (SEQ ID NO: 21) | GIPERFSGSSSGTTVT LTISGVQAEDEADYYC (SEQ ID NO: 27) | GGYDSSAGI (SEQ ID NO: 23) | FGGGTKLTVL (SEQ ID NO: 29) |
| F10VL3-21L46T CDR3-1-chick | SYVLTQPPSVS VAPGKTARITC (SEQ ID NO: 46) | SGDSSYYGYYG (SEQ ID NO: 51) | WYQQKPGQ APVLVIY (SEQ ID NO: 26) | SNNQRPS (SEQ ID NO: 21) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |
| B9 chicken | ALTQPSSVSA NPGETVKITC (SEQ ID NO: 18) | SGGGSSNYYG (SEQ ID NO: 52) | WYQQKSPG SAPVTLIY (SEQ ID NO: 53) | GTNKRPS (SEQ ID NO: 54) | DIPSRFSGSKSGSTGT LTITGVQADDEAVYFC (SEQ ID NO: 55) | GSADSSTNAGI (SEQ ID NO: 56) | FGAGTTLTVL (SEQ ID NO: 24) |
| B9VL3-25 | SYELTQPPSVS VSPGQTARITC (SEQ ID NO: 25) | SGGGSSNYYG (SEQ ID NO: 52) | WYQQKPGQ APVLVIY (SEQ ID NO: 26) | GTNKRPS (SEQ ID NO: 54) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| B9VL3-25L46T | SYELTQPPSVS VSPGQTARITC (SEQ ID NO: 25) | SGGGSSNYYG (SEQ ID NO: 52) | WYQQKPGQ APVTVIY (SEQ ID NO: 30) | GTNKRPS (SEQ ID NO: 54) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| B9VL3-1 | SYELTQPPSVS VSPGQTASITC (SEQ ID NO: 31) | SGGGSSNYYG (SEQ ID NO: 52) | WYQQKPGQ SPVLVIY (SEQ ID NO: 32) | GTNKRPS (SEQ ID NO: 54) | GIPERFSGSNSGNTAT LTISGTQAMDEADYYC (SEQ ID NO: 33) | GSADSSTNAGI (SEQ ID NO: 56) | TGTGTKLTVL (SEQ ID NO: 34) |
| B9VL3-1L46T | SYELTQPPSVS VSPGQTASITC (SEQ ID NO: 31) | SGGGSSNYYG (SEQ ID NO: 52) | WYQQKPGQ SPVTVIY (SEQ ID NO: 35) | GTNKRPS (SEQ ID NO: 54) | GIPERFSGSNSGNTAT LTISGTQAMDEADYYC (SEQ ID NO: 33) | GSADSSTNAGI (SEQ ID NO: 56) | TGTGTKLTVL (SEQ ID NO: 34) |
| B9VL3-21 | SYVLTQPPSVS VAPGKTARITC (SEQ ID NO: 46) | SGGGSSNYYG (SEQ ID NO: 52) | WYQQKPGQ APVLVIY (SEQ ID NO: 26) | GTNKRPS (SEQ ID NO: 54) | GIPERFSGSNSGNTAT LTISRVEAGDEADYYC (SEQ ID NO: 37) | GSADSSTNAGI (SEQ ID NO: 56) | FGGGTKLTVL (SEQ ID NO: 29) |
| B9VL3-21L46T | SYVLTQPPSVS VAPGKTARITC (SEQ ID NO: 46) | SGGGSSNYYG (SEQ ID NO: 52) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GSADSSTNAGI (SEQ ID NO: 56) | FGGGTKLTVL (SEQ ID NO: 29) |
| B9VL3-19 | SYELTQDPAVS VALGQTVRITC (SEQ ID NO: 38) | SGGGSSNYYG (SEQ ID NO: 52) | WYQQKPGQ APVLVIY (SEQ ID NO: 26) | GTNKRPS (SEQ ID NO: 54) | NIPDRFSGSSSGNTAS LTITGAQAEDEADYYC (SEQ ID NO: 39) | GSADSSTNAGI (SEQ ID NO: 56) | FGSGTKLTVL (SEQ ID NO: 40) |
| B9VL3-19L46T | SYELTQDPAVS VALGQTVRITC (SEQ ID NO: 38) | SGGGSSNYYG (SEQ ID NO: 52) | WYQQKPGQ APVTVIY (SEQ ID NO: 30) | GTNKRPS (SEQ ID NO: 54) | NIPDRFSGSSSGNTAS LTITGAQAEDEADYYC (SEQ ID NO: 39) | GSADSSTNAGI (SEQ ID NO: 56) | FGSGTKLTVL (SEQ ID NO: 40) |
| B9VL3-250.93 | SYELTQPPSVS VSPGQTARITC (SEQ ID NO: 25) | SGGGSSNYYG (SEQ ID NO: 52) | WYQQKPGQ APVTVIY (SEQ ID NO: 30) | GTNKRPS (SEQ ID NO: 54) | NIPERFSGSTSGSTST LTISGVQAEDEADYYC (SEQ ID NO: 41) | GSADSSTNAGI (SEQ ID NO: 56) | FGGGTKLTVL (SEQ ID NO: 29) |
| B9VL3-190.93 | SYELTQDPAVS VALGQTVRITC (SEQ ID NO: 38) | SGGGSSNYYG (SEQ ID NO: 52) | WYQQKPGQ APVTVIY (SEQ ID NO: 30) | GTNKRPS (SEQ ID NO: 54) | NIPDRFSGSTSGSTAS LTITGAQAEDEADYYC (SEQ ID NO: 42) | GSADSSTNAGI (SEQ ID NO: 56) | FGSGTKVTVL (SEQ ID NO: 43) |
| B9VL3-10.93 | SYELTQPPSVS VSPGQTASITC (SEQ ID NO: 31) | SGGGSSNYYG (SEQ ID NO: 52) | WYQQKPGQ SPVLVIY (SEQ ID NO: 32) | GTNKRPS (SEQ ID NO: 54) | NIPERFSGSTSGSTST LTISGTQAMDEADYYC (SEQ ID NO: 44) | GSADSSTNAGI (SEQ ID NO: 56) | TGTGTKLTVL (SEQ ID NO: 34) |
| B9VL3-210.93 | SYVLTQPPSVS VAPGKTARITC (SEQ ID NO: 46) | SGGGSSNYYG (SEQ ID NO: 52) | WYQQKPGQ APVLVIY (SEQ ID NO: 26) | GTNKRPS (SEQ ID NO: 54) | NIPERFSGSTSGSTAT LTISRVEAGDEADYYC (SEQ ID NO: 45) | GSADSSTNAGI (SEQ ID NO: 56) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| B9VL3-21L46T CDR3-1 | SYVLTQPPSVS VAPGKTARITC (SEQ ID NO: 46) | SGGYNGHYG (SEQ ID NO: 19) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |
| B9VL3-21L46T CDR3-2 | SYVLTQPPSVS VAPGKTARITC (SEQ ID NO: 46) | SGGYNGHYG (SEQ ID NO: 19) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GSTDSNYVGI (SEQ ID NO: 48) | FGGGTKLTVL (SEQ ID NO: 29) |
| B9VL3-21L46T CDR1-GYY | SYVLTQPPSVS VAPGKTARITC (SEQ ID NO: 46) | SGGGSSNYYGG (SEQ ID NO: 62) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GSADSSTNAGI (SEQ ID NO: 56) | FGGGTKLTVL (SEQ ID NO: 29) |
| B9VL3-21L46T Hu-VL3-21-CDR1 | SYVLTQPPSVS VAPGKTARITC (SEQ ID NO: 46) | GGNNIGSKSVH (SEQ ID NO: 49) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GSADSSTNAGI (SEQ ID NO: 56) | FGGGTKLTVL (SEQ ID NO: 29) |
| B9VL3-21L46T Hu-VL3-25-CDR1 | SYVLTQPPSVS VAPGKTARITC (SEQ ID NO: 46) | SGDALPKQYAY (SEQ ID NO: 57) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GSADSSTNAGI (SEQ ID NO: 56) | FGGGTKLTVL (SEQ ID NO: 29) |
| B9VL3-21L46T CDR3-1-chick | SYVLTQPPSVS VAPGKTARITC (SEQ ID NO: 46) | SGDSSYYGYYG (SEQ ID NO: 51) | WYQQKPGQ APVTVIY (SEQ ID NO: 30) | GTNKRPS (SEQ ID NO: 54) | GIPERFSGSNSGNTAT LTISRVEAGDEADYYC (SEQ ID NO: 37) | GSADSSTNAGI (SEQ ID NO: 56) | FGGGTKLTVL (SEQ ID NO: 29) |
| C11 chicken | ALTQPSSVSA NPGETVKITC (SEQ ID NO: 18) | SGGGSWY GSYYYG (SEQ ID NO: 58) | WYQQKSPG SAPVTLIY (SEQ ID NO: 53) | NNDKRPS (SEQ ID NO: 60) | DIPSRFSGSESGSTAT LTITGVQAEDEAVYFC (SEQ ID NO: 59) | GGYDSTTTDM (SEQ ID NO: 61) | FGAGTTLTVL (SEQ ID NO: 24) |
| C11VL3-25 | SYELTQPPSVS VSPGQTARITC (SEQ ID NO: 25) | SGGGSWY GSYYYG (SEQ ID NO: 58) | WYQQKPGQ APVLVIY (SEQ ID NO: 26) | NNDKRPS (SEQ ID NO: 60) | GIPERFSGSSSGTTVT LTISGVQAEDEADYYC (SEQ ID NO: 27) | GGYDSTTTDM (SEQ ID NO: 61) | FGGGTKLTVL (SEQ ID NO: 29) |
| C11VL3-25L46T | SYELTQPPSVS VSPGQTARITC (SEQ ID NO: 25) | SGGGSWY GSYYYG (SEQ ID NO: 58) | WYQQKPGQ APVTVIY (SEQ ID NO: 30) | NNDKRPS (SEQ ID NO: 60) | GIPERFSGSSSGTTVT LTISGVQAEDEADYYC (SEQ ID NO: 27) | GGYDSTTTDM (SEQ ID NO: 61) | FGGGTKLTVL (SEQ ID NO: 29) |
| C11VL3-1 | SYELTQPPSVS VSPGQTASITC (SEQ ID NO: 31) | SGGGSWY GSYYYG (SEQ ID NO: 58) | WYQQKPGQ SPVLVIY (SEQ ID NO: 32) | NNDKRPS (SEQ ID NO: 60) | GIPERFSGSNSGNTAT SLTIGTQAMDEADYYC (SEQ ID NO: 33) | GGYDSTTTDM (SEQ ID NO: 61) | TGTGTKLTVL (SEQ ID NO: 34) |
| C11VL3-1L46T | SYELTQPPSVS VSPGQTASITC (SEQ ID NO: 31) | SGGGSWY GSYYYG (SEQ ID NO: 58) | WYQQKPGQ SPVTVIY (SEQ ID NO: 35) | NNDKRPS (SEQ ID NO: 60) | GIPERFSGSNSGNTAT LTISGTQAMDEADYYC (SEQ ID NO: 33) | GGYDSTTTDM (SEQ ID NO: 61) | TGTGTKLTVL (SEQ ID NO: 34) |
| C11VL3-21 | SYVLTQPPSVS VAPGKTARITC (SEQ ID NO: 46) | SGGGSWY GSYYYG (SEQ ID NO: 58) | WYQQKPGQ APVLVIY (SEQ ID NO: 26) | NNDKRPS (SEQ ID NO: 60) | GIPERFSGSNSGNTAT LTISRVEAGDEADYYC (SEQ ID NO: 37) | GGYDSTTTDM (SEQ ID NO: 61) | FGGGTKLTVL (SEQ ID NO: 29) |
| C11VL3-21L46T | SYVLTQPPSVS VAPGKTARITC (SEQ ID NO: 46) | SGGGSWY GSYYYG (SEQ ID NO: 58) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GGYDSTTTDM (SEQ ID NO: 61) | FGGGTKLTVL (SEQ ID NO: 29) |
| C11VL3-19 | SYELTQDPAVS VALGQTVRITC (SEQ ID NO: 38) | SGGGSWY GSYYYG (SEQ ID NO: 58) | WYQQKPGQ APVLVIY (SEQ ID NO: 26) | NNDKRPS (SEQ ID NO: 60) | NIPDRFSGSSSGNTAS LTITGAQAEDEADYYC (SEQ ID NO: 39) | GGYDSTTTDM (SEQ ID NO: 61) | FGSGTKLTVL (SEQ ID NO: 40) |

TABLE 2-continued

| ID | FW1 | LCDR1 | FW2 | LCDR2 | FW3 | LCDR3 | FW4 |
|---|---|---|---|---|---|---|---|
| C11VL3-19L46T | SYELTQDPAVS VALGQTVRITC (SEQ ID NO: 38) | SGGGSWY GSYYYG (SEQ ID NO: 58) | WYQQKPGQ APVTVIY (SEQ ID NO: 30) | NNDKRPS (SEQ ID NO: 60) | NIPDRFSGSSSGNTAS LTITGAQAEDEADYYC (SEQ ID NO: 39) | GGYDSTTTDM (SEQ ID NO: 61) | FGSGTKLTVL (SEQ ID NO: 40) |
| C11VL3-250.93 | SYELTQPPSVS VSPGQTARITC (SEQ ID NO: 25) | SGGGSWY GSYYYG (SEQ ID NO: 58) | WYQQKPGQ APVTVIY (SEQ ID NO: 30) | NNDKRPS (SEQ ID NO: 60) | NIPERFSGSTSGSTST LTISGVQAEDEADYYC (SEQ ID NO: 41) | GGYDSTTTDM (SEQ ID NO: 61) | FGGGTKLTVL (SEQ ID NO: 29) |
| C11VL3-190.93 | SYELTQDPAVS VALGQTVRITC (SEQ ID NO: 38) | SGGGSWY GSYYYG (SEQ ID NO: 58) | WYQQKPGQ APVTVIY (SEQ ID NO: 30) | NNDKRPS (SEQ ID NO: 60) | NIPDRFSGSTSGSTAS LTITGAQAEDEADYYC (SEQ ID NO: 42) | GGYDSTTTDM (SEQ ID NO: 61) | FGSGTKVTVL (SEQ ID NO: 43) |
| C11VL3-10.93 | SYELTQPPSVS VSPGQTASITC (SEQ ID NO: 31) | SGGGSWY GSYYYG (SEQ ID NO: 58) | WYQQKPGQ SPVLVIY (SEQ ID NO: 32) | NNDKRPS (SEQ ID NO: 60) | NIPERFSGSTSGSTST LTISGTQAMDEADYYC (SEQ ID NO: 44) | GGYDSTTTDM (SEQ ID NO: 61) | TGTGTKLTVL (SEQ ID NO: 34) |
| C11VL3-210.93 | SYVLTQPPSVS VAPGKTARITC (SEQ ID NO: 46) | SGGGSWY GSYYYG (SEQ ID NO: 58) | WYQQKPGQ APVLVIY (SEQ ID NO: 26) | NNDKRPS (SEQ ID NO: 60) | NIPERFSGSTSGSTAT LTISRVEAGDEADYYC (SEQ ID NO: 45) | GGYDSTTTDM (SEQ ID NO: 61) | FGGGTKLTVL (SEQ ID NO: 29) |
| C11VL3-21L46T CDR3-1 | SYVLTQPPSVS PVAGKTARITC (SEQ ID NO: 46) | SGGGSWY GSYYYG (SEQ ID NO: 58) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |
| C11VL3-21L46T CDR3-2 | SYVLTQPPSVS VAPGKTARITC (SEQ ID NO: 46) | SGGGSWY GSYYYG (SEQ ID NO: 58) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GSTDSNYVGI (SEQ ID NO: 48) | FGGGTKLTVL (SEQ ID NO: 29) |
| C11VL3-21L46T CDR1-GYY | SYVLTQPPSVS VAPGKTARITC (SEQ ID NO: 46) | SGGGSSNYYGG (SEQ ID NO: 62) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GGYDSTTTDM (SEQ ID NO: 61) | FGGGTKLTVL (SEQ ID NO: 29) |
| C11VL3-21L46T Hu-VL3-21-CDR1 | SYVLTQPPSVS VAPGKTARITC (SEQ ID NO: 46) | GGNNIGSKSVH (SEQ ID NO: 49) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GGYDSTTTDM (SEQ ID NO: 61) | FGGGTKLTVL (SEQ ID NO: 29) |
| C11VL3-21L46T Hu-VL3-25-CDR1 | SYVLTQPPSVS VAPGKTARITC (SEQ ID NO: 46) | SGDALPKQYAY (SEQ ID NO: 57) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GGYDSTTTDM (SEQ ID NO: 61) | FGGGTKLTVL (SEQ ID NO: 29) |
| C11VL3-21L46T CDR3-1-chick | SYVLTQPPSVS VAPGKTARITC (SEQ ID NO: 46) | SGDSSYYGYYG (SEQ ID NO: 51) | WYQQKPGQ APVTVIY (SEQ ID NO: 30) | NNDKRPS (SEQ ID NO: 60) | GIPERFSGSNSGNTAT LTISRVEAGDEADYYC (SEQ ID NO: 37) | GGYDSTTTDM (SEQ ID NO: 61) | FGGGTKLTVL (SEQ ID NO: 29) |
| D3 chicken | ALTQPSSVSA NPGETVKITC (SEQ ID NO: 18) | SGDDRWYG (SEQ ID NO: 63) | WYQQKSPG SAPVTLIY (SEQ ID NO: 53) | SNDKRPS (SEQ ID NO: 64) | DIPSRFSGSKSGSTGT LTITGVQADDEAVYFC (SEQ ID NO: 55) | GSRDSSYAGI (SEQ ID NO: 65) | FGAGTTLTVL (SEQ ID NO: 24) |
| D3VL3-25 | SYELTQPPSVS VSPGQTARITC (SEQ ID NO: 25) | SGDDRWYG (SEQ ID NO: 63) | WYQQKPGQ APVLVIY (SEQ ID NO: 26) | SNDKRPS (SEQ ID NO: 64) | GIPERFSGSSSGTTVT LTISGVQAEDEADYYC (SEQ ID NO: 27) | GSRDSSYAGI (SEQ ID NO: 65) | FGGGTKLTVL (SEQ ID NO: 29) |
| D3VL3-25L46T | SYELTQPPSVS VSPGQTARITC (SEQ ID NO: 25) | SGDDRWYG (SEQ ID NO: 63) | WYQQKPGQ APVTVIY (SEQ ID NO: 30) | SNDKRPS (SEQ ID NO: 64) | GIPERFSGSSSGTTVT LTISGVQAEDEADYYC (SEQ ID NO: 27) | GSRDSSYAGI (SEQ ID NO: 65) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| D3VL3-1 | SYELTQPPSVS VSPGQTASITC (SEQ ID NO: 31) | SGDDRWYG (SEQ ID NO: 63) | WYQQKPGQ SPVLVIY (SEQ ID NO: 32) | SNDKRPS (SEQ ID NO: 64) | GIPERFSGSNSGNTAT LTISGTQAMDEADYYC (SEQ ID NO: 33) | GSRDSSYAGI (SEQ ID NO: 65) | TGTGTKLTVL (SEQ ID NO: 34) |
| D3VL3-1L46T | SYELTQPPSVS VSPGQTASITC (SEQ ID NO: 31) | SGDDRWYG (SEQ ID NO: 63) | WYQQKPGQ SPVTVIY (SEQ ID NO: 35) | SNDKRPS (SEQ ID NO: 64) | GIPERFSGSNSGNTAT LTISGTQAMDEADYYC (SEQ ID NO: 33) | GSRDSSYAGI (SEQ ID NO: 65) | TGTGTKLTVL (SEQ ID NO: 34) |
| D3VL3-21 | SYVLTQPPSVS VAPGKTARITC (SEQ ID NO: 46) | SGDDRWYG (SEQ ID NO: 63) | WYQQKPGQ APVLVIY (SEQ ID NO: 26) | SNDKRPS (SEQ ID NO: 64) | GIPERFSGSNSGNTAT LTISRVEAGDEADYYC (SEQ ID NO: 37) | GSRDSSYAGI (SEQ ID NO: 65) | FGGGTKLTVL (SEQ ID NO: 29) |
| D3VL3-21L46T | SYVLTQPPSVS VAPGKTARITC (SEQ ID NO: 46) | SGDDRWYG (SEQ ID NO: 63) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSRDSSYAGI (SEQ ID NO: 65) | FGGGTKLTVL (SEQ ID NO: 29) |
| D3VL3-19 | SYELTQDPAVS VALGQTVRITC (SEQ ID NO: 38) | SGDDRWYG (SEQ ID NO: 63) | WYQQKPGQ APVLVIY (SEQ ID NO: 26) | SNDKRPS (SEQ ID NO: 64) | NIPDRFSGSSSGNTAS LTITGAQAEDEADYYC (SEQ ID NO: 39) | GSRDSSYAGI (SEQ ID NO: 65) | FGSGTKLTVL (SEQ ID NO: 40) |
| D3VL3-19L46T | SYELTQDPAVS VALGQTVRITC (SEQ ID NO: 38) | SGDDRWYG (SEQ ID NO: 63) | WYQQKPGQ APVTVIY (SEQ ID NO: 30) | SNDKRPS (SEQ ID NO: 64) | NIPDRFSGSSSGNTAS LTITGAQAEDEADYYC (SEQ ID NO: 39) | GSRDSSYAGI (SEQ ID NO: 65) | FGSGTKLTVL (SEQ ID NO: 40) |
| D3VL3-250.93 | SYELTQPPSVS VSPGQTARITC (SEQ ID NO: 25) | SGDDRWYG (SEQ ID NO: 63) | WYQQKPGQ APVTVIY (SEQ ID NO: 30) | SNDKRPS (SEQ ID NO: 64) | NIPERFSGSTSGSTST LTISGVQAEDEADYYC (SEQ ID NO: 41) | GSRDSSYAGI (SEQ ID NO: 65) | FGGGTKLTVL (SEQ ID NO: 29) |
| D3VL3-190.93 | SYELTQDPAVS VALGQTVRITC (SEQ ID NO: 38) | SGDDRWYG (SEQ ID NO: 63) | WYQQKPGQ APVTVIY (SEQ ID NO: 30) | SNDKRPS (SEQ ID NO: 64) | NIPDRFSGSTSGSTAS LTITGAQAEDEADYYC (SEQ ID NO: 42) | GSRDSSYAGI (SEQ ID NO: 65) | FGSGTKVTVL (SEQ ID NO: 43) |
| D3VL3-10.93 | SYELTQPPSVS VSPGQTASITC (SEQ ID NO: 31) | SGDDRWYG (SEQ ID NO: 63) | WYQQKPGQ SPVLVIY (SEQ ID NO: 32) | SNDKRPS (SEQ ID NO: 64) | NIPERFSGSTSGSTST LTISGTQAMDEADYYC (SEQ ID NO: 44) | GSRDSSYAGI (SEQ ID NO: 65) | TGTGTKLTVL (SEQ ID NO: 34) |
| D3VL3-210.93 | SYVLTQPPSVS VAPGKTARITC (SEQ ID NO: 46) | SGDDRWYG (SEQ ID NO: 63) | WYQQKPGQ APVLVIY (SEQ ID NO: 26) | SNDKRPS (SEQ ID NO: 64) | NIPERFSGSTSGSTAT LTISRVEAGDEADYYC (SEQ ID NO: 45) | GSRDSSYAGI (SEQ ID NO: 65) | FGGGTKLTVL (SEQ ID NO: 29) |
| D3VL3-21L46T CDR3-1 | SYVLTQPPSVS VAPGKTARITC (SEQ ID NO: 46) | SGDDRWYG (SEQ ID NO: 63) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |
| D3VL3-21L46T CDR3-2 | SYVLTQPPSVS VAPGKTARITC (SEQ ID NO: 46) | SGDDRWYG (SEQ ID NO: 63) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSTDSNYVGI (SEQ ID NO: 48) | FGGGTKLTVL (SEQ ID NO: 29) |
| D3VL3-21L46T CDR1-GYY | SYVLTQPPSVS VAPGKTARITC (SEQ ID NO: 46) | SGDDRWYG YYG (SEQ ID NO: 63) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSRDSSYAGI (SEQ ID NO: 65) | FGGGTKLTVL (SEQ ID NO: 29) |
| D3VL3-21L46T Hu-VL3-21-CDR1 | SYVLTQPPSVS VAPGKTARITC (SEQ ID NO: 46) | GGNNIGSKSVH (SEQ ID NO: 49) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSRDSSYAGI (SEQ ID NO: 65) | FGGGTKLTVL (SEQ ID NO: 29) |
| D3VL3-21L46T Hu-VL3-25-CDR1 | SYVLTQPPSVS VAPGKTARITC (SEQ ID NO: 46) | SGDALPKQYAY (SEQ ID NO: 57) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSRDSSYAGI (SEQ ID NO: 65) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| D3VL3-21L46T CDR3-1-chick | SYVLTQPPSVS VAPGKTARITC (SEQ ID NO: 46) | SGDSSYYGYYG (SEQ ID NO: 51) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSRDSSYAGI (SEQ ID NO: 65) | FGGGTKLTVL (SEQ ID NO: 29) |
| E1 chicken | ALTQPSSVSA NPGETVKITC (SEQ ID NO: 18) | SGSSGSGYYG (SEQ ID NO: 66) | WYQQKSPG SAPVTLIY (SEQ ID NO: 53) | DNDKRPS (SEQ ID NO: 67) | DIPSRFSGSKSGSTGT LTITGVQADDEAVYFC (SEQ ID NO: 55) | GSADNNYTGI (SEQ ID NO: 68) | FGAGTTLTVL (SEQ ID NO: 24) |
| E1VL3-25 | SYELTQPPSVS VSPGQTARITC (SEQ ID NO: 25) | SGSSGSGYYG (SEQ ID NO: 66) | WYQQKPGQ APVLVIY (SEQ ID NO: 26) | DNDKRPS (SEQ ID NO: 67) | GIPERFSGSSSGTTVT LTISGVQAEDEADYYC (SEQ ID NO: 27) | GSADNNYTGI (SEQ ID NO: 68) | FGGGTKLTVL (SEQ ID NO: 29) |
| E1VL3-25L46T | SYELTQPPSVS VSPGQTARITC (SEQ ID NO: 25) | SGSSGSGYYG (SEQ ID NO: 66) | WYQQKPGQ APVTVIY (SEQ ID NO: 30) | DNDKRPS (SEQ ID NO: 67) | GIPERFSGSSSGTTVT LTISGVQAEDEADYYC (SEQ ID NO: 27) | GSADNNYTGI (SEQ ID NO: 68) | FGGGTKLTVL (SEQ ID NO: 29) |
| E1VL3-1 | SYELTQPPSVS VSPGQTASITC (SEQ ID NO: 31) | SGSSGSGYYG (SEQ ID NO: 66) | WYQQKPGQ SPVLVIY (SEQ ID NO: 32) | DNDKRPS (SEQ ID NO: 67) | GIPERFSGSNSGNTAT LTISGTQAMDEADYYC (SEQ ID NO: 33) | GSADNNYTGI (SEQ ID NO: 68) | TGTGTKLTVL (SEQ ID NO: 34) |
| E1VL3-1L46T | SYELTQPPSVS VSPGQTASITC (SEQ ID NO: 31) | SGSSGSGYYG (SEQ ID NO: 66) | WYQQKPGQ SPVTVIY (SEQ ID NO: 35) | DNDKRPS (SEQ ID NO: 67) | GIPERFSGSNSGNTAT LTISGTQAMDEADYYC (SEQ ID NO: 33) | GSADNNYTGI (SEQ ID NO: 68) | TGTGTKLTVL (SEQ ID NO: 34) |
| E1VL3-21 | SYVLTQPPSVS VAPGKTARITC (SEQ ID NO: 46) | SGSSGSGYYG (SEQ ID NO: 66) | WYQQKPGQ APVLVIY (SEQ ID NO: 26) | DNDKRPS (SEQ ID NO: 67) | GIPERFSGSNSGNTAT LTISRVEAGDEADYYC (SEQ ID NO: 37) | GSADNNYTGI (SEQ ID NO: 68) | FGGGTKLTVL (SEQ ID NO: 29) |
| E1VL3-21L46T | SYVLTQPPSVS VAPGKTARITC (SEQ ID NO: 46) | SGSSGSGYYG (SEQ ID NO: 66) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GSADNNYTGI (SEQ ID NO: 68) | FGGGTKLTVL (SEQ ID NO: 29) |
| E1VL3-19 | SYELTQDPAVS VALGQTVRITC (SEQ ID NO: 38) | SGSSGSGYYG (SEQ ID NO: 66) | WYQQKPGQ APVLVIY (SEQ ID NO: 26) | DNDKRPS (SEQ ID NO: 67) | NIPDRFSGSSSGNTAS LTITGAQAEDEADYYC (SEQ ID NO: 39) | GSADNNYTGI (SEQ ID NO: 68) | FGSGTKLTVL (SEQ ID NO: 40) |
| E1VL3-19L46T | SYELTQDPAVS VALGQTVRITC (SEQ ID NO: 38) | SGSSGSGYYG (SEQ ID NO: 66) | WYQQKPGQ APVTVIY (SEQ ID NO: 30) | DNDKRPS (SEQ ID NO: 67) | NIPDRFSGSSSGNTAS LTITGAQAEDEADYYC (SEQ ID NO: 39) | GSADNNYTGI (SEQ ID NO: 68) | FGSGTKLTVL (SEQ ID NO: 40) |
| E1VL3-250.93 | SYELTQPPSVS VSPGQTARITC (SEQ ID NO: 25) | SGSSGSGYYG (SEQ ID NO: 66) | WYQQKPGQ APVTVIY (SEQ ID NO: 30) | DNDKRPS (SEQ ID NO: 67) | NIPERFSGSTSGSTST LTISGVQAEDEADYYC (SEQ ID NO: 41) | GSADNNYTGI (SEQ ID NO: 68) | FGGGTKLTVL (SEQ ID NO: 29) |
| E1VL3-190.93 | SYELTQDPAVS VALGQTVRITC (SEQ ID NO: 38) | SGSSGSGYYG (SEQ ID NO: 66) | WYQQKPGQ APVTVIY (SEQ ID NO: 30) | DNDKRPS (SEQ ID NO: 67) | NIPDRFSGSTSGSTAS LTITGAQAEDEADYYC (SEQ ID NO: 42) | GSADNNYTGI (SEQ ID NO: 68) | FGSGTKVTVL (SEQ ID NO: 43) |
| E1VL3-10.93 | SYELTQPPSVS VSPGQTASITC (SEQ ID NO: 31) | SGSSGSGYYG (SEQ ID NO: 66) | WYQQKPGQ SPVLVIY (SEQ ID NO: 32) | DNDKRPS (SEQ ID NO: 67) | NIPERFSGSTSGSTST LTISGTQAMDEADYYC (SEQ ID NO: 44) | GSADNNYTGI (SEQ ID NO: 68) | TGTGTKLTVL (SEQ ID NO: 34) |
| E1VL3-210.93 | SYVLTQPPSVS VAPGKTARITC (SEQ ID NO: 46) | SGSSGSGYYG (SEQ ID NO: 66) | WYQQKPGQ APVLVIY (SEQ ID NO: 26) | DNDKRPS (SEQ ID NO: 67) | NIPERFSGSTSGSTAT LTISRVEAGDEADYYC (SEQ ID NO: 45) | GSADNNYTGI (SEQ ID NO: 68) | FGGGTKLTVL (SEQ ID NO: 29) |
| E1VL3-21L46T CDR3-1 | SYVLTQPPSVS VAPGKTARITC (SEQ ID NO: 46) | SGSSGSGYYG (SEQ ID NO: 66) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| E1VL3-21L46T CDR3-2 | SYVLTQPPSVS VAPGKTARITC (SEQ ID NO: 46) | SGSSGSGYYG (SEQ ID NO: 66) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GSTDSNYVGI (SEQ ID NO: 48) | FGGGTKLTVL (SEQ ID NO: 29) |
| E1VL3-21L46T CDR1-GYY | SYVLTQPPSVS VAPGKTARITC (SEQ ID NO: 46) | SGSSGSGYYGG (SEQ ID NO: 69) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GSADNNYTGI (SEQ ID NO: 68) | FGGGTKLTVL (SEQ ID NO: 29) |
| E1VL3-21L46T Hu-VL3-21-CDR1 | SYVLTQPPSVS VAPGKTARITC (SEQ ID NO: 46) | GGNNIGSKSVH (SEQ ID NO: 49) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GSADNNYTGI (SEQ ID NO: 68) | FGGGTKLTVL (SEQ ID NO: 29) |
| E1VL3-21L46T Hu-VL3-25-CDR1 | SYVLTQPPSVS VAPGKTARITC (SEQ ID NO: 46) | SGDALPKQYAY (SEQ ID NO: 57) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GSADNNYTGI (SEQ ID NO: 68) | FGGGTKLTVL (SEQ ID NO: 29) |
| E1VL3-21L46T CDR3-1-chick | SYVLTQPPSVS VAPGKTARITC (SEQ ID NO: 46) | SGDSSYYGYYG (SEQ ID NO: 51) | WYQQKPGQ APVTVIY (SEQ ID NO: 30) | DNDKRPS (SEQ ID NO: 67) | GIPERFSGSNSGNTAT LTISRVEAGDEADYYC (SEQ ID NO: 37) | GSADNNYTGI (SEQ ID NO: 68) | FGGGTKLTVL (SEQ ID NO: 29) |
| N5_B4VL3-25 | SYELTQPPSVS VSPGQTARITC (SEQ ID NO: 25) | SGGSGSYGYYG (SEQ ID NO: 70) | WYQQKPGQ APVLVIY (SEQ ID NO: 26) | SNNQRPS (SEQ ID NO: 21) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| N5_B7VL3-25 | SYELTQPPSVS VSPGQTARITC (SEQ ID NO: 25) | SGGSGSYGYYG (SEQ ID NO: 70) | WYQQKPGQ APVLVIY (SEQ ID NO: 26) | GTNKRPS (SEQ ID NO: 54) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| N6_C5VL3-25 | SYELTQPPSVS VSPGQTARITC (SEQ ID NO: 25) | SGGYNGHYG (SEQ ID NO: 19) | WYQQKPGQ APVLVIY (SEQ ID NO: 26) | SNNQRPS (SEQ ID NO: 21) | GIPERFSGSSSGTTVT LTISGVQAEDEADYYC (SEQ ID NO: 27) | GNADSNYVGI (SEQ ID NO: 47) | FGGGTKLTVL (SEQ ID NO: 29) |
| N6_F11VL3-25 | SYELTQPPSVS VSPGQTARITC (SEQ ID NO: 25) | SGGGSSNYYG (SEQ ID NO: 52) | WYQQKPGQ APVLVIY (SEQ ID NO: 26) | SNNQRPS (SEQ ID NO: 21) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| N6_G3VL3-25 | SYELTQPPSVS VSPGQTARITC (SEQ ID NO: 25) | SGGSGSYGYYG (SEQ ID NO: 70) | WYQQKPGQ APVLVIY (SEQ ID NO: 26) | GTNKRPS (SEQ ID NO: 54) | GIPERFSGSSSGTTVT LTISGVQAEDEADYYC (SEQ ID NO: 27) | GSTDSNYVGI (SEQ ID NO: 48) | FGGGTKLTVL (SEQ ID NO: 29) |
| N5_B4VL3-25L46T | SYELTQPPSVS VSPGQTARITC (SEQ ID NO: 25) | SGGSGSYGYYG (SEQ ID NO: 70) | WYQQKPGQ APVTVIY (SEQ ID NO: 30) | SNNQRPS (SEQ ID NO: 21) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| N5_B7VL3-25L46T | SYELTQPPSVS VSPGQTARITC (SEQ ID NO: 25) | SGGSGSYGYYG (SEQ ID NO: 70) | WYQQKPGQ APVTVIY (SEQ ID NO: 30) | GTNKRPS (SEQ ID NO: 54) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |
| N6_C5VL3-25L46T | SYELTQPPSVS VSPGQTARITC (SEQ ID NO: 25) | SGGYNGHYG (SEQ ID NO: 19) | WYQQKPGQ APVTVIY (SEQ ID NO: 30) | SNNQRPS (SEQ ID NO: 21) | GIPERFSGSSSGTTVT LTISGVQAEDEADYYC (SEQ ID NO: 27) | GNADSNYVGI (SEQ ID NO: 47) | FGGGTKLTVL (SEQ ID NO: 29) |
| N6_F11VL3-25L46T | SYELTQPPSVS VSPGQTARITC (SEQ ID NO: 25) | SGGGSSNYYG (SEQ ID NO: 52) | WYQQKPGQ APVTVIY (SEQ ID NO: 30) | SNNQRPS (SEQ ID NO: 21) | GIPERFSGSSSGTTVT LTISGVQAEDEADYYC (SEQ ID NO: 27) | GSADSSTNAGI (SEQ ID NO: 56) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| N6_G3VL3-25L46T | SYELTQPPSVSVSPGQTARITC (SEQ ID NO: 25) | SGGSGSYGYYG (SEQ ID NO: 70) | WYQQKPGQAPVTVIY (SEQ ID NO: 30) | GTNKRPS (SEQ ID NO: 54) | GIPERFSGSSSGTTVTLTISGVQAEDEADYYC (SEQ ID NO: 27) | GSTDSNYVGI (SEQ ID NO: 48) | FGGGTKLTVL (SEQ ID NO: 29) |
| N5_B4VL3-21 | SYVLTQPPSVSVAPGKTARITC (SEQ ID NO: 46) | SGGSGSYGYYG (SEQ ID NO: 70) | WYQQKPGQAPVLVIY (SEQ ID NO: 26) | SNNQRPS (SEQ ID NO: 21) | GIPERFSGSNSGNTATLTISRVEAGDEADYYC (SEQ ID NO: 37) | GSADSSTNAGI (SEQ ID NO: 56) | FGGGTKLTVL (SEQ ID NO: 29) |
| N5_B7VL3-21 | SYVLTQPPSVSVAPGKTARITC (SEQ ID NO: 46) | SGGSGSYGYYG (SEQ ID NO: 70) | WYQQKPGQAPVLVIY (SEQ ID NO: 26) | GTNKRPS (SEQ ID NO: 54) | GIPERFSGSNSGNTATLTISRVEAGDEADYYC (SEQ ID NO: 37) | GSADSSTNAGI (SEQ ID NO: 56) | FGGGTKLTVL (SEQ ID NO: 29) |
| N6_C5VL3-21 | SYVLTQPPSVSVAPGKTARITC (SEQ ID NO: 46) | SGGYNGHYG (SEQ ID NO: 19) | WYQQKPGQAPVLVIY (SEQ ID NO: 26) | SNNQRPS (SEQ ID NO: 21) | GIPERFSGSNSGNTATLTISRVEAGDEADYYC (SEQ ID NO: 37) | GNADSNYVGI (SEQ ID NO: 47) | FGGGTKLTVL (SEQ ID NO: 29) |
| N6_F11VL3-21 | SYVLTQPPSVSVAPGKTARITC (SEQ ID NO: 46) | SGGGSSNYYG (SEQ ID NO: 52) | WYQQKPGQAPVLVIY (SEQ ID NO: 26) | SNNQRPS (SEQ ID NO: 21) | GIPERFSGSNSGNTATLTISRVEAGDEADYYC (SEQ ID NO: 37) | GSADSSTNAGI (SEQ ID NO: 56) | FGGGTKLTVL (SEQ ID NO: 29) |
| N6_G3VL3-21 | SYVLTQPPSVSVAPGKTARITC (SEQ ID NO: 46) | SGGSGSYGYYG (SEQ ID NO: 70) | WYQQKPGQAPVLVIY (SEQ ID NO: 26) | GTNKRPS (SEQ ID NO: 54) | GIPERFSGSNSGNTATLTISRVEAGDEADYYC (SEQ ID NO: 37) | GSTDSNYVGI (SEQ ID NO: 48) | FGGGTKLTVL (SEQ ID NO: 29) |
| N5_B4VL3-21L46T | SYVLTQPPSVSVAPGKTARITC (SEQ ID NO: 46) | SGGSGSYGYYG (SEQ ID NO: 70) | WYQQKPGQAPVTVIY (SEQ ID NO: 30) | SNNQRPS (SEQ ID NO: 21) | GIPERFSGSNSGNTATLTISRVEAGDEADYYC (SEQ ID NO: 37) | GSADSSTNAGI (SEQ ID NO: 56) | FGGGTKLTVL (SEQ ID NO: 29) |
| N5_B7VL3-21L46T | SYVLTQPPSVSVAPGKTARITC (SEQ ID NO: 46) | SGGSGSYGYYG (SEQ ID NO: 70) | WYQQKPGQAPVTVIY (SEQ ID NO: 30) | GTNKRPS (SEQ ID NO: 54) | GIPERFSGSNSGNTATLTISRVEAGDEADYYC (SEQ ID NO: 37) | GSADSSTNAGI (SEQ ID NO: 56) | FGGGTKLTVL (SEQ ID NO: 29) |
| N6_C5VL3-21L46T | SYVLTQPPSVSVAPGKTARITC (SEQ ID NO: 46) | SGGYNGHYG (SEQ ID NO: 19) | WYQQKPGQAPVTVIY (SEQ ID NO: 30) | SNNQRPS (SEQ ID NO: 21) | GIPERFSGSNSGNTATLTISRVEAGDEADYYC (SEQ ID NO: 37) | GNADSNYVGI (SEQ ID NO: 47) | FGGGTKLTVL (SEQ ID NO: 29) |
| N6_F11VL3-21L46T | SYVLTQPPSVSVAPGKTARITC (SEQ ID NO: 46) | SGGGSSNYYG (SEQ ID NO: 52) | WYQQKPGQAPVTVIY (SEQ ID NO: 30) | SNNQRPS (SEQ ID NO: 21) | GIPERFSGSNSGNTATLTISRVEAGDEADYYC (SEQ ID NO: 37) | GSADSSTNAGI (SEQ ID NO: 56) | FGGGTKLTVL (SEQ ID NO: 29) |
| N6_G3VL3-21L46T | SYVLTQPPSVSVAPGKTARITC (SEQ ID NO: 46) | SGGSGSYGYYG (SEQ ID NO: 70) | WYQQKPGQAPVTVIY (SEQ ID NO: 30) | GTNKRPS (SEQ ID NO: 54) | GIPERFSGSNSGNTATLTISRVEAGDEADYYC (SEQ ID NO: 37) | GSTDSNYVGI (SEQ ID NO: 48) | FGGGTKLTVL (SEQ ID NO: 29) |
| A1 chicken | ALTQPSSVSANPGETVKITC (SEQ ID NO: 18) | SGGSGSYG (SEQ ID NO: 84) | WYQQKSPGSAPVTVIY (SEQ ID NO: 20) | SNDKRPS (SEQ ID NO: 22) | NIPSRFSGSTSGSTSTLTITGVRAEDEAVYFC (SEQ ID NO: 73) | GSADSSSTAGI (SEQ ID NO: 24) | FGAGTTLTVL |
| A1VL3-25 | SYELTQPPSVSVSPGQTARITC (SEQ ID NO: 25) | SGGSGSYG (SEQ ID NO: 84) | WYQQKPGQAPVLVIY (SEQ ID NO: 26) | SNDKRPS (SEQ ID NO: 64) | GIPERFSGSSSGTTVTLTISGVQAEDEADYYC (SEQ ID NO: 27) | GSADSSSTAGI (SEQ ID NO: 73) | FGGGTKLTVL (SEQ ID NO: 29) |
| A1VL3-25L46T | SYELTQPPSVSVSPGQTARITC (SEQ ID NO: 25) | SGGSGSYG (SEQ ID NO: 84) | WYQQKPGQAPVTVIY (SEQ ID NO: 30) | SNDKRPS (SEQ ID NO: 64) | GIPERFSGSSSGTTVTLTISGVQAEDEADYYC (SEQ ID NO: 27) | GSADSSSTAGI (SEQ ID NO: 73) | FGGGTKLTVL (SEQ ID NO: 29) |
| A1VL3-1 | SYELTQPPSVSVSPGQTASITC (SEQ ID NO: 31) | SGGSGSYG (SEQ ID NO: 84) | WYQQKPGQSPVLVIY (SEQ ID NO: 32) | SNDKRPS (SEQ ID NO: 64) | GIPERFSGSNSGNTATLTISGTQAMDEADYYC (SEQ ID NO: 33) | GSADSSSTAGI (SEQ ID NO: 73) | TGTGTKLTVL (SEQ ID NO: 34) |

TABLE 2-continued

| ID | FW1 | LCDR1 | FW2 | LCDR2 | FW3 | LCDR3 | FW4 |
|---|---|---|---|---|---|---|---|
| A1VL3-1L46T | SYELTQPPSVS VSPGQTASITC (SEQ ID NO: 31) | SGGSGSYG (SEQ ID NO: 84) | WYQQKPGQ SPVTVIY (SEQ ID NO: 35) | SNDKRPS (SEQ ID NO: 64) | GIPERFSGSNSGNTAT LTISGTQAMDEADYYC (SEQ ID NO: 33) | GSADSSSTAGI (SEQ ID NO: 73) | TGTGTKLTVL (SEQ ID NO: 34) |
| A1VL3-21 | SYVLTQPPSVS VAPGKTARITC (SEQ ID NO: 46) | SGGSGSYG (SEQ ID NO: 84) | WYQQKPGQ APVLVIY (SEQ ID NO: 26) | SNDKRPS (SEQ ID NO: 64) | GIPERFSGSNSGNTAT LTISRVEAGDEADYYC (SEQ ID NO: 37) | GSADSSSTAGI (SEQ ID NO: 73) | FGGGTKLTVL (SEQ ID NO: 29) |
| A1VL3-21L46T | SYVLTQPPSVS VAPGKTARITC (SEQ ID NO: 46) | SGGSGSYG (SEQ ID NO: 84) | WYQQKPGQ APVTVIY (SEQ ID NO: 30) | SNDKRPS (SEQ ID NO: 64) | GIPERFSGSNSGNTAT LTISRVEAGDEADYYC SEQ ID NO: 37) | GSADSSSTAGI (SEQ ID NO: 73) | FGGGTKLTVL (SEQ ID NO: 29) |
| A1VL3-19 | SYELTQDPAVS VALGQTVRITC (SEQ ID NO: 38) | SGGSGSYG (SEQ ID NO: 84) | WYQQKPGQ APVLVIY (SEQ ID NO: 26) | SNDKRPS (SEQ ID NO: 64) | NIPDRFSGSSSGNTAS LTITGAQAEDEADYYC (SEQ ID NO: 39) | GSADSSSTAGI (SEQ ID NO: 73) | FGSGTKLTVL (SEQ ID NO: 40) |
| A1VL3-19L46T | SYELTQDPAVS VALGQTVRITC (SEQ ID NO: 38) | SGGSGSYG (SEQ ID NO: 84) | WYQQKPGQ APVTVIY (SEQ ID NO: 30) | SNDKRPS (SEQ ID NO: 64) | NIPDRFSGSSSGNTAS LTITGAQAEDEADYYC (SEQ ID NO: 39) | GSADSSSTAGI (SEQ ID NO: 73) | FGSGTKLTVL (SEQ ID NO: 40) |
| A1VL3-250.93 | SYELTQPPSVS VSPGQTARITC (SEQ ID NO: 25) | SGGSGSYG (SEQ ID NO: 84) | WYQQKPGQ APVTVIY (SEQ ID NO: 30) | SNDKRPS (SEQ ID NO: 64) | NIPERFSGSTSGSTST LTISGVQAEDEADYYC (SEQ ID NO: 41) | GSADSSSTAGI (SEQ ID NO: 73) | FGGGTKLTVL (SEQ ID NO: 29) |
| A1VL3-190.93 | SYELTQDPAVS VALGQTVRITC (SEQ ID NO: 38) | SGGSGSYG (SEQ ID NO: 84) | WYQQKPGQ APVTVIY (SEQ ID NO: 30) | SNDKRPS (SEQ ID NO: 64) | NIPDRFSGSTSGSTAS LTITGAQAEDEADYYC (SEQ ID NO: 42) | GSADSSSTAGI (SEQ ID NO: 73) | FGSGTKVTVL (SEQ ID NO: 43) |
| A1VL3-10.93 | SYELTQPPSVS VSPGQTASITC (SEQ ID NO: 31) | SGGSGSYG (SEQ ID NO: 84) | WYQQKPGQ SPVLVIY (SEQ ID NO: 32) | SNDKRPS (SEQ ID NO: 64) | NIPERFSGSTSGSTST LTISGTQAMDEADYYC (SEQ ID NO: 44) | GSADSSSTAGI (SEQ ID NO: 73) | TGTGTKLTVL (SEQ ID NO: 34) |
| A1VL3-210.93 | SYVLTQPPSVS VAPGKTARITC (SEQ ID NO: 46) | SGGSGSYG (SEQ ID NO: 84) | WYQQKPGQ APVLVIY (SEQ ID NO: 26) | SNDKRPS (SEQ ID NO: 64) | NIPERFSGSTSGSTAT LTISRVEAGDEADYYC (SEQ ID NO: 45) | GSADSSSTAGI (SEQ ID NO: 73) | FGGGTKLTVL (SEQ ID NO: 29) |
| A1VL3-21L46T CDR3-1 | SYVLTQPPSVS VAPGKTARITC (SEQ ID NO: 46) | SGGSGSYG (SEQ ID NO: 84) | WYQQKPGQ APVLVIY (SEQ ID NO: 26) | SNDKRPS (SEQ ID NO: 64) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |
| A1VL3-21L46T CDR3-2 | SYVLTQPPSVS VAPGKTARITC (SEQ ID NO: 46) | SGGSGSYG (SEQ ID NO: 84) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSTDSNYVGI (SEQ ID NO: 48) | FGGGTKLTVL (SEQ ID NO: 29) |
| A1VL3-21L46T CDR1-GYY | SYVLTQPPSVS VAPGKTARITC (SEQ ID NO: 46) | SGGSGSYGYYG (SEQ ID NO: 70) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSADSSSTAGI (SEQ ID NO: 73) | FGGGTKLTVL (SEQ ID NO: 29) |
| A1VL3-21L46T Hu-VL3-21-CDR1 | SYVLTQPPSVS VAPGKTARITC (SEQ ID NO: 46) | GGNNIGSKSVH (SEQ ID NO: 49) | WYQQKPGQ APVTVIY (SEQ ID NO: 30) | SNDKRPS (SEQ ID NO: 64) | GIPERFSGSNSGNTAT LTISRVEAGDEADYYC (SEQ ID NO: 37) | GSADSSSTAGI (SEQ ID NO: 73) | FGGGTKLTVL (SEQ ID NO: 29) |
| A1VL3-25L46T Hu-VL3-25-CDR1 | SYELTQPPSVS VSPGQTARITC (SEQ ID NO: 25) | SGDALPKQYAY (SEQ ID NO: 57) | WYQQKPGQ APVTVIY (SEQ ID NO: 30) | SNDKRPS (SEQ ID NO: 64) | GIPERFSGSSSGTTVT LTISGVQAEDEADYYC (SEQ ID NO: 27) | GSADSSSTAGI (SEQ ID NO: 73) | FGGGTKLTVL (SEQ ID NO: 29) |

TABLE 2-continued

| ID | FW1 | LCDR1 | FW2 | LCDR2 | FW3 | LCDR3 | FW4 |
|---|---|---|---|---|---|---|---|
| A1VL3-21L46T CDR3-1-chick | SYVLTQPPSVS VAPGKTARITC (SEQ ID NO: 46) | SGGSGSYG (SEQ ID NO: 84) | WYQQKPGQ APVLVIY (SEQ ID NO: 26) | SNDKRPS (SEQ ID NO: 64) | GIPERFSGSNSGNTAT LTISRVEAGDEADYYC (SEQ ID NO: 37) | GNADSNYVGI (SEQ ID NO: 47) | FGGGTKLTVL (SEQ ID NO: 29) |

In some embodiments, the protein or antibody comprises a sequence selected from column FW1 of Table 2, column LCDR1 of Table 2, column FW2 of Table 2, column LCDR2 of Table 2, column FW3 of v, column LCDR3 of v, and column FW4 of Table 2. In some embodiments, the protein or antibody comprises a sequence selected from LCDR1 of Table 2, LCDR2 of v, and LCDR3 of Table 2. As used herein, a LCDR is a CDR present in the light chain of an antibody.

In some embodiments, the protein or antibody comprises a sequence as set forth in Table 3. In some embodiments, the protein or antibody comprises one sequence from column CDR1 of Table 3, one sequence from column CDR2 of Table 3, and/or one sequence from column CDR3 of Table 3.

TABLE 3

| ID | CDR1 | CDR2 | CDR3 |
|---|---|---|---|
| F10 | SGGYNGHYG (SEQ ID NO: 19) | SNNQRPS (SEQ ID NO: 21) | GGYDSSAGI (SEQ ID NO: 23) |
| B9 | SGGGSSNYYG (SEQ ID NO: 52) | GTNKRPS (SEQ ID NO: 54) | GSADSSTNAGI (SEQ ID NO: 56) |
| C11 | SGGGSWYGSYYYG (SEQ ID NO: 58) | NNDKRPS (SEQ ID NO: 60) | GGYDSTTTDM (SEQ ID NO: 61) |
| D3 | SGDDRWYG (SEQ ID NO: 63) | SNDKRPS (SEQ ID NO: 64) | GSRDSSYAGI (SEQ ID NO: 65) |
| E1 | SGSSGSGYYG (SEQ ID NO: 66) | DNDKRPS (SEQ ID NO: 67) | GSADNNYTGI (SEQ ID NO: 68) |
| A1 | SGGSGSYG (SEQ ID NO: 84) | SNDKRPS (SEQ ID NO: 64) | GSADSSSTAGI (SEQ ID NO: 73) |
| Extra CDR3-1 | | | GNADSNYVGI (SEQ ID NO: 47) |
| Extra CDR3-2 | | | GSTDSNYVGI (SEQ ID NO: 48) |
| VL3-21 | GGNNIGSKSVH (SEQ ID NO: 49) | YDSDRPS (SEQ ID NO: 77) | QVWDSSSDHVV (SEQ ID NO: 78) |
| VL3-25 | SGDALPKQYAY (SEQ ID NO: 57) | KDSERPS (SEQ ID NO: 79) | QSADSSGTYV (SEQ ID NO: 80) |
| chicken-germ | SGDSSYYG (SEQ ID NO: 71) | DNTNRPS (SEQ ID NO: 72) | GSADSSSTAGI (SEQ ID NO: 73) |
| F10-GYY | SGGYNGHYGYG (SEQ ID NO: 74) | | |
| B9-GYY | SGGGSSNYYGG (SEQ ID NO: 62) | | |
| C11-GYY | SGGGSWYGSYG (SEQ ID NO: 75) | | |
| D3-GYY | SGDDRWYGYYG (SEQ ID NO: 76) | | |
| E1-GYY | SGSSGSGYYGG (SEQ ID NO: 69) | | |
| A1-GYY | SGGSGSYGYYG (SEQ ID NO: 70) | | |
| chicken-germ-GYY | SGDSSYYGYYG (SEQ ID NO: 51) | | |

In some embodiments, the protein comprises a sequence as set forth in SEQ ID NOs: 18-80.

In some embodiments, the protein or antibody comprises a LCDR1 of SEQ ID NO: 19. In some embodiments, the protein or antibody comprises a LCDR2 of SEQ ID NO: 20. In some embodiments, the protein or antibody comprises a LCDR3 of SEQ ID NO: 23. In some embodiments, the protein or antibody comprises a LCDR1 of SEQ ID NO: 19, a LCDR2 of SEQ ID NO: 21, and a LCDR3 of SEQ ID NO: 23. In some embodiments, the protein comprises, one, two, or each of SEQ ID NO: 19, SEQ ID NO: 21, and SEQ ID NO: 23.

In some embodiments, the protein or antibody comprises a LCDR1 of SEQ ID NO: 52. In some embodiments, the protein or antibody comprises a LCDR2 of SEQ ID NO: 54. In some embodiments, the protein or antibody comprises a LCDR3 of SEQ ID NO: 56. In some embodiments, the protein or antibody comprises a LCDR1 of SEQ ID NO: 52, a LCDR2 of SEQ ID NO: 54, and a LCDR3 of SEQ ID NO: 56. In some embodiments, the protein comprises, one, two, or each of SEQ ID NO: 52, SEQ ID NO: 54, and SEQ ID NO: 56.

In some embodiments, the protein or antibody comprises a LCDR1 of SEQ ID NO: 58. In some embodiments, the protein or antibody comprises a LCDR2 of SEQ ID NO: 60. In some embodiments, the protein or antibody comprises a LCDR3 of SEQ ID NO: 61. In some embodiments, the protein or antibody comprises a LCDR1 of SEQ ID NO: 58, a LCDR2 of SEQ ID NO: 60, and a LCDR3 of SEQ ID NO: 61. In some embodiments, the protein comprises, one, two, or each of SEQ ID NO: 58, SEQ ID NO: 60, and SEQ ID NO: 61.

In some embodiments, the protein or antibody comprises a LCDR1 of SEQ ID NO: 63. In some embodiments, the protein or antibody comprises a LCDR2 of SEQ ID NO: 64. In some embodiments, the protein or antibody comprises a LCDR3 of SEQ ID NO: 65. In some embodiments, the protein or antibody comprises a LCDR1 of SEQ ID NO: 63, a LCDR2 of SEQ ID NO: 64, and a LCDR3 of SEQ ID NO: 66. In some embodiments, the protein comprises, one, two, or each of SEQ ID NO: 63, SEQ ID NO: 64, and SEQ ID NO: 65.

In some embodiments, the protein or antibody comprises a LCDR1 of SEQ ID NO: 66. In some embodiments, the protein or antibody comprises a LCDR2 of SEQ ID NO: 67. In some embodiments, the protein or antibody comprises a LCDR3 of SEQ ID NO: 68. In some embodiments, the protein or antibody comprises a LCDR1 of SEQ ID NO: 66, a LCDR2 of SEQ ID NO: 67, and a LCDR3 of SEQ ID NO: 68. In some embodiments, the protein comprises, one, two, or each of SEQ ID NO: 66, SEQ ID NO: 67, and SEQ ID NO: 68.

In some embodiments, the protein or antibody comprises a first sequence or a first CDR selected from the group consisting of: SEQ ID NOs: 19, 49, 50, 51, 52, 57, 58, 62, 63, 66, 69, 70, 71, 74, 75, and 76; a second sequence or second CDR selected from the group consisting of: 21, 54, 60, 64, 67, 72, 77, and 79; and a third sequence or third CDR selected from the group consisting of: 23, 47, 48, 56, 61, 65, 68, 73, 78, and 80.

In some embodiments, the protein or antibody comprises a first sequence or a first CDR selected from the group consisting of: SEQ ID NOs: 19, 49, 50, 51, 52, 57, 58, 62, 63, 66, 69, and 70; a second sequence or second CDR selected from the group consisting of: 21, 54, 60, 64, and 67; and a third sequence or third CDR selected from the group consisting of: 23, 47, 48, 56, 61, 65, and 68.

In some embodiments, the protein or antibody comprises a protein sequence of SEQ ID NOs: 19, 21, and 23. In some embodiments, the protein or antibody comprises a protein sequence of SEQ ID NOs: 19, 27, and 23. In some embodiments, the protein or antibody comprises a protein sequence of SEQ ID NOs: 18, 21, and 23. In some embodiments, the protein or antibody comprises a protein sequence of SEQ ID NOs: 19, 21, and 47. In some embodiments, the protein or antibody comprises a protein sequence of SEQ ID NOs: 19, 21, and 48. In some embodiments, the protein or antibody comprises a protein sequence of SEQ ID NOs: 49, 21, and 23. In some embodiments, the protein or antibody comprises a protein sequence of SEQ ID NOs: 50, 21, and 23. In some embodiments, the protein or antibody comprises a protein sequence of SEQ ID NOs: 51, 21, and 47.

In some embodiments, the protein or antibody comprises a protein sequence of SEQ ID NOs: 52, 54, and 56. In some embodiments, the protein or antibody comprises a protein sequence of SEQ ID NOs: 19, 54, and 47. In some embodiments, the protein or antibody comprises a protein sequence of SEQ ID NOs: 19, 54, and 48. In some embodiments, the protein or antibody comprises a protein sequence of SEQ ID NOs: 62, 54, and 56. In some embodiments, the protein or antibody comprises a protein sequence of SEQ ID NOs: 49, 54, and 56. In some embodiments, the protein or antibody comprises a protein sequence of SEQ ID NOs: 57, 54, and 56. In some embodiments, the protein or antibody comprises a protein sequence of SEQ ID NOs: 51, 54, and 56. In some embodiments, the protein or antibody comprises a protein sequence of SEQ ID NOs: 58, 60, and 61. In some embodiments, the protein or antibody comprises a protein sequence of SEQ ID NOs: 58, 60, and 47. In some embodiments, the protein or antibody comprises a protein sequence of SEQ ID NOs: 58, 60, and 48. In some embodiments, the protein or antibody comprises a protein sequence of SEQ ID NOs: 62, 60, and 61. In some embodiments, the protein or antibody comprises a protein sequence of SEQ ID NOs: 49, 60, and 61. In some embodiments, the protein or antibody comprises a protein sequence of SEQ ID NOs: 57, 60, and 61. In some embodiments, the protein or antibody comprises a protein sequence of SEQ ID NOs: 51, 60, and 61.

In some embodiments, the protein or antibody comprises a protein sequence of SEQ ID NOs: 63, 64, and 65. In some embodiments, the protein or antibody comprises a protein sequence of SEQ ID NOs: 63, 64, and 47. In some embodiments, the protein or antibody comprises a protein sequence of SEQ ID NOs: 63, 64, and 48. In some embodiments, the protein or antibody comprises a protein sequence of SEQ ID NOs: 49, 64, and 65. In some embodiments, the protein or antibody comprises a protein sequence of SEQ ID NOs: 57, 64, and 65. In some embodiments, the protein or antibody comprises a protein sequence of SEQ ID NOs: 51, 64, and 65.

In some embodiments, the protein or antibody comprises a protein sequence of SEQ ID NOs: 66, 67, and 68. In some embodiments, the protein or antibody comprises a protein sequence of SEQ ID NOs: 66, 67, and 47. In some embodiments, the protein or antibody comprises a protein sequence of SEQ ID NOs: 66, 67, and 48. In some embodiments, the protein or antibody comprises a protein sequence of SEQ ID NOs: 69, 67, and 68. In some embodiments, the protein or antibody comprises a protein sequence of SEQ ID NOs: 49, 67, and 68. In some embodiments, the protein or antibody comprises a protein sequence of SEQ ID NOs: 57, 67, and 68. In some embodiments, the protein or antibody comprises a protein sequence of SEQ ID NOs: 51, 67, and 68.

In some embodiments, the protein or antibody comprises a protein sequence of SEQ ID NOs: 70, 21, and 56. In some embodiments, the protein or antibody comprises a protein sequence of SEQ ID NOs: 70, 54, and 56. In some embodiments, the protein or antibody comprises a protein sequence of SEQ ID NOs: 19, 21, and 47. In some embodiments, the protein or antibody comprises a protein sequence of SEQ ID NOs: 52, 21, and 56. In some embodiments, the protein or antibody comprises a protein sequence of SEQ ID NOs: 70, 54, and 48. In some embodiments, the protein or antibody comprises a protein sequence of SEQ ID NOs: 70, 21, and 56.

In some embodiments, an antibody or antibody $V_L$ chain is provided, wherein the antibody or antibody $V_L$ chain comprises a first CDR, a second CDR and a third CDR. In some embodiments, the antibody or antibody $V_L$ chain comprises a first CDR comprising SEQ ID NO: 19, a second CDR comprising SEQ ID NO: 21, and a third CDR comprising SEQ ID NO: 23. In some embodiments, the antibody or antibody $V_L$ chain comprises a first CDR comprising SEQ ID NO: 19, a second CDR comprising SEQ ID NO: 27, and a third CDR comprising SEQ ID NO: 23. In some embodiments, the antibody or antibody $V_L$ chain comprises a first CDR comprising SEQ ID NO: 18, a second CDR comprising SEQ ID NO: 21, and a third CDR comprising SEQ ID NO: 23. In some embodiments, the antibody or antibody $V_L$ chain comprises a first CDR comprising SEQ ID NO: 19, a second CDR comprising SEQ ID NO: 21, and a third CDR comprising SEQ ID NO: 47. In some embodiments, the antibody or antibody $V_L$ chain comprises a first CDR comprising SEQ ID NO: 19, a second CDR comprising SEQ ID NO: 21, and a third CDR comprising SEQ ID NO: 48. In some embodiments, the antibody or antibody $V_L$ chain comprises a first CDR comprising SEQ ID NO: 49, a second CDR comprising SEQ ID NO: 21, and a third CDR comprising SEQ ID NO: 23. In some embodiments, the antibody or antibody $V_L$ chain comprises a first CDR comprising SEQ ID NO: 50, a second CDR comprising SEQ ID NO: 21, and a third CDR comprising SEQ ID NO: 23. In some embodiments, the antibody or antibody $V_L$ chain comprises a first CDR comprising SEQ ID NO: 51, a second CDR comprising SEQ ID NO: 21, and a third CDR comprising SEQ ID NO: 47.

In some embodiments, the antibody or antibody $V_L$ chain comprises a first CDR comprising SEQ ID NO: 52, a second CDR comprising SEQ ID NO: 54, and a third CDR comprising SEQ ID NO: 56. In some embodiments, the antibody or antibody $V_L$ chain comprises a first CDR comprising SEQ ID NO: 19, a second CDR comprising SEQ ID NO: 54, and a third CDR comprising SEQ ID NO: 47. In some embodiments, the antibody or antibody $V_L$ chain comprises a first CDR comprising SEQ ID NO: 19, a second CDR comprising SEQ ID NO: 54, and a third CDR comprising SEQ ID NO: 48. In some embodiments, the antibody or antibody $V_L$ chain comprises a first CDR comprising SEQ ID NO: 62, a second CDR comprising SEQ ID NO: 54, and a third CDR comprising SEQ ID NO: 56. In some embodiments, the antibody or antibody $V_L$ chain comprises a first CDR comprising SEQ ID NO: 49, a second CDR comprising SEQ ID NO: 54, and a third CDR comprising SEQ ID NO: 56. In some embodiments, the antibody or antibody $V_L$ chain comprises a first CDR comprising SEQ ID NO: 57, a second CDR comprising SEQ ID NO: 54, and a third CDR comprising SEQ ID NO: 56. In some embodiments, the antibody or antibody $V_L$ chain comprises a first CDR comprising SEQ ID NO: 51, a second CDR comprising SEQ ID NO: 54, and a third CDR comprising SEQ ID NO: 56.

In some embodiments, the antibody or antibody $V_L$ chain comprises a first CDR comprising SEQ ID NO: 58, a second CDR comprising SEQ ID NO: 60, and a third CDR comprising SEQ ID NO: 61. In some embodiments, the antibody or antibody $V_L$ chain comprises a first CDR comprising SEQ ID NO: 58, a second CDR comprising SEQ ID NO: 60, and a third CDR comprising SEQ ID NO: 47. In some embodiments, the antibody or antibody $V_L$ chain comprises a first CDR comprising SEQ ID NO: 58, a second CDR comprising SEQ ID NO: 60, and a third CDR comprising SEQ ID NO: 48. In some embodiments, the antibody or antibody $V_L$ chain comprises a first CDR comprising SEQ ID NO: 62, a second CDR comprising SEQ ID NO: 60, and a third CDR comprising SEQ ID NO: 61. In some embodiments, the antibody or antibody $V_L$ chain comprises a first CDR comprising SEQ ID NO: 49, a second CDR comprising SEQ ID NO: 60, and a third CDR comprising SEQ ID NO: 61. In some embodiments, the antibody or antibody $V_L$ chain comprises a first CDR comprising SEQ ID NO: 57, a second CDR comprising SEQ ID NO: 60, and a third CDR comprising SEQ ID NO: 61. In some embodiments, the antibody or antibody $V_L$ chain comprises a first CDR comprising SEQ ID NO: 51, a second CDR comprising SEQ ID NO: 60, and a third CDR comprising SEQ ID NO: 61.

In some embodiments, the antibody or antibody $V_L$ chain comprises a first CDR comprising SEQ ID NO: 63, a second CDR comprising SEQ ID NO: 64, and a third CDR comprising SEQ ID NO: 65. In some embodiments, the antibody or antibody $V_L$ chain comprises a first CDR comprising SEQ ID NO: 63, a second CDR comprising SEQ ID NO: 64, and a third CDR comprising SEQ ID NO: 47. In some embodiments, the antibody or antibody $V_L$ chain comprises a first CDR comprising SEQ ID NO: 63, a second CDR comprising SEQ ID NO: 64, and a third CDR comprising SEQ ID NO: 48. In some embodiments, the antibody or antibody $V_L$ chain comprises a first CDR comprising SEQ ID NO: 49, a second CDR comprising SEQ ID NO: 64, and a third CDR comprising SEQ ID NO: 65. In some embodiments, the antibody or antibody $V_L$ chain comprises a first CDR comprising SEQ ID NO: 57, a second CDR comprising SEQ ID NO: 64, and a third CDR comprising SEQ ID NO: 65. In some embodiments, the antibody or antibody $V_L$ chain comprises a first CDR comprising SEQ ID NO: 51, a second CDR comprising SEQ ID NO: 64, and a third CDR comprising SEQ ID NO: 65.

In some embodiments, the antibody or antibody $V_L$ chain comprises a first CDR comprising SEQ ID NO: 66, a second CDR comprising SEQ ID NO: 67, and a third CDR comprising SEQ ID NO: 68. In some embodiments, the antibody or antibody $V_L$ chain comprises a first CDR comprising SEQ ID NO: 66, a second CDR comprising SEQ ID NO: 67, and a third CDR comprising SEQ ID NO: 47. In some embodiments, the antibody or antibody $V_L$ chain comprises a first CDR comprising SEQ ID NO: 66, a second CDR comprising SEQ ID NO: 67, and a third CDR comprising SEQ ID NO: 48. In some embodiments, the antibody or antibody $V_L$ chain comprises a first CDR comprising SEQ ID NO: 69, a second CDR comprising SEQ ID NO: 67, and a third CDR comprising SEQ ID NO: 68. In some embodiments, the antibody or antibody $V_L$ chain comprises a first CDR comprising SEQ ID NO: 9, a second CDR comprising SEQ ID NO: 67, and a third CDR comprising SEQ ID NO: 68. In some embodiments, the antibody or antibody $V_L$ chain comprises a first CDR comprising SEQ ID NO: 57, a second CDR comprising SEQ ID NO: 67, and a third CDR comprising SEQ ID NO: 68. In some embodiments, the antibody or antibody $V_L$ chain comprises a first CDR comprising SEQ ID NO: 51, a second CDR comprising SEQ ID NO: 67, and a third CDR comprising SEQ ID NO: 68.

In some embodiments, the antibody or antibody $V_L$ chain comprises a first CDR comprising SEQ ID NO: 70, a second CDR comprising SEQ ID NO: 21, and a third CDR comprising SEQ ID NO: 56. In some embodiments, the antibody or antibody $V_L$ chain comprises a first CDR comprising SEQ ID NO: 70, a second CDR comprising SEQ ID NO: 54, and a third CDR comprising SEQ ID NO: 56. In some embodiments, the antibody or antibody $V_L$ chain comprises a first CDR comprising SEQ ID NO: 19, a second CDR comprising SEQ ID NO: 21, and a third CDR comprising SEQ ID NO: 47. In some embodiments, the antibody or antibody $V_L$ chain comprises a first CDR comprising SEQ ID NO: 52, a second CDR comprising SEQ ID NO: 21, and a third CDR comprising SEQ ID NO: 56. In some embodiments, the antibody or antibody $V_L$ chain comprises a first CDR comprising SEQ ID NO: 70, a second CDR comprising SEQ ID NO: 54, and a third CDR comprising SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 19; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 19; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 19; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 19; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 19; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 19; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 19; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 19; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 49; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 49; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 49; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 49; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 49; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 49; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 49; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 49; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 50; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 50; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 50; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 50; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 50; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 50; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 50; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 50; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 51; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 51; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 51; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 51; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 51; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 51; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 51; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 51; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 52; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 52; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 52; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 52; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 52; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 52; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 52; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 52; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 57; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 57; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 57; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 57; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 57; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 57; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 57; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 57; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 58; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 58; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 58; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 58; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 58; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 58; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 58; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 58; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 62; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 62; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 62; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 62; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 62; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 62; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 62; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 62; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 63; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 63; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 63; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 63; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 63; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 63; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 63; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 63; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 66; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 66; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 66; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 66; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 66; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 66; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 66; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 66; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 69; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 69; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 69; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 69; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 69; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 69; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 69; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 69; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 70; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 70; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 70; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 70; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 70; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 70; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 70; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 70; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 71; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 71; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 71; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 71; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 71; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 71; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 71; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 71; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 74; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 74; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 74; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 74; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 74; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 74; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 74; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 74; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 75; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 75; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 75; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 75; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 75; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 75; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 75; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 75; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 76; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 56.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 76; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 78.

In some embodiments, the protein comprises a first amino acid sequence or first CDR comprising a sequence of SEQ ID NO: 76; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 76; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 56.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 76; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 78.

In some embodiments, the protein comprises a first amino acid sequence or first CDR comprising a sequence of SEQ ID NO: 76; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 76; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 56.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 76; a second amino acid sequence or second CDR comprising an the sequence of SEQ ID NO: 79; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 56.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 78.

In some embodiments, the protein comprises a first amino acid sequence or first CDR comprising a sequence of SEQ ID NO: 84; a second amino acid sequence or second CDR comprising an the sequence of SEQ ID NO: 21; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 78.

In some embodiments, the protein comprises a first amino acid sequence or first CDR comprising a sequence of SEQ ID NO: 84; a second amino acid sequence or second CDR comprising an the sequence of SEQ ID NO: 54; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 56.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR In some embodiments, the protein comprises a first amino acid sequence or first CDR comprising a sequence of SEQ ID NO: 84; a second amino acid sequence or second CDR comprising an the sequence of SEQ ID NO: 60; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 56.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 78.

In some embodiments, the protein comprises a first amino acid sequence or first CDR comprising a sequence of SEQ ID NO: 84; a second amino acid sequence or second CDR comprising an the sequence of SEQ ID NO: 64; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 78.

In some embodiments, the protein comprises a first amino acid sequence or first CDR comprising a sequence of SEQ ID NO: 84; a second amino acid sequence or second CDR comprising an the sequence of SEQ ID NO: 67; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 56.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR In some embodiments, the protein comprises a first amino acid sequence or first CDR comprising a sequence of SEQ ID NO: 84; a second amino acid sequence or second CDR comprising an the sequence of SEQ ID NO: 72; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 56.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 78.

In some embodiments, the protein comprises a first amino acid sequence or first CDR comprising a sequence of SEQ ID NO: 84; a second amino acid sequence or second CDR comprising an the sequence of SEQ ID NO: 77; and a third amino acid sequence or third CDR comprising a sequence of SEQ ID NO: 80.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 23.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 47.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 48.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 61.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 65.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 68.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 73.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 78.

In some embodiments, the protein comprises a first amino acid sequence or first CDR comprising a sequence of SEQ ID NO: 84; a second amino acid sequence or second CDR comprising an the sequence of SEQ ID NO: 79; and a third amino acid sequence or third CDR comprising a sequence of SEQ ID NO: 80.

In some embodiments, the proteins comprising the first, second, and third amino acids sequences or the first, second, and third, CDRs, such as those described herein and above, are $V_L$ domains or $V_L$ chains. As used herein, the term $V_L$ domain or $V_L$ chain can be used interchangeably.

In some embodiments, the CDRs are placed in a framework. In some embodiments, the framework is a humanized light chain framework. In some embodiments, the light chain has the formula of FW1-CDR1-FW2-CDR2-FW3-CDR3-FW4, wherein FW1 is a FW1 sequence as set forth in Table 2, FW2 is a FW2 sequence as set forth in Table 2, FW3 is a FW3 sequence as set forth in Table 2, FW4 is a FW4 sequence as set forth in Table 2, CDR1 is a LCDR1 sequence as set forth in Table 2 or a CDR1 sequence as set forth in Table 3, CDR2 is a LCDR2 sequence as set forth in Table 2 or a CDR2 sequence as set forth in Table 3, and CDR3 is a LCDR3 sequence as set forth in Table 2 or a CDR3 sequence as set forth in Table 3. In some embodiments, CDR1 is a peptide having the formula or sequence as set forth in any one of SEQ ID NOs: 19, 49, 50, 51, 52, 57, 58, 62, 63, 66, 69, 70, 71, 74, 75, 76, or 84. In some CDR2 is a peptide having the formula or sequence as set forth in any one of SEQ ID NOs: 21, 54, 60, 64, 67, 72, 77, or 79. In some CDR3 is a peptide having the formula or sequence as set forth in any one of SEQ ID NOs: 23, 47, 48, 56, 61, 65, 68, 73, 78, or 80. In some embodiments FW1 is a peptide having the formula or sequence as set forth in SEQ ID NOs: 18, 25, 31, 36, 38, or 46. In some embodiments FW2 is a peptide having the formula or sequence as set forth in SEQ ID NOs: 20, 26, 30, 32, 35, or 53. In some embodiments FW3 is a peptide having the formula or sequence as set forth in SEQ ID NOs: 22, 27, 33, 37, 39, 41, 42, 44, 45, 55, or 59. In some embodiments FW4 is a peptide having the formula or sequence as set forth in SEQ ID NOs: 24, 29, 34, 40, or 43.

In some embodiments, a $V_L$ chain is provided, wherein the $V_L$ chain comprises a CDR1 peptide having the formula or sequence as set forth in any one of SEQ ID NOs: 19, 49, 50, 51, 52, 57, 58, 62, 63, 66, 69, 70, 71, 74, 75, 76, or 84; a CDR2 peptide having the formula or sequence as set forth in any one of SEQ ID NOs: 21, 54, 60, 64, 67, 72, 77, or 79; and a CDR3 peptide having the formula or sequence as set forth in any one of SEQ ID NOs: 23, 47, 48, 56, 61, 65, 68, 73, 78, or 80.

In some embodiments, an antibody is provided, wherein light chain comprises a CDR1 peptide having the formula or sequence as set forth in any one of SEQ ID NOs: 19, 49, 50, 51, 52, 57, 58, 62, 63, 66, 69, 70, 71, 74, 75, 76, or 84; a CDR2 peptide having the formula or sequence as set forth in any one of SEQ ID NOs: 21, 54, 60, 64, 67, 72, 77, or 79; and a CDR3 peptide having the formula or sequence as set forth in any one of SEQ ID NOs: 23, 47, 48, 56, 61, 65, 68, 73, 78, or 80.

In some embodiments a protein or light chain is provided having the formula of: FW1-CDR1-FW2-CDR2-FW3-CDR3-FW4, wherein:
wherein FW1 is a FW1 sequence as set forth in Table 2, FW2 is a FW2 sequence as set forth in Table 2, FW3 is a FW3 sequence as set forth in Table 2, FW4 is a FW4 sequence as set forth in Table 2, CDR1 is a LCDR1 sequence as set forth in Table 2 or a CDR1 sequence as set forth in Table 3, CDR2 is a LCDR2 sequence as set forth in Table 2 or a CDR2 sequence as set forth in Table 3, and CDR3 is a LCDR3 sequence as set forth in Table 2 or a CDR3 sequence as set forth in Table 3. In some embodiments, CDR1 is a peptide having the formula or sequence as set forth in any one of SEQ ID NOs: 19, 49, 50, 51, 52, 57, 58, 62, 63, 66, 69, 70, 71, 74, 75, 76, or 84. In some CDR2 is a peptide having the formula or sequence as set forth in any one of SEQ ID NOs: 21, 54, 60, 64, 67, 72, 77, or 79. In some CDR3 is a peptide having the formula or sequence as set forth in any one of SEQ ID NOs: 23, 47, 48, 56, 61, 65, 68, 73, 78, or 80. In some embodiments FW1 is a peptide having the formula or sequence as set forth in SEQ ID NOs: 18, 25, 31, 36, 38, or 46. In some embodiments FW2 is a peptide having the formula or sequence as set forth in SEQ ID NOs: 20, 26, 30, 32, 35, or 53. In some embodiments FW3 is a peptide having the formula or sequence as set forth in SEQ ID NOs: 22, 27, 33, 37, 39, 41, 42, 44, 45, 55, or 59. In some embodiments FW4 is a peptide having the formula or sequence as set forth in SEQ ID NOs: 24, 29, 34, 40, or 43. In some embodiments, the protein is an antibody.

In some embodiments, one of the proteins of SEQ ID NO: 1-9 is paired with a heavy chain, such as $V_H$ domain to form a protein that binds a target. The $V_H$ domains provided herein are exemplary and are also non-limiting. In some embodiments, the $V_H$ domain binds to PD-1, Her-2, CD151, IGSF8, CD315, CD147, CD59, CD315. In some embodiments, the $V_H$ domain binds to a checkpoint molecule, such as PD-L1, PD-L2, CTLA4, and the like. In some embodiments, the $V_H$ domain binds to any antigen desired. In some embodiments, the antigen is a tetraspanin, such as, but not limited to, TSP-2, TSP-3, TSP-4, NAG-2, TSP-5, TSP-6, CD231/TALLA-1/A15, CO-029, NET-5, OCULOSPANIN, CD151-like, NET-2, NET-6, NET-7, TM4-B, UP1b, UPK1B, UPla, UPK1A, RDS, PRPH2, ROM1, CD151, CD53, CD37, CD82, CD9, CD63, SAS, or TSSC6. As provided for herein, the $V_L$ domains, which can be referred to as a common light chain can be paired with any $V_H$ domain. The protein can be an antibody. In some embodiments, the heavy chain is selected from one of the following:

| Clone Name | SEQ ID NO: | Sequence |
|---|---|---|
| HC-CD151 | SEQ ID NO: 10 | AVTLDESGGGLQMPGGALSLVCKA SGFTFSSYGMEWVRQAPGKGLEWV AGISSGGGSTDYGTAVKGRATISR DNGQSTVRLQLNNLRAEDTGTYFC AKSAYGGTWDGDDIDAWGHGTEVI VSS |
| HC-IGSF8 | SEQ ID NO: 11 | AVTLDESGGGLQTPGGGLSLVCKA SGFSISSYEMQWVRQAPGKGLEWV AGIDDDGSSRAYAPAVKGRATISR DNGQSTVRLQLNNLRAEDTGTYYC AKTIYAATLNAGEIDAWGHGTEVI VSS |
| HC-CD63 | SEQ ID NO: 12 | AVTLDESGGGLQTPGGALSLVCKA SGFTFSDRGMHWVRQAPGKGLEWV AGIRSTGSFTLYGAAVKGRATISR DDGQSTLRLQLNNLRAEDTGTYYC AKSAGGYGCGRGWCGVDDIDAWGH GTEVIVSS |
| HC-CD315 | SEQ ID NO: 13 | AVTLDESGGGLQTPGGGLSLVCKA SGFTFRNYIMQWVRQAPGKELEWV AGISTSGRTYYGTAVKGRATISRD TGQSTVRLQLNNLRAEDTGTYFCA KYGSGVSYSYNAGQIDAWGHGTEV IVSS |
| HC-CD147 | SEQ ID NO: 14 | AVTLDESGGGLQTPGGGLSLVCKA SGFTFSSYAMYWVRQAPGKGLEWV AGISRDGSSGRYGAAVKGRATISR DNGQSTVRLQLNNLRAEDTATYFC AKSGYGDYTSADEIDAWGHGTEVI VSS |
| HC-CD59 | SEQ ID NO: 15 | AVTLDESGGGLQTPGGGLSLVCKA SGFDFSSFDMVWVRQAPGKGLEWV AGISYSNTDTSYAPAVDGRATISR DNGQSTVRLQLNNLRAEDSATYYC AKSAGGCCYRADNIDAWGHGTEVI VSS |
| HC-CD81 | SEQ ID NO: 16 | AVTLDESGGGLQTPGGALSLVCKA SGFSIGDYNMGWVRQAPGKGLEWV AGIDAGGGTWRATAVKGRATISRD NGQSTVRLQLNNLRAEDTATYFCA KSTDSSANCCANSIDAWGHGTEVI VSS |
| HC-CD315 | SEQ ID NO: 17 | AVTLDESGGGLQTPGGGLSLVCKA SGFTSSNYIMQWVRQAPGKGLDWV AGISTSGRTYYGTAVKGRATISRD NGQSTVRLQLSNLRAEDTGIYFCA KFGSGVSYTYNAGQIDAWGHGTEV IVSS |

In some embodiments, any of the $V_H$ chains can be combined with any of the $V_L$ chains provided for herein. As demonstrated herein, the $V_L$ chains do not materially impact the binding of the antibody to different targets, thus, they can be combined in any combination. In some embodiments, the $V_H$ is combined with one of F10-$V_L$ (SEQ ID NO: 1); F10h-$V_L$ (SEQ ID NO: 2); B9-$V_L$ (SEQ ID NO: 3); or B9h-$V_L$ (SEQ ID NO: 4). In some embodiments, the $V_H$ is combined with a sequence of SEQ ID NO: 5, 6, 7, 8 or 9.

As provided for herein, the different peptides ($V_H$ or $V_L$) described herein can be linked with a peptide linker or not linked with a peptide linker and instead for a contiguous sequence. In some embodiments, the peptide linker comprises a sequence of GQSSRSSGGGGSSGGGGS (SEQ ID NO: 81); (GGGGS)$_n$ (SEQ ID NO: 82), (GGGGA)$_n$ (SEQ ID NO: 83), or any combination thereof, wherein each n is independently 1-5. The linked peptide format can be represented by a formula of $V_H$—Z—$V_L$ or $V_L$—Z—$V_H$, wherein Z is the peptide linker. In some embodiments, Z is GQSSRSSGGGGSSGGGGS (SEQ ID NO: 81); (GGGGS)$_n$ (SEQ ID NO: 82), or (GGGGA)$_n$ (SEQ ID NO: 83), or any combination thereof, wherein each n is independently 1-5.

As provided for herein, the antibodies, or antigen binding fragments thereof can be variants of the sequences.

As provided for herein, the DNA (or RNA sequences) that may encode a protein may vary due to the degeneracy of the genetic code. Such variants are encompassed by the embodiments provided for herein.

In some embodiments, the proteins or antibodies provided herein are linked to a Fc protein or region. Examples of such Fc proteins can be found in U.S. Pat. Nos. 9,580,486, 7,105,653, 9,616,105, 9,428,567, 10,336,818, US2017/0051029, WO2016/164937, US2014/0286898A1, WO2014153111A2, WO2010/085495, WO2016014428A2, WO2016025385A1, US2017/0037102, and US2006/0269515, each of which are incorporated by reference in its entirety.

In some embodiments, the Fc Region comprises what is known as the LALA mutation. Using the Kabat numbering of the Fc region, this would correspond to L247A, L248A, and G250A. In some embodiments, using the EU numbering of the Fc region, the Fc region comprises a L234A mutation, a L235A mutation, and/or a G237A mutation. Regardless of the numbering system used, in some embodiments, the Fc portion can comprise mutations that correspond to these residues. In some embodiments, the Fc Region comprises N297G or N297A (kabat numbering) mutations. The Kabat numbering is based upon a full-length sequence, but would be used in a fragment based upon a traditional alignment used by one of skill in the art for the Fc region.

In some embodiments, the Fc region is linked to the $V_H$ or $V_L$ protein or a protein sequence provided for herein. The Fc region can be directly linked to one another or linked through one or more linker, such as the sequences as provided for herein.

As used herein, the term "fused" or "linked" when used in reference to a protein having different domains or heterologous sequences means that the protein domains are part of the same peptide chain that are connected to one another with either peptide bonds or other covalent bonding. The domains or section can be linked or fused directly to one another or another domain or peptide sequence can be between the two domains or sequences and such sequences would still be considered to be fused or linked to one another. In some embodiments, the various domains or proteins provided for herein are linked or fused directly to one another or a linker sequences, such as the glycine/serine or glycine/alanine sequences described herein, which can link two domains together.

Pharmaceutical Compositions

The antibodies or proteins comprising a sequence as provided herein can be prepared as a pharmaceutical composition. In some embodiments, the pharmaceutical or sterile compositions provided herein, the antibody or antigen binding fragment thereof or other proteins provided can be are admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984). In some embodiments, the pharmaceutical compositions can comprise a pharmaceutically acceptable excipient or carrier.

For example, formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.). In some embodiments, the antibodies are diluted to an appropriate concentration in a sodium acetate solution pH 5-6, and NaCl or sucrose is added for tonicity. Additional agents, such as polysorbate 20 or polysorbate 80, may be added to enhance stability.

In some embodiments, a composition or compound as provided herein is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In some embodiments, the antibody or antigen binding fragment thereof can be administered by an invasive route such as by injection. In some embodiments, the antibodies or antigen binding fragment thereof, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present embodiments.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert, et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable.

Antibodies or antigen binding fragments thereof can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 mg/kg body weight, more generally at least 0.2 µg/kg, 0.5 µg/kg, 1 µg/kg, 10 µg/kg, 100 ag/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) New Engl. J. Med. 349:427-434; Herold, et al. (2002) New Engl. J. Med. 346:1692-1698; Liu, et al. (1999) J. Neurol. Neurosurg. Psych. 67:451-456; Portielji, et al. (20003) Cancer Immunol. Immunother. 52:133-144). Doses may also be provided to achieve a pre-determined target concentration of the antibody in the subject's serum, such as 0.1, 0.3, 1, 3, 10, 30, 100, 300 µg/ml or more. In other embodiments, a fully human antibody is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of the antibody, or antigen binding fragment thereof, that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the binding compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments, an amount is a therapeutically effective amount if it is an amount that can be used to treat, ameliorate or a disease that is mediated or impacted by the antigen target of the antibody.

The term "subject" as used throughout includes any organism, such as an animal, including a mammal (e.g., rat, mouse, dog, cat, rabbit) and, for example, a human. A subject can be also be referred to as a patient. In some embodiments, the subject is a subject in need thereof. A subject that is "in need thereof" refers to a subject that has been identified as requiring treatment for the condition that is to be treated and is treated with the specific intent of treating such condition. The conditions can be, for example, any of the conditions described herein.

Kits are also provided which are useful for carrying out embodiments described herein. In some embodiments, the present kits comprise a first container containing or packaged in association with the above-described antibodies. The kit may also comprise another container containing or packaged in association solutions necessary or convenient for carrying out the embodiments. The containers can be made of glass, plastic or foil and can be a vial, bottle, pouch, tube, bag, etc. The kit may also contain written information, such as procedures for carrying out the embodiments or analytical information, such as the amount of reagent contained in the first container means. The container may be in another container apparatus, e.g. a box or a bag, along with the written information.

In some embodiments, method of preparing an antibody are provided. In some embodiments, the methods comprise culturing a host cell comprising a nucleotide sequence that encodes chicken-derived light chain and a heavy chain that binds to a specific antigen to express the antibody that comprises a chicken-derived light chain and a heavy chain that binds to the specific antigen. The antibody can be any type of antibody provided herein or as desired that comprises a light chain, such as a chicken-derived light chain or other light chain provided herein or a light chain with a CDR set as provided herein and a heavy chain that binds to a specific antigen. In some embodiments, the antigen or binding partner is PD-1 or HER-2. In some embodiments, the nucleotide sequence encodes a light chain comprises a protein comprising a first amino acid sequence or a first CDR selected from the group consisting of: SEQ ID NOs: 19, 49, 50, 51, 52, 57, 58, 62, 63, 66, 69, 70, 71, 74, 75, 76, and 84; a second amino acid sequence or second CDR selected from the group consisting of: 21, 54, 60, 64, 67, 72, 77, and 79; and a third amino acid sequence or third CDR selected from the group consisting of: 23, 47, 48, 56, 61, 65, 68, 73, 78, and 80. In some embodiments, the nucleotide sequence encodes a light chain comprises a protein comprising a first sequence or the first CDR selected comprises a sequence selected from the group consisting of: SEQ ID NOs: 19, 49, 50, 51, 52, 57, 58, 62, 63, 66, 69, and 70; the second sequence or second CDR comprises a sequence selected from the group consisting of: 21, 54, 60, 64, and 67; and the third sequence or third CDR comprises a sequence selected from the group consisting of: 23, 47, 48, 56, 61, 65, and 68. In some embodiments, light chain encodes a protein sequence comprising a first sequence or first CDR comprising a sequence of SEQ ID NO: 19, a second sequence or second CDR comprising a sequence of SEQ ID NO: 21, and a third sequence or third CDR comprising a sequence of SEQ ID NO: 23. In some embodiments, the nucleotide sequence encodes a light chain that is at least, or about 60, 70, 80, 85, 90, 91, 92, 93, 94, 95, 96, 97, 98, or 99% identical to a protein having a sequence of SEQ ID NO: SEQ ID NO: 2 (F10h). SEQ ID NO: 1 (F10), SEQ ID NO: 3 (B9), SEQ ID NO: 4 (B9h), SEQ ID NO: 5 (N6-G3), SEQ ID NO: 6 (N6-C5), SEQ ID NO: 7 (N6-F11), SEQ ID NO: 8 (N5-B4), or SEQ ID NO: 9 (N5-B7). In some embodiments, the nucleotide sequence encodes a light chain comprising a protein having a sequence of SEQ ID NO: SEQ ID NO: 2 (F10h). SEQ ID NO: 1 (F10), SEQ ID NO: 3 (B9), SEQ ID NO: 4 (B9h), SEQ ID NO: 5 (N6-G3), SEQ ID NO: 6 (N6-C5), SEQ ID NO: 7 (N6-F11), SEQ ID NO: 8 (N5-B4), or SEQ ID NO: 9 (N5-B7). These are non-limiting examples and any of the proteins provided for herein can be encoded by the nucleotide sequence. In some embodiments, the protein is a variant of those provided for herein.

In some embodiments, embodiments provided herein also include, but are not limited to:

1. A protein comprising a first amino acid sequence or a first CDR selected from the group consisting of: SEQ ID NOs: 19, 49, 50, 51, 52, 57, 58, 62, 63, 66, 69, 70, 71, 74, 75, and 76; a second amino acid sequence or second CDR selected from the group consisting of: 21, 54, 60, 64, 67, 72, 77, and 79; and a third amino acid sequence or third CDR selected from the group consisting of: 23, 47, 48, 56, 61, 65, 68, 73, 78, and 80.
2. The protein of embodiment 1, wherein the first sequence or the first CDR selected comprises a sequence selected from the group consisting of: SEQ ID NOs: 19, 49, 50, 51, 52, 57, 58, 62, 63, 66, 69, and 70; the second sequence or second CDR comprises a sequence selected from the group consisting of: 21, 54, 60, 64, and 67; and the third sequence or third CDR comprises a sequence selected from the group consisting of: 23, 47, 48, 56, 61, 65, and 68.
3. The protein of embodiment 1, wherein the protein comprises a first sequence or first CDR comprising a sequence of SEQ ID NO: 19, a second sequence or second CDR comprising a sequence of SEQ ID NO: 21, and a third sequence or third CDR comprising a sequence of SEQ ID NO: 23.
4. The protein of embodiment 1, wherein the protein comprises a first sequence or first CDR comprising a sequence of SEQ ID NO: 52, a second sequence or second CDR comprising a sequence of SEQ ID NO: 54, and a third sequence or third CDR comprising a sequence of SEQ ID NO: 56.
5. The protein of embodiment 1, wherein the protein comprises a first sequence or first CDR comprising a sequence of SEQ ID NO: 58, a second sequence or second CDR comprising a sequence of SEQ ID NO: 60, and a third sequence or third CDR comprising a sequence of SEQ ID NO: 61.
6. The protein of embodiment 1, wherein the protein comprises a first sequence or first CDR comprising a sequence of SEQ ID NO: 63, a second sequence or second CDR comprising a sequence of SEQ ID NO: 64, and a third sequence or third CDR comprising a sequence of SEQ ID NO: 65.
7. The protein of embodiment 1, wherein the protein comprises a first sequence or first CDR comprising a sequence of SEQ ID NO: 66, a second sequence or second CDR comprising a sequence of SEQ ID NO: 67, and a third sequence or third CDR comprising a sequence of SEQ ID NO: 68.
8. The protein of embodiment 1, wherein the protein comprises a first sequence or first CDR comprising a sequence of SEQ ID NO: 19, a second sequence or second CDR comprising a sequence of SEQ ID NO: 27, and a third sequence or third CDR comprising a sequence of SEQ ID NO: 23.
9. The protein of embodiment 1, wherein the protein comprises a first sequence or first CDR comprising a sequence of SEQ ID NO: 18, a second sequence or second CDR comprising a sequence of SEQ ID NO: 21, and a third sequence or third CDR comprising a sequence of SEQ ID NO: 23.
10. The protein of embodiment 1, wherein the protein comprises a first sequence or first CDR comprising a sequence of SEQ ID NO: 19, a second sequence or second CDR comprising a sequence of SEQ ID NO: 21, and a third sequence or third CDR comprising a sequence of SEQ ID NO: 47.
11. The protein of embodiment 1, wherein the protein comprises a first sequence or first CDR comprising a sequence of SEQ ID NO: 19, a second sequence or second CDR comprising a sequence of SEQ ID NO: 21, and a third sequence or third CDR comprising a sequence of SEQ ID NO: 48.
12. The protein of embodiment 1, wherein the protein comprises a first sequence or first CDR comprising a sequence of SEQ ID NO: 49, a second sequence or second CDR comprising a sequence of SEQ ID NO: 21, and a third sequence or third CDR comprising a sequence of SEQ ID NO: 23.
13. The protein of embodiment 1, wherein the protein comprises a first sequence or first CDR comprising a sequence of SEQ ID NO: 50, a second sequence or second CDR comprising a sequence of SEQ ID NO: 21, and a third sequence or third CDR comprising a sequence of SEQ ID NO: 47.
14. The protein of embodiment 1, wherein the protein comprises a first sequence or first CDR comprising a sequence of SEQ ID NO: 52, a second sequence or second CDR comprising a sequence of SEQ ID NO: 54, and a third sequence or third CDR comprising a sequence of SEQ ID NO: 56.
15. The protein of embodiment 1, wherein the protein comprises a first sequence or first CDR comprising a sequence of SEQ ID NO: 19, a second sequence or second CDR comprising a sequence of SEQ ID NO: 54, and a third sequence or third CDR comprising a sequence of SEQ ID NO: 47.
16. The protein of embodiment 1, wherein the protein comprises a first sequence or first CDR comprising a sequence of SEQ ID NO: 19, a second sequence or second CDR comprising a sequence of SEQ ID NO: 54, and a third sequence or third CDR comprising a sequence of SEQ ID NO: 48.
17. The protein of embodiment 1, wherein the protein comprises a first sequence or first CDR comprising a sequence of SEQ ID NO: 62, a second sequence or second CDR comprising a sequence of SEQ ID NO: 54, and a third sequence or third CDR comprising a sequence of SEQ ID NO: 56.
18. The protein of embodiment 1, wherein the protein comprises a first sequence or first CDR comprising a sequence of SEQ ID NO: 49, a second sequence or second CDR comprising a sequence of SEQ ID NO: 54, and a third sequence or third CDR comprising a sequence of SEQ ID NO: 56.
19. The protein of embodiment 1, wherein the protein comprises a first sequence or first CDR comprising a sequence of SEQ ID NO: 57, a second sequence or second CDR comprising a sequence of SEQ ID NO: 54, and a third sequence or third CDR comprising a sequence of SEQ ID NO: 56.
20. The protein of embodiment 1, wherein the protein comprises a first sequence or first CDR comprising a sequence of SEQ ID NO: 51, a second sequence or second CDR comprising a sequence of SEQ ID NO: 54, and a third sequence or third CDR comprising a sequence of SEQ ID NO: 56.
21. The protein of embodiment 1, wherein the protein comprises a first sequence or first CDR comprising a sequence of SEQ ID NO: 58, a second sequence or second CDR comprising a sequence of SEQ ID NO: 60, and a third sequence or third CDR comprising a sequence of SEQ ID NO: 47.
22. The protein of embodiment 1, wherein the protein comprises a first sequence or first CDR comprising a sequence of SEQ ID NO: 58, a second sequence or second CDR comprising a sequence of SEQ ID NO: 60, and a third sequence or third CDR comprising a sequence of SEQ ID NO: 48.
23. The protein of embodiment 1, wherein the protein comprises a first sequence or first CDR comprising a sequence of SEQ ID NO: 62, a second sequence or second CDR comprising a sequence of SEQ ID NO: 60, and a third sequence or third CDR comprising a sequence of SEQ ID NO: 61.
24. The protein of embodiment 1, wherein the protein comprises a first sequence or first CDR comprising a sequence of SEQ ID NO: 49, a second sequence or second CDR comprising a sequence of SEQ ID NO: 60, and a third sequence or third CDR comprising a sequence of SEQ ID NO: 61.
25. The protein of embodiment 1, wherein the protein comprises a first sequence or first CDR comprising a sequence of SEQ ID NO: 57, a second sequence or second CDR comprising a sequence of SEQ ID NO: 60, and a third sequence or third CDR comprising a sequence of SEQ ID NO: 61.
26. The protein of embodiment 1, wherein the protein comprises a first sequence or first CDR comprising a sequence of SEQ ID NO: 51, a second sequence or second CDR comprising a sequence of SEQ ID NO: 60, and a third sequence or third CDR comprising a sequence of SEQ ID NO: 61.
27. The protein of embodiment 1, wherein the protein comprises a first sequence or first CDR comprising a sequence of SEQ ID NO: 63, a second sequence or second CDR comprising a sequence of SEQ ID NO: 64, and a third sequence or third CDR comprising a sequence of SEQ ID NO: 65.
28. The protein of embodiment 1, wherein the protein comprises a first sequence or first CDR comprising a sequence of SEQ ID NO: 63, a second sequence or second CDR comprising a sequence of SEQ ID NO: 64, and a third sequence or third CDR comprising a sequence of SEQ ID NO: 47.
29. The protein of embodiment 1, wherein the protein comprises a first sequence or first CDR comprising a sequence of SEQ ID NO: 63, a second sequence or second CDR comprising a sequence of SEQ ID NO: 64, and a third sequence or third CDR comprising a sequence of SEQ ID NO: 48.
30. The protein of embodiment 1, wherein the protein comprises a first sequence or first CDR comprising a sequence of SEQ ID NO: 49, a second sequence or second CDR comprising a sequence of SEQ ID NO: 64, and a third sequence or third CDR comprising a sequence of SEQ ID NO: 65.
31. The protein of embodiment 1, wherein the protein comprises a first sequence or first CDR comprising a sequence of SEQ ID NO: 57, a second sequence or second CDR comprising a sequence of SEQ ID NO: 64, and a third sequence or third CDR comprising a sequence of SEQ ID NO: 65.
32. The protein of embodiment 1, wherein the protein comprises a first sequence or first CDR comprising a sequence of SEQ ID NO: 66, a second sequence or second CDR comprising a sequence of SEQ ID NO: 67, and a third sequence or third CDR comprising a sequence of SEQ ID NO: 68.
33. The protein of embodiment 1, wherein the protein comprises a first sequence or first CDR comprising a sequence of SEQ ID NO: 66, a second sequence or second CDR comprising a sequence of SEQ ID NO: 67, and a third sequence or third CDR comprising a sequence of SEQ ID NO: 47.
34. The protein of embodiment 1, wherein the protein comprises a first sequence or first CDR comprising a sequence of SEQ ID NO: 66, a second sequence or second CDR comprising a sequence of SEQ ID NO: 67, and a third sequence or third CDR comprising a sequence of SEQ ID NO: 48.
35. The protein of embodiment 1, wherein the protein comprises a first sequence or first CDR comprising a sequence of SEQ ID NO: 69, a second sequence or second CDR comprising a sequence of SEQ ID NO: 67, and a third sequence or third CDR comprising a sequence of SEQ ID NO: 68.
36. The protein of embodiment 1, wherein the protein comprises a first sequence or first CDR comprising a sequence of SEQ ID NO: 57, a second sequence or second CDR comprising a sequence of SEQ ID NO: 67, and a third sequence or third CDR comprising a sequence of SEQ ID NO: 68.
37. The protein of embodiment 1, wherein the protein comprises a first sequence or first CDR comprising a sequence of SEQ ID NO: 51, a second sequence or second CDR comprising a sequence of SEQ ID NO: 67, and a third sequence or third CDR comprising a sequence of SEQ ID NO: 68.
38. The protein of embodiment 1, wherein the protein comprises a first sequence or first CDR comprising a sequence of SEQ ID NO: 70, a second sequence or second CDR comprising a sequence of SEQ ID NO: 54, and a third sequence or third CDR comprising a sequence of SEQ ID NO: 56.
39. The protein of embodiment 1, wherein the protein comprises a first sequence or first CDR comprising a sequence of SEQ ID NO: 52, a second sequence or second CDR comprising a sequence of SEQ ID NO: 21, and a third sequence or third CDR comprising a sequence of SEQ ID NO: 56.
40. The protein of embodiment 1, wherein the protein comprises a first sequence or first CDR comprising a sequence of SEQ ID NO: 70, a second sequence or second CDR comprising a sequence of SEQ ID NO: 54, and a third sequence or third CDR comprising a sequence of SEQ ID NO: 48.
41. The protein of embodiment 1, wherein the protein comprises a first sequence or first CDR comprising a sequence of SEQ ID NO: 70, a second sequence or second CDR comprising a sequence of SEQ ID NO: 21, and a third sequence or third CDR comprising a sequence of SEQ ID NO: 56.
42. The protein of embodiment any one of embodiments 1-41, wherein the protein is an antibody.
43. The protein of any one of embodiments 1-41, wherein the protein is a VL peptide or VL chain.
44. The protein of embodiment 43, wherein the protein further comprises a $V_H$ chain.
45. The protein of embodiment 1, wherein the protein comprises a sequence that is at least, or about, 60%, 70%, 80%, 85%, 90%, 91%, 92%, 93%, 94%, 95%, 96%, 97%, 98%, or 99% identical to, SEQ ID NO: 2 (F10h). SEQ ID NO: 1 (F10), SEQ ID NO: 3 (B9), SEQ ID NO: 4 (B9h), SEQ ID NO: 5 (N6-G3), SEQ ID NO: 6 (N6-C5), SEQ ID NO: 7 (N6-F11), SEQ ID NO: 8 (N5-B4), or SEQ ID NO: 9 (N5-B7).
46. A polypeptide comprising the protein of any one of embodiments 1-43 or 45 and a second peptide.
47. The polypeptide of embodiment 46, wherein the second peptide is a first $V_H$ peptide.
48. The polypeptide of embodiment 47, wherein the $V_H$ peptide comprises a sequence of SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17.
49. The polypeptide of embodiment 46, wherein the polypeptide is an antibody.
50. The polypeptide of embodiment 47, wherein the polypeptide is an antibody.
51. The polypeptide of embodiment 48, wherein the polypeptide is an antibody.
52. The polypeptide of embodiment 49, wherein the antibody is a scFv antibody.
53. The polypeptide of embodiment 51, wherein the polypeptide is a chicken derived antibody.
54. The polypeptide of embodiment 47, wherein the polypeptide further comprises a third peptide.
55. The polypeptide of embodiment 54, wherein the second and third peptides comprise different sequence.
56. The polypeptide of embodiment 54, wherein the second and third peptides comprise the same sequence.
57. The polypeptide of embodiment 54, wherein the third peptide is a second $V_H$ peptide.
58. The polypeptide of embodiment 57, wherein the first $V_H$ peptide and the second $V_H$ peptide comprise the same sequence.
59. The polypeptide of embodiment 57, wherein the first $V_H$ peptide and the second $V_H$ peptide comprise different sequences.
60. The polypeptide of embodiment 57, wherein the first and second $V_H$ peptides bind to different targets.
61. The polypeptide of embodiment 57, wherein the first and second $V_H$ peptides bind to the same target.
62. The polypeptide of embodiment 57, wherein the first and second $V_H$ peptides bind to the same epitope.
63. The polypeptide of embodiment 57, wherein the first and second $V_H$ peptides bind to different epitopes.
64. The polypeptide of any one of the preceding embodiments, wherein the polypeptide comprises a sequence selected from SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17.
65. The polypeptide of any of the preceding embodiments, wherein the polypeptide does not comprise a linker.
66. The polypeptide of any of the preceding embodiments, wherein the polypeptide does not comprise a linker having a sequence of

GQSSRSSGGGGSSGGGGS. (SEQ ID NO: 81)

67. The polypeptide of any of the preceding embodiments, wherein the polypeptide comprises a linker.
68. The polypeptide of embodiment 67, wherein the linker is a peptide linker.
69. The polypeptide of embodiments 67-68, wherein the linker links the peptide of embodiment 1 to the second peptide.
70. The polypeptide of embodiments 67-69, wherein the linker comprises a sequence of $(GGGGS)_n$ (SEQ ID NO: 82) or $(GGGGA)_n$ (SEQ ID NO: 83), wherein each n is independently 1-5.
71. An antibody comprising a peptide of any one of embodiments 1-43 or 45.
72. The antibody of embodiment 71, wherein the antibody is humanized.
73. A multi-specific antibody comprising a peptide of any one of embodiments 1-43 or 45 and one or more $V_H$ peptides.
74. The multi-specific antibody of embodiment 73, wherein the antibody comprises a first $V_H$ peptide and a second $V_H$ peptide.
75. The multi-specific antibody of embodiment 74, wherein the first $V_H$ peptide and the second $V_H$ peptide bind to different targets.
76. The multi-specific antibody of embodiment 74, wherein the first $V_H$ peptide and the second $V_H$ peptide are bound or linked to the same VL peptide.
77. An antibody comprising a LCDR1 of SEQ ID NO: 19, or a variant thereof.
78. An antibody comprising a LCDR2 of SEQ ID NO: 21, or a variant thereof.
79. An antibody comprising a LCDR3 of SEQ ID NO: 23, or a variant thereof.
80. An antibody comprising a LCDR1 of SEQ ID NO: 19, a LCDR2 of SEQ ID NO: 21, a LCDR3 of SEQ ID NO: 23, or any variants thereof.
81. A protein or antibody comprising a peptide comprising a sequence as set forth in SEQ ID NOs: 18-80.
82. A protein or antibody comprising a sequence as set forth in Table 2 or Table 3.
83. The protein or antibody of embodiments 81 or 82, wherein the protein or antibody further comprises one, two, or each of a peptide comprising a sequence of SEQ ID NO: 19, SEQ ID NO: 21, or SEQ ID NO: 23.
84. The protein or antibody of any one of embodiments 35-37, wherein the protein or antibody comprises a peptide sequence of SEQ ID NO: 19 and SEQ ID NO: 21; a peptide sequence of SEQ ID NO: 19 and SEQ ID NO: 23; a peptide sequence of SEQ ID NO: 21 and SEQ ID NO: 23, or a peptide sequence of SEQ ID NO: 19, SEQ ID NO: 21, and SEQ ID NO: 23.

85. A protein having the formula of:
FW1-CDR1-FW2-CDR2-FW3-CDR3-FW4, wherein:
FW1 is a peptide having the formula or sequence as set forth in SEQ ID NOs: 18, 25, 31, 36, 38, or 46;
CDR1 is a peptide having the formula or sequence as set forth in any one of SEQ ID NOs: 19, 49, 50, 51, 52, 57, 58, 62, 63, 66, 69, 70, 71, 74, 75, 76, or 84;
FW2 is a peptide having the formula or sequence as set forth in SEQ ID NOs: 20, 26, 30, 32, 35, or 53;
CDR2 is a peptide having the formula or sequence as set forth in any one of SEQ ID NOs: 21, 54, 60, 64, 67, 72, 77, or 79;
FW3 is a peptide having the formula or sequence as set forth in SEQ ID NOs: 22, 27, 33, 37, 39, 41, 42, 44, 45, 55, or 59;
CDR3 is a peptide having the formula or sequence as set forth in any one of SEQ ID NOs: 23, 47, 48, 56, 61, 65, 68, 73, 78, or 80; and
FW4 is a peptide having the formula or sequence as set forth in SEQ ID NOs: 24, 29, 34, 40, or 43.

86. A polypeptide comprising the protein of embodiment 85 and a $V_H$ domain.

87. The polypeptide of embodiment 86, wherein the protein of embodiment 85 and a $V_H$ domain are linked together through a linker.

88. The polypeptide of embodiment 86, wherein the polypeptide is an antibody.

89. The polypeptide of embodiment 87, wherein the antibody is a scFv antibody.

90. A nucleic acid molecule encoding the protein, polypeptide, or antibody of any one of embodiments 1-89.

91. A vector comprising the nucleic acid molecule of embodiment 90.

92. A cell comprising the nucleic comprising the nucleic acid molecule of embodiment 90 or the vector of embodiment 91.

93. A pharmaceutical composition comprising the protein, polypeptide, or antibody of any one of embodiments 1-89 or a nucleic acid molecule encoding the same.

94. The pharmaceutical composition of embodiment 93, wherein the composition is an injectable pharmaceutical composition.

95. The pharmaceutical compositions of any one of embodiments 93 or 94, wherein the composition is sterile.

96. The pharmaceutical compositions of any one of embodiments 93-95, wherein the composition is pyrogen free.

97. A method of delivering a protein, polypeptide, or antibody of any one of embodiments 1-89 to a subject, the method comprising administering to the subject the protein, polypeptide, or antibody of any one of embodiments 1-89 or a nucleic acid molecule encoding the same.

98. A method of treating a disease in a subject with a protein, polypeptide, or antibody of any one of embodiments 1-89, the method comprising administering to the subject the protein, polypeptide, or antibody of any one of embodiments 1-89 or a nucleic acid molecule encoding the same to the subject.

99. A method of preparing an antibody, the method comprising culturing a host cell comprising a nucleotide sequence that encodes chicken-derived light chain and a heavy chain that binds to a specific antigen to express the antibody that comprises a chicken-derived light chain and a heavy chain that binds to the specific antigen.

100. The method of embodiment 99, wherein antigen is PD-1 or HER-2.

101. The method of embodiments 99 or 100, wherein the nucleotide sequence encodes a light chain comprises a protein comprising a first amino acid sequence or a first CDR selected from the group consisting of: SEQ ID NOs: 19, 49, 50, 51, 52, 57, 58, 62, 63, 66, 69, 70, 71, 74, 75, 76, and 84; a second amino acid sequence or second CDR selected from the group consisting of: 21, 54, 60, 64, 67, 72, 77, and 79; and a third amino acid sequence or third CDR selected from the group consisting of: 23, 47, 48, 56, 61, 65, 68, 73, 78, and 80.

102. The method of embodiments 99 or 100, wherein the nucleotide sequence encodes a light chain comprises a protein comprising a first sequence or the first CDR selected comprises a sequence selected from the group consisting of: SEQ ID NOs: 19, 49, 50, 51, 52, 57, 58, 62, 63, 66, 69, and 70; the second sequence or second CDR comprises a sequence selected from the group consisting of: 21, 54, 60, 64, and 67; and the third sequence or third CDR comprises a sequence selected from the group consisting of: 23, 47, 48, 56, 61, 65, and 68.

103. The method of embodiments 99 or 100, wherein the protein comprises a first sequence or first CDR comprising a sequence of SEQ ID NO: 19, a second sequence or second CDR comprising a sequence of SEQ ID NO: 21, and a third sequence or third CDR comprising a sequence of SEQ ID NO: 23.

104. The method of embodiments 99 or 100, wherein the nucleotide sequence encodes a light chain that is at least, or about 60, 70, 80, 85, 90, 91, 92, 93, 94, 95, 96, 97, 98, or 99% identical to a protein having a sequence of SEQ ID NO: SEQ ID NO: 2 (F10h). SEQ ID NO: 1 (F10), SEQ ID NO: 3 (B9), SEQ ID NO: 4 (B9h), SEQ ID NO: 5 (N6-G3), SEQ ID NO: 6 (N6-C5), SEQ ID NO: 7 (N6-F11), SEQ ID NO: 8 (N5-B4), or SEQ ID NO: 9 (N5-B7).

105. The method of embodiment 104, wherein the nucleotide sequence encodes a light chain comprising a protein having a sequence of SEQ ID NO: SEQ ID NO: 2 (F10h). SEQ ID NO: 1 (F10), SEQ ID NO: 3 (B9), SEQ ID NO: 4 (B9h), SEQ ID NO: 5 (N6-G3), SEQ ID NO: 6 (N6-C5), SEQ ID NO: 7 (N6-F11), SEQ ID NO: 8 (N5-B4), or SEQ ID NO: 9 (N5-B7).

The subject matter is now described with reference to the following examples. These examples are provided for the purpose of illustration only and the claims should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

EXAMPLES

Example 1: Antibodies Comprising a Common Light Chain can Bind to Different Targets Based on the $V_H$ Peptide Antibodies were generated using the common light chains B9, F10, C11, and H11 paired with 8 different heavy chains. Table 4 illustrates that the although the light chain was the same for 8 different targets, the antibodies were able to bind to the targets. Binding is expressed as Signal:Background for binding to the molecular target of the heavy chain antibody (listed at top of Table 4). Expression is based on binding to cells expressing an Fc-binding protein (the ZZ domain of ProA) (ZZ) on their surface, enabling total antibody to bind and be measured. Detection was using flow cytometry with cells transfected to express the target protein. Background binding S:B is normalized to 1.0, using mock-transfected cells as background. The data in the table below illustrate that the light chains can be used with a variety of heavy chains and the antibody generated from a $V_H$ that can bind to the light chains B9 and F10 will function and bind to the target of interest.

TABLE 4

|  | Heavy Chain Target | | | | | | | |
| --- | --- | --- | --- | --- | --- | --- | --- | --- |
|  | CD151 | IGSF8 | CD63 | CD81 | CD315 | CD147 | PTGER4 | CD59 |
| S:B Binding (B9chicken) | 27.4 | 1.7 | 2.7 | 0.6 | 3.7 | 10.3 | 2.7 | 0.7 |
| S:B Expression (B9chicken) | 9.7 | 12.7 | 11.3 | 10.8 | 12.9 | 17.0 | 4.4 | 11.8 |
| S:B Binding (C11chicken) | 1.4 | 5.5 | 0.8 | 30.9 | 20.5 | 1.4 | 3.3 | 1.4 |
| S:B Expression (C11chicken) | 11.5 | 12.0 | 8.8 | 9.8 | 10.2 | 16.6 | 6.2 | 12.2 |
| S:B Binding (F10chicken) | 25.1 | 1.6 | 5.2 | 0.4 | 6.7 | 5.7 | 2.9 | 14.6 |
| S:B Expression (F10chicken) | 13.7 | 11.9 | 15.5 | 11.1 | 13.2 | 15.5 | 5.2 | 12.2 |
| S:B Binding (D3chicken) | 47.5 | 19.4 | 20.6 | 1.2 | 25.4 |  |  |  |
| S:B Expression (D3chicken) | 6.5 | 3.2 | 3.9 | 1.8 | 7.7 |  |  |  |
| S:B Binding (E1chicken) | 28.8 | 18.1 | 31.8 | 1.5 | 25.1 |  |  |  |
| S:B Expression (E1chicken) | 11.3 | 2.0 | 24.4 | 1.7 | 4.7 |  |  |  |

TABLE 2

| Target | MAb | Yield (ug) | Binding |
| --- | --- | --- | --- |
| Her2 | Trastuzumab | 51.1 | 69,198 |
| Her2 | Trastuzumab w/ F10h cLC | 85.5 | 4,345 |
| Control (-Her2) | Trastuzumab w/ F10h cLC | 85.5 | 361 |
| PD-1 | Pembrolizumab | 253.8 | 117,308 |
| PD-1 | Pembrolizumab w/ F10h cLC | 255.4 | 57,574 |
| Control (-PD-1) | Pembrolizumab w/ F10h cLC | 255.4 | 353 |

In addition to these targets, the F10 common light chain or the F10h common light chain was combined with heavy chains that had been raised against CB1, P2X3, RXFP1, and/or Claudin 6 (CLDN6). The combinations were found to be able to bind to CB1, PX23, RXFP1 and/or Claudin 6, which further demonstrates the versatility of the proteins and embodiments provided herein.

Example 2: Commercially available antibodies can be used with the common lights chains. To demonstrate that the common light chains can be used with other antibodies, we constructed antibodies based on Trastuzumab (binds to Her2) and Pembrolizumab (binds to PD-1) that contained either their native light chain or made with the native light chain and the common light chains provided for herein. As illustrated in Table 2, the antibodies comprising the common light chain of F10 were able to bind to the target even though the light chain was not generated against the targets of Her2 or PD-1. Briefly, two commercial MAbs produced using their native light chain, or produced using the F10h common light chain (SEQ ID NO: 2). Notably, the natural light chains for trastuzumab and pembrolizumab are kappa light chains, while the common light chain F10 is a lambda light chain, which one would have expected to not be able to pair to the heavy chain of the native antibody and retain binding to the target antigen. The data demonstrates that the common light chains, such as F10, can pair across different classes of light chains. Yield represents the ug of the purified MAb resulting from the preparation. Binding represents 66 nM of the indicated MAb binding to HEK-293 cells expressing the target PD1. The Controls represents the same common light chain MAbs staining HEK-293 cells not transfected with the target. Staining was detected by flow cytometry (geometric mean fluorescence).

Example 3: Antibodies comprising a common light chain can bind to the Fc-binding protein (ZZ). 20 different antibodies comprising a common light chain (F10) were tested with their ability to interact with an Fc-binding protein (ZZ) expressed on the surface of QT6 cells. It was found that the antibodies can bind to the QT6 cells expressing the Fc-binding protein (ZZ) and not bind to the parental cell line not expressing the Fc-binding protein (ZZ). The data was measuring using flow cytometry (data not shown). The experiments demonstrated that the common light chains can be used with a variety of heavy chains and the folded antibodies can still be produced from cells at significant levels. The data demonstrates that the common light chain will not interfere with the folding and function of antibodies. This data could not have been predicted and is surprising how versatile the common light chain is.

In summary, the embodiments and examples demonstrate the production and specificity of antibodies with a generic light chain that can be used in different antibodies to bind different targets. This surprising result will enable the generation of additional antibodies with different properties. The present embodiments and examples support a platform by which common light chain molecules (e.g. those described herein, e.g. B9 or F10) can be combined with various heavy chains to yield specific and functional antibodies. This "off the shelf" approach to development of antibodies (i.e. using a generic light chain) allows for more predictable and efficient antibody generation and production. The antibodies comprising the light chains can be used for various methods as provided for herein.

The disclosures of each and every patent, patent application, publication, and accession number cited herein are hereby incorporated herein by reference in their entirety.

While present disclosure has been disclosed with reference to various embodiments, it is apparent that other embodiments and variations of these may be devised by others skilled in the art without departing from the true spirit and scope of the disclosure. The appended claims are intended to be construed to include all such embodiments and equivalent variations.

What is claimed is:

1. A pharmaceutical composition comprising a pharmaceutically acceptable excipient and an antibody light chain variable region comprising a light chain CDR1 (LCDR1), CDR2 (LCDR2), and CDR3 (LCDR3), wherein the light chain variable region comprises:
   an LCDR 1 amino acid sequence of SEQ ID NO: 19; an LCDR2 amino acid sequence of SEQ ID NO: 21; and an LCDR3 amino acid sequence of SEQ ID NO: 23;
   an LCDR 1 amino acid sequence of SEQ ID NO: 52; an LCDR2 amino acid sequence of SEQ ID NO: 54; and an LCDR3 amino acid sequence of SEQ ID NO: 56;
   an LCDR 1 amino acid sequence of SEQ ID NO: 58; an LCDR2 amino acid sequence of SEQ ID NO: 60; and an LCDR3 amino acid sequence of SEQ ID NO: 61;
   an LCDR 1 amino acid sequence of SEQ ID NO: 63; an LCDR2 amino acid sequence of SEQ ID NO: 64; and an LCDR3 amino acid sequence of SEQ ID NO: 65;
   an LCDR 1 amino acid sequence of SEQ ID NO: 66; an LCDR2 amino acid sequence of SEQ ID NO: 67; and an LCDR3 amino acid sequence of SEQ ID NO: 68; or
   an LCDR 1 amino acid sequence of SEQ ID NO: 84; an LCDR2 amino acid sequence of SEQ ID NO: 64; and an LCDR3 amino acid sequence of SEQ ID NO: 73.

2. The pharmaceutical composition of claim 1, wherein the light chain variable region comprises an LCDR1 amino acid sequence of SEQ ID NO: 19; an LCDR2 comprising amino acid sequence of SEQ ID NO: 21; and an LCDR3 amino acid sequence of SEQ ID NO: 23.

3. The pharmaceutical composition of claim 1, wherein the light chain variable region comprises an LCDR1 amino acid sequence of SEQ ID NO: 52; an LCDR2 amino acid sequence of SEQ ID NO: 54; and an LCDR3 amino acid sequence of SEQ ID NO: 56.

4. The pharmaceutical composition of claim 1, wherein the light chain variable region comprises an LCDR1 amino acid sequence of SEQ ID NO: 58; an LCDR2 amino acid sequence of SEQ ID NO: 60; and an LCDR3 amino acid sequence of SEQ ID NO: 61.

5. The pharmaceutical composition of claim 1, wherein the light chain variable region comprises an LCDR1 amino acid sequence of SEQ ID NO: 63; an LCDR2 amino acid sequence of SEQ ID NO: 64; and an LCDR3 amino acid sequence of SEQ ID NO: 65.

6. The pharmaceutical composition of claim 1, wherein the light chain variable region comprises an LCDR1 amino acid sequence of SEQ ID NO: 66; an LCDR2 amino acid sequence of SEQ ID NO: 67; and an LCDR3 amino acid sequence of SEQ ID NO: 68.

7. The pharmaceutical composition of claim 1, wherein the light chain variable region comprises an LCDR1 amino acid sequence of SEQ ID NO: 84; an LCDR2 amino acid sequence of SEQ ID NO: 64; and an LCDR3 amino acid sequence of SEQ ID NO: 73.

8. A nucleic acid encoding an antibody light chain variable region comprising a light chain CDR1 (LCDR1), CDR2 (LCDR2), and CDR3 (LCDR3), wherein the light chain variable region comprises:

an LCDR1 amino acid sequence of SEQ ID NO: 19; an LCDR2 amino acid sequence of SEQ ID NO: 21; and an LCDR3 amino acid sequence of SEQ ID NO: 23;

an LCDR1 amino acid sequence of SEQ ID NO: 52; an LCDR2 amino acid sequence of SEQ ID NO: 54; and an LCDR3 amino acid sequence of SEQ ID NO: 56;

an LCDR1 amino acid sequence of SEQ ID NO: 58; an LCDR2 amino acid sequence of SEQ ID NO: 60; and an LCDR3 amino acid sequence of SEQ ID NO: 61;

an LCDR1 amino acid sequence of SEQ ID NO: 63; an LCDR2 amino acid sequence of SEQ ID NO: 64; and an LCDR3 amino acid sequence of SEQ ID NO: 65;

an LCDR1 amino acid sequence of SEQ ID NO: 66; an LCDR2 amino acid sequence of SEQ ID NO: 67; and an LCDR3 amino acid sequence of SEQ ID NO: 68; or an LCDR1 amino acid sequence of SEQ ID NO: 84; an LCDR2 amino acid sequence of SEQ ID NO: 64; and an LCDR3 amino acid sequence of SEQ ID NO: 73.

9. A cell comprising the nucleic acid molecule of claim 8.

* * * * *

```
                          SEQUENCE LISTING

<160> NUMBER OF SEQ ID NOS: 84

<210> SEQ ID NO 1
<211> LENGTH: 96
<212> TYPE: PRT
<213> ORGANISM: Artificial Sequence
<220> FEATURE:
<223> OTHER INFORMATION: Synthetic sequence

<400> SEQUENCE: 1

Ala Leu Thr Gln Pro Ser Ser Val Ser Ala Asn Pro Gly Glu Thr Val
1               5                   10                  15

Lys Ile Thr Cys Ser Gly Gly Tyr Asn Gly His Tyr Gly Trp Tyr Gln
            20                  25                  30

Gln Lys Ser Pro Gly Ser Ala Pro Val Thr Val Ile Tyr Ser Asn Asn
        35                  40                  45

Gln Arg Pro Ser Asn Ile Pro Ser Arg Phe Ser Gly Ser Thr Ser Gly
    50                  55                  60

Ser Thr Ser Thr Leu Thr Ile Thr Gly Val Arg Ala Glu Asp Glu Ala
65                  70                  75                  80

Val Tyr Phe Cys Gly Gly Tyr Asp Ser Ser Ala Gly Ile Phe Gly Ala
                85                  90                  95

<210> SEQ ID NO 2
<211> LENGTH: 104
<212> TYPE: PRT
<213> ORGANISM: Artificial Sequence
<220> FEATURE:
<223> OTHER INFORMATION: Synthetic sequence

<400> SEQUENCE: 2

Ser Tyr Glu Leu Thr Gln Pro Pro Ser Val Ser Val Ser Pro Gly Gln
1               5                   10                  15

Thr Ala Arg Ile Thr Cys Ser Gly Gly Tyr Asn Gly His Tyr Gly Trp
            20                  25                  30

Tyr Gln Gln Lys Pro Gly Gln Ala Pro Val Leu Val Ile Tyr Ser Asn
        35                  40                  45

Asn Gln Arg Pro Ser Gly Ile Pro Glu Arg Phe Ser Gly Ser Ser Ser
    50                  55                  60

Gly Thr Thr Val Thr Leu Thr Ile Ser Gly Val Gln Ala Glu Asp Glu
65                  70                  75                  80

Ala Asp Tyr Tyr Cys Gly Gly Tyr Asp Ser Ser Ala Gly Ile Phe Gly
                85                  90                  95

Gly Gly Thr Lys Leu Thr Val Leu
            100

<210> SEQ ID NO 3
<211> LENGTH: 106
<212> TYPE: PRT
<213> ORGANISM: Artificial Sequence
<220> FEATURE:
<223> OTHER INFORMATION: Synthetic sequence

<400> SEQUENCE: 3

Ala Leu Thr Gln Pro Ser Ser Val Ser Ala Asn Pro Gly Glu Thr Val
1               5                   10                  15
```

```
Lys Ile Thr Cys Ser Gly Gly Ser Ser Asn Tyr Tyr Gly Trp Tyr
            20                  25                  30

Gln Gln Lys Ser Pro Gly Ser Ala Pro Val Thr Leu Ile Tyr Gly Thr
        35                  40                  45

Asn Lys Arg Pro Ser Asp Ile Pro Ser Arg Phe Ser Gly Ser Lys Ser
50                  55                  60

Gly Ser Thr Gly Thr Leu Thr Ile Thr Gly Val Gln Ala Asp Asp Glu
65                  70                  75                  80

Ala Val Tyr Phe Cys Gly Ser Ala Asp Ser Ser Thr Asn Ala Gly Ile
                85                  90                  95

Phe Gly Ala Gly Thr Thr Leu Thr Val Leu
                100                 105

<210> SEQ ID NO 4
<211> LENGTH: 110
<212> TYPE: PRT
<213> ORGANISM: Artificial Sequence
<220> FEATURE:
<223> OTHER INFORMATION: Synthetic sequence

<400> SEQUENCE: 4

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Ser Asn Tyr Ala Gly
            20                  25                  30

Trp Tyr Gly Tyr Tyr Gln Gln Lys Pro Gly Gln Ala Pro Val Thr Val
        35                  40                  45

Ile Tyr Gly Thr Asn Lys Arg Pro Ser Gly Ile Pro Glu Arg Phe Ser
50                  55                  60

Gly Ser Ser Ser Gly Thr Thr Val Thr Leu Thr Ile Ser Gly Val Gln
65                  70                  75                  80

Ala Glu Asp Glu Ala Val Tyr Tyr Cys Gly Ser Ala Asp Ser Ser Thr
                85                  90                  95

Asn Ala Gly Ile Phe Gly Ala Gly Thr Lys Leu Thr Val Leu
                100                 105                 110

<210> SEQ ID NO 5
<211> LENGTH: 107
<212> TYPE: PRT
<213> ORGANISM: Artificial Sequence
<220> FEATURE:
<223> OTHER INFORMATION: Synthetic sequence

<400> SEQUENCE: 5

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Tyr Tyr
            20                  25                  30

Gly Trp Tyr Gln Gln Lys Pro Gly Gln Ala Pro Val Leu Val Ile Tyr
        35                  40                  45

Gly Thr Asn Lys Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Ser Thr Asp Ser Asn Tyr Val Gly
                85                  90                  95

Ile Phe Gly Gly Gly Thr Lys Leu Thr Val Leu
```

<210> SEQ ID NO 6
<211> LENGTH: 105
<212> TYPE: PRT
<213> ORGANISM: Artificial Sequence
<220> FEATURE:
<223> OTHER INFORMATION: Synthetic sequence

<400> SEQUENCE: 6

Ser Tyr Glu Leu Thr Gln Pro Pro Ser Val Ser Val Ser Pro Gly Gln
1               5                   10                  15

Thr Ala Arg Ile Thr Cys Ser Gly Gly Tyr Asn Gly His Tyr Gly Trp
            20                  25                  30

Tyr Gln Gln Lys Pro Gly Gln Ala Pro Val Leu Val Ile Tyr Ser Asn
        35                  40                  45

Asn Gln Arg Pro Ser Gly Ile Pro Glu Arg Phe Ser Gly Ser Ser Ser
    50                  55                  60

Gly Thr Thr Val Thr Leu Thr Ile Ser Gly Val Gln Ala Glu Asp Glu
65                  70                  75                  80

Ala Asp Tyr Tyr Cys Gly Asn Ala Asp Ser Asn Tyr Val Gly Ile Phe
                85                  90                  95

Gly Gly Gly Thr Lys Leu Thr Val Leu
            100                 105

<210> SEQ ID NO 7
<211> LENGTH: 107
<212> TYPE: PRT
<213> ORGANISM: Artificial Sequence
<220> FEATURE:
<223> OTHER INFORMATION: Synthetic sequence

<400> SEQUENCE: 7

Ser Tyr Glu Leu Thr Gln Pro Pro Ser Val Ser Val Ser Pro Gly Gln
1               5                   10                  15

Thr Ala Arg Ile Thr Cys Ser Gly Gly Gly Ser Ser Asn Tyr Tyr Gly
            20                  25                  30

Trp Tyr Gln Gln Lys Pro Gly Gln Ala Pro Val Leu Val Ile Tyr Ser
        35                  40                  45

Asn Asn Gln Arg Pro Ser Gly Ile Pro Glu Arg Phe Ser Gly Ser Ser
    50                  55                  60

Ser Gly Thr Thr Val Thr Leu Thr Ile Ser Gly Val Gln Ala Glu Asp
65                  70                  75                  80

Glu Ala Asp Tyr Tyr Cys Gly Ser Ala Asp Ser Ser Thr Asn Ala Gly
                85                  90                  95

Ile Phe Gly Gly Gly Thr Lys Leu Thr Val Leu
            100                 105

<210> SEQ ID NO 8
<211> LENGTH: 108
<212> TYPE: PRT
<213> ORGANISM: Artificial Sequence
<220> FEATURE:
<223> OTHER INFORMATION: Synthetic sequence

<400> SEQUENCE: 8

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Gly Ser Tyr Gly Tyr Tyr
            20                  25                  30

```
Gly Trp Tyr Gln Gln Lys Pro Gly Gln Ala Pro Val Leu Val Ile Tyr
            35                  40                  45

Ser Asn Asn Gln Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Ser Ala Asp Ser Ser Thr Asn Ala
                85                  90                  95

Gly Ile Phe Gly Gly Gly Thr Lys Leu Thr Val Leu
            100                 105

<210> SEQ ID NO 9
<211> LENGTH: 108
<212> TYPE: PRT
<213> ORGANISM: Artificial Sequence
<220> FEATURE:
<223> OTHER INFORMATION: Synthetic sequence

<400> SEQUENCE: 9

Ser Tyr Glu Leu Thr Gln Pro Pro Ser Val Ser Val Ser Pro Gly Gln
 1               5                  10                  15

Thr Ala Arg Ile Thr Cys Ser Gly Gly Ser Gly Ser Tyr Gly Tyr Tyr
            20                  25                  30

Gly Trp Tyr Gln Gln Lys Pro Gly Gln Ala Pro Val Leu Val Ile Tyr
            35                  40                  45

Gly Thr Asn Lys Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Ser Ala Asp Ser Ser Thr Asn Ala
                85                  90                  95

Gly Ile Phe Gly Gly Gly Thr Lys Leu Thr Val Leu
            100                 105

<210> SEQ ID NO 10
<211> LENGTH: 123
<212> TYPE: PRT
<213> ORGANISM: Artificial Sequence
<220> FEATURE:
<223> OTHER INFORMATION: Synthetic sequence

<400> SEQUENCE: 10

Ala Val Thr Leu Asp Glu Ser Gly Gly Gly Leu Gln Met Pro Gly Gly
 1               5                  10                  15

Ala Leu Ser Leu Val Cys Lys Ala Ser Gly Phe Thr Phe Ser Ser Tyr
            20                  25                  30

Gly Met Glu Trp Val Arg Gln Ala Pro Gly Lys Gly Leu Glu Trp Val
            35                  40                  45

Ala Gly Ile Ser Ser Gly Gly Ser Thr Asp Tyr Gly Thr Ala Val
            50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Phe Cys
                85                  90                  95

Ala Lys Ser Ala Tyr Gly Gly Thr Trp Asp Gly Asp Asp Ile Asp Ala
            100                 105                 110

Trp Gly His Gly Thr Glu Val Ile Val Ser Ser
```

```
<210> SEQ ID NO 11
<211> LENGTH: 123
<212> TYPE: PRT
<213> ORGANISM: Artificial Sequence
<220> FEATURE:
<223> OTHER INFORMATION: Synthetic sequence

<400> SEQUENCE: 11

Ala Val Thr Leu Asp Glu Ser Gly Gly Leu Gln Thr Pro Gly Gly
1               5                   10                  15

Gly Leu Ser Leu Val Cys Lys Ala Ser Gly Phe Ser Ile Ser Ser Tyr
            20                  25                  30

Glu Met Gln Trp Val Arg Gln Ala Pro Gly Lys Gly Leu Glu Trp Val
        35                  40                  45

Ala Gly Ile Asp Asp Asp Gly Ser Ser Arg Ala Tyr Ala Pro Ala Val
    50                  55                  60

Lys Gly Arg Ala Thr Ile Ser Arg Asp Asn Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Thr Ile Tyr Ala Ala Thr Leu Asn Ala Gly Glu Ile Asp Ala
            100                 105                 110

Trp Gly His Gly Thr Glu Val Ile Val Ser Ser
            115                 120

<210> SEQ ID NO 12
<211> LENGTH: 128
<212> TYPE: PRT
<213> ORGANISM: Artificial Sequence
<220> FEATURE:
<223> OTHER INFORMATION: Synthetic sequence

<400> SEQUENCE: 12

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Asp Arg
            20                  25                  30

Gly Met His Trp Val Arg Gln Ala Pro Gly Lys Gly Leu Glu Trp Val
        35                  40                  45

Ala Gly Ile Arg Ser Thr Gly Ser Phe Thr Leu Tyr Gly Ala Ala Val
    50                  55                  60

Lys Gly Arg Ala Thr Ile Ser Arg Asp Asp Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Ala Lys Ser Ala Gly Gly Tyr Gly Cys Gly Arg Gly Trp Cys Gly Val
            100                 105                 110

Asp Asp Ile Asp Ala Trp Gly His Gly Thr Glu Val Ile Val Ser Ser
            115                 120                 125

<210> SEQ ID NO 13
<211> LENGTH: 124
<212> TYPE: PRT
<213> ORGANISM: Artificial Sequence
<220> FEATURE:
<223> OTHER INFORMATION: Synthetic sequence

<400> SEQUENCE: 13
```

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Arg Asn Tyr
            20                  25                  30

Ile Met Gln Trp Val Arg Gln Ala Pro Gly Lys Glu Leu Glu Trp Val
        35                  40                  45

Ala Gly Ile Ser Thr Ser Gly Arg Thr Tyr Tyr Gly Thr Ala Val Lys
    50                  55                  60

Gly Arg Ala Thr Ile Ser Arg Asp Thr Gly Gln Ser Thr Val Arg Leu
65                  70                  75                  80

Gln Leu Asn Asn Leu Arg Ala Glu Asp Thr Gly Thr Tyr Phe Cys Ala
                85                  90                  95

Lys Tyr Gly Ser Gly Val Ser Tyr Ser Tyr Asn Ala Gly Gln Ile Asp
            100                 105                 110

Ala Trp Gly His Gly Thr Glu Val Ile Val Ser Ser
        115                 120

<210> SEQ ID NO 14
<211> LENGTH: 123
<212> TYPE: PRT
<213> ORGANISM: Artificial Sequence
<220> FEATURE:
<223> OTHER INFORMATION: Synthetic sequence

<400> SEQUENCE: 14

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Tyr
            20                  25                  30

Ala Met Tyr Trp Val Arg Gln Ala Pro Gly Lys Gly Leu Gln Trp Val
        35                  40                  45

Ala Gly Ile Ser Arg Asp Gly Ser Ser Gly Arg Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Phe Cys
                85                  90                  95

Ala Lys Ser Gly Tyr Gly Asp Tyr Thr Ser Ala Asp Glu Ile Asp Ala
            100                 105                 110

Trp Gly His Gly Thr Glu Val Ile Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: Synthetic sequence

<400> SEQUENCE: 15

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Asp Phe Ser Ser Phe
            20                  25                  30

Asp Met Val Trp Val Arg Gln Ala Pro Gly Lys Gly Leu Glu Trp Val
        35                  40                  45

Ala Gly Ile Ser Tyr Ser Asn Thr Asp Thr Ser Tyr Ala Pro Ala Val

```
                50                  55                  60
Asp Gly Arg Ala Thr Ile Ser Arg Asp Asn Gly Gln Ser Thr Val Arg
 65                  70                  75                  80

Leu Gln Leu Asn Asn Leu Arg Ala Glu Asp Ser Ala Thr Tyr Tyr Cys
                 85                  90                  95

Ala Lys Ser Ala Gly Gly Cys Cys Tyr Arg Ala Asp Asn Ile Asp Ala
                100                 105                 110

Trp Gly His Gly Thr Glu Val Ile Val Ser Ser
            115                 120

<210> SEQ ID NO 16
<211> LENGTH: 123
<212> TYPE: PRT
<213> ORGANISM: Artificial Sequence
<220> FEATURE:
<223> OTHER INFORMATION: Synthetic sequence

<400> SEQUENCE: 16

Ala Val Thr Leu Asp Glu Ser Gly Gly Gly Leu Gln Thr Pro Gly Gly
 1               5                  10                  15

Ala Leu Ser Leu Val Cys Lys Ala Ser Gly Phe Ser Ile Gly Asp Tyr
                 20                  25                  30

Asn Met Gly Trp Val Arg Gln Ala Pro Gly Lys Gly Leu Glu Trp Val
             35                  40                  45

Ala Gly Ile Asp Ala Gly Gly Thr Trp Arg Ala Thr Ala Val Lys
 50                  55                  60

Gly Arg Ala Thr Ile Ser Arg Asp Asn Gly Gln Ser Thr Val Arg Leu
 65                  70                  75                  80

Gln Leu Asn Asn Leu Arg Ala Glu Asp Thr Ala Thr Tyr Phe Cys Ala
                 85                  90                  95

Lys Ser Thr Asp Ser Ser Ala Asn Cys Cys Ala Asn Ser Ile Asp Ala
                100                 105                 110

Trp Gly His Gly Thr Glu Val Ile Val Ser Ser
            115                 120

<210> SEQ ID NO 17
<211> LENGTH: 124
<212> TYPE: PRT
<213> ORGANISM: Artificial Sequence
<220> FEATURE:
<223> OTHER INFORMATION: Synthetic sequence

<400> SEQUENCE: 17

Ala Val Thr Leu Asp Glu Ser Gly Gly Gly Leu Gln Thr Pro Gly Gly
 1               5                  10                  15

Gly Leu Ser Leu Val Cys Lys Ala Ser Gly Phe Thr Ser Ser Asn Tyr
                 20                  25                  30

Ile Met Gln Trp Val Arg Gln Ala Pro Gly Lys Gly Leu Asp Trp Val
             35                  40                  45

Ala Gly Ile Ser Thr Ser Gly Arg Thr Tyr Tyr Gly Thr Ala Val Lys
 50                  55                  60

Gly Arg Ala Thr Ile Ser Arg Asp Asn Gly Gln Ser Thr Val Arg Leu
 65                  70                  75                  80

Gln Leu Ser Asn Leu Arg Ala Glu Asp Thr Gly Ile Tyr Phe Cys Ala
                 85                  90                  95

Lys Phe Gly Ser Gly Val Ser Thr Tyr Asn Ala Gly Gln Ile Asp
                100                 105                 110
```

```
Ala Trp Gly His Gly Thr Glu Val Ile Val Ser Ser
        115                 120

<210> SEQ ID NO 18
<211> LENGTH: 20
<212> TYPE: PRT
<213> ORGANISM: Artificial Sequence
<220> FEATURE:
<223> OTHER INFORMATION: Synthetic sequence

<400> SEQUENCE: 18

Ala Leu Thr Gln Pro Ser Ser Val Ser Ala Asn Pro Gly Glu Thr Val
1               5                   10                  15

Lys Ile Thr Cys
            20

<210> SEQ ID NO 19
<211> LENGTH: 9
<212> TYPE: PRT
<213> ORGANISM: Artificial Sequence
<220> FEATURE:
<223> OTHER INFORMATION: Synthetic sequence

<400> SEQUENCE: 19

Ser Gly Gly Tyr Asn Gly His Tyr Gly
1               5

<210> SEQ ID NO 20
<211> LENGTH: 16
<212> TYPE: PRT
<213> ORGANISM: Artificial Sequence
<220> FEATURE:
<223> OTHER INFORMATION: Synthetic sequence

<400> SEQUENCE: 20

Trp Tyr Gln Gln Lys Ser Pro Gly Ser Ala Pro Val Thr Val Ile Tyr
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic sequence

<400> SEQUENCE: 21

Ser Asn Asn Gln Arg Pro Ser
1               5

<210> SEQ ID NO 22
<211> LENGTH: 32
<212> TYPE: PRT
<213> ORGANISM: Artificial Sequence
<220> FEATURE:
<223> OTHER INFORMATION: Synthetic sequence

<400> SEQUENCE: 22

Asn Ile Pro Ser Arg Phe Ser Gly Ser Thr Ser Gly Ser Thr Ser Thr
1               5                   10                  15

Leu Thr Ile Thr Gly Val Arg Ala Glu Asp Glu Ala Val Tyr Phe Cys
            20                  25                  30

<210> SEQ ID NO 23
<211> LENGTH: 9
<212> TYPE: PRT
<213> ORGANISM: Artificial Sequence
```

```
<220> FEATURE:
<223> OTHER INFORMATION: Synthetic sequence

<400> SEQUENCE: 23

Gly Gly Tyr Asp Ser Ser Ala Gly Ile
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic sequence

<400> SEQUENCE: 24

Phe Gly Ala Gly Thr Thr Leu Thr Val Leu
1               5                   10

<210> SEQ ID NO 25
<211> LENGTH: 22
<212> TYPE: PRT
<213> ORGANISM: Artificial Sequence
<220> FEATURE:
<223> OTHER INFORMATION: Synthetic sequence

<400> SEQUENCE: 25

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 26
<211> LENGTH: 15
<212> TYPE: PRT
<213> ORGANISM: Artificial Sequence
<220> FEATURE:
<223> OTHER INFORMATION: Synthetic sequence

<400> SEQUENCE: 26

Trp Tyr Gln Gln Lys Pro Gly Gln Ala Pro Val Leu Val Ile Tyr
1               5                   10                  15

<210> SEQ ID NO 27
<211> LENGTH: 32
<212> TYPE: PRT
<213> ORGANISM: Artificial Sequence
<220> FEATURE:
<223> OTHER INFORMATION: Synthetic sequence

<400> SEQUENCE: 27

Gly Ile Pro Glu Arg Phe Ser Gly Ser Ser Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 28

<400> SEQUENCE: 28

000

<210> SEQ ID NO 29
<211> LENGTH: 10
<212> TYPE: PRT
<213> ORGANISM: Artificial Sequence
<220> FEATURE:
```

<223> OTHER INFORMATION: Synthetic sequence

<400> SEQUENCE: 29

Phe Gly Gly Gly Thr Lys Leu Thr Val Leu
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic sequence

<400> SEQUENCE: 30

Trp Tyr Gln Gln Lys Pro Gly Gln Ala Pro Val Thr Val Ile Tyr
1               5                   10                  15

<210> SEQ ID NO 31
<211> LENGTH: 22
<212> TYPE: PRT
<213> ORGANISM: Artificial Sequence
<220> FEATURE:
<223> OTHER INFORMATION: Synthetic sequence

<400> SEQUENCE: 31

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: Synthetic sequence

<400> SEQUENCE: 32

Trp Tyr Gln Gln Lys Pro Gly Gln Ser Pro Val Leu Val Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Synthetic sequence

<400> SEQUENCE: 33

Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30

<210> SEQ ID NO 34
<211> LENGTH: 10
<212> TYPE: PRT
<213> ORGANISM: Artificial Sequence
<220> FEATURE:
<223> OTHER INFORMATION: Synthetic sequence

<400> SEQUENCE: 34

Thr Gly Thr Gly Thr Lys Leu Thr Val Leu
1               5                   10

```
<210> SEQ ID NO 35
<211> LENGTH: 15
<212> TYPE: PRT
<213> ORGANISM: Artificial Sequence
<220> FEATURE:
<223> OTHER INFORMATION: Synthetic sequence

<400> SEQUENCE: 35

Trp Tyr Gln Gln Lys Pro Gly Gln Ser Pro Val Thr Val Ile Tyr
1               5                   10                  15

<210> SEQ ID NO 36
<211> LENGTH: 22
<212> TYPE: PRT
<213> ORGANISM: Artificial Sequence
<220> FEATURE:
<223> OTHER INFORMATION: Synthetic sequence

<400> SEQUENCE: 36

Ser Tyr Glu Leu Thr Gln Pro Pro Ser Val Ser Val Ala Pro Gly Lys
1               5                   10                  15

Thr Ala Arg Ile Thr Cys
            20

<210> SEQ ID NO 37
<211> LENGTH: 32
<212> TYPE: PRT
<213> ORGANISM: Artificial Sequence
<220> FEATURE:
<223> OTHER INFORMATION: Synthetic sequence

<400> SEQUENCE: 37

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 38
<211> LENGTH: 22
<212> TYPE: PRT
<213> ORGANISM: Artificial Sequence
<220> FEATURE:
<223> OTHER INFORMATION: Synthetic sequence

<400> SEQUENCE: 38

Ser Tyr Glu Leu Thr Gln Asp Pro Ala Val Ser Val Ala Leu Gly Gln
1               5                   10                  15

Thr Val Arg Ile Thr Cys
            20

<210> SEQ ID NO 39
<211> LENGTH: 32
<212> TYPE: PRT
<213> ORGANISM: Artificial Sequence
<220> FEATURE:
<223> OTHER INFORMATION: Synthetic sequence

<400> SEQUENCE: 39

Asn Ile Pro Asp Arg Phe Ser Gly Ser Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 40
<211> LENGTH: 10
```

```
<212> TYPE: PRT
<213> ORGANISM: Artificial Sequence
<220> FEATURE:
<223> OTHER INFORMATION: Synthetic sequence

<400> SEQUENCE: 40

Phe Gly Ser Gly Thr Lys Leu Thr Val Leu
1               5                   10

<210> SEQ ID NO 41
<211> LENGTH: 32
<212> TYPE: PRT
<213> ORGANISM: Artificial Sequence
<220> FEATURE:
<223> OTHER INFORMATION: Synthetic sequence

<400> SEQUENCE: 41

Asn Ile Pro Glu Arg Phe Ser Gly Ser Thr Ser Gly Ser Thr Ser Thr
1               5                   10                  15

Leu Thr Ile Ser Gly Val Gln Ala Glu Asp Glu Ala Asp Tyr Tyr Cys
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic sequence

<400> SEQUENCE: 42

Asn Ile Pro Asp Arg Phe Ser Gly Ser Thr Ser Gly Ser Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 43
<211> LENGTH: 10
<212> TYPE: PRT
<213> ORGANISM: Artificial Sequence
<220> FEATURE:
<223> OTHER INFORMATION: Synthetic sequence

<400> SEQUENCE: 43

Phe Gly Ser Gly Thr Lys Val Thr Val Leu
1               5                   10

<210> SEQ ID NO 44
<211> LENGTH: 32
<212> TYPE: PRT
<213> ORGANISM: Artificial Sequence
<220> FEATURE:
<223> OTHER INFORMATION: Synthetic sequence

<400> SEQUENCE: 44

Asn Ile Pro Glu Arg Phe Ser Gly Ser Thr Ser Gly Ser Thr Ser Thr
1               5                   10                  15

Leu Thr Ile Ser Gly Thr Gln Ala Met Asp Glu Ala Asp Tyr Tyr Cys
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: Synthetic sequence
```

```
<400> SEQUENCE: 45

Asn Ile Pro Glu Arg Phe Ser Gly Ser Thr Ser Gly Ser Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 46
<211> LENGTH: 22
<212> TYPE: PRT
<213> ORGANISM: Artificial Sequence
<220> FEATURE:
<223> OTHER INFORMATION: Synthetic sequence

<400> SEQUENCE: 46

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 47
<211> LENGTH: 10
<212> TYPE: PRT
<213> ORGANISM: Artificial Sequence
<220> FEATURE:
<223> OTHER INFORMATION: Synthetic sequence

<400> SEQUENCE: 47

Gly Asn Ala Asp Ser Asn Tyr Val Gly Ile
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic sequence

<400> SEQUENCE: 48

Gly Ser Thr Asp Ser Asn Tyr Val Gly Ile
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic sequence

<400> SEQUENCE: 49

Gly Gly Asn Asn Ile Gly Ser Lys Ser Val His
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic sequence

<400> SEQUENCE: 50

Ser Gly Asp Ala Leu Pro Lys Gln Tyr Ala Tyr
1               5                   10

<210> SEQ ID NO 51
<211> LENGTH: 11
```

```
<212> TYPE: PRT
<213> ORGANISM: Artificial Sequence
<220> FEATURE:
<223> OTHER INFORMATION: Synthetic sequence

<400> SEQUENCE: 51

Ser Gly Asp Ser Ser Tyr Tyr Gly Tyr Tyr Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic sequence

<400> SEQUENCE: 52

Ser Gly Gly Gly Ser Ser Asn Tyr Tyr Gly
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Synthetic sequence

<400> SEQUENCE: 53

Trp Tyr Gln Gln Lys Ser Pro Gly Ser Ala Pro Val Thr Leu Ile Tyr
1               5                   10                  15

<210> SEQ ID NO 54
<211> LENGTH: 7
<212> TYPE: PRT
<213> ORGANISM: Artificial Sequence
<220> FEATURE:
<223> OTHER INFORMATION: Synthetic sequence

<400> SEQUENCE: 54

Gly Thr Asn Lys Arg Pro Ser
1               5

<210> SEQ ID NO 55
<211> LENGTH: 32
<212> TYPE: PRT
<213> ORGANISM: Artificial Sequence
<220> FEATURE:
<223> OTHER INFORMATION: Synthetic sequence

<400> SEQUENCE: 55

Asp Ile Pro Ser Arg Phe Ser Gly Ser Lys Ser Gly Ser Thr Gly Thr
1               5                   10                  15

Leu Thr Ile Thr Gly Val Gln Ala Asp Asp Glu Ala Val Tyr Phe Cys
            20                  25                  30

<210> SEQ ID NO 56
<211> LENGTH: 11
<212> TYPE: PRT
<213> ORGANISM: Artificial Sequence
<220> FEATURE:
<223> OTHER INFORMATION: Synthetic sequence

<400> SEQUENCE: 56

Gly Ser Ala Asp Ser Ser Thr Asn Ala Gly Ile
1               5                   10
```

```
<210> SEQ ID NO 57
<211> LENGTH: 11
<212> TYPE: PRT
<213> ORGANISM: Artificial Sequence
<220> FEATURE:
<223> OTHER INFORMATION: Synthetic sequence

<400> SEQUENCE: 57

Ser Gly Asp Ala Leu Pro Lys Gln Tyr Ala Tyr
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Synthetic sequence

<400> SEQUENCE: 58

Ser Gly Gly Gly Ser Trp Tyr Gly Ser Tyr Tyr Tyr Gly
1               5                   10

<210> SEQ ID NO 59
<211> LENGTH: 32
<212> TYPE: PRT
<213> ORGANISM: Artificial Sequence
<220> FEATURE:
<223> OTHER INFORMATION: Synthetic sequence

<400> SEQUENCE: 59

Asp Ile Pro Ser Arg Phe Ser Gly Ser Glu Ser Gly Ser Thr Ala Thr
1               5                   10                  15

Leu Thr Ile Thr Gly Val Gln Ala Glu Asp Glu Ala Val Tyr Phe Cys
            20                  25                  30

<210> SEQ ID NO 60
<211> LENGTH: 7
<212> TYPE: PRT
<213> ORGANISM: Artificial Sequence
<220> FEATURE:
<223> OTHER INFORMATION: Synthetic sequence

<400> SEQUENCE: 60

Asn Asn Asp Lys Arg Pro Ser
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic sequence

<400> SEQUENCE: 61

Gly Gly Tyr Asp Ser Thr Thr Thr Asp Met
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic sequence

<400> SEQUENCE: 62

Ser Gly Gly Gly Ser Ser Asn Tyr Tyr Gly Gly
1               5                   10
```

<210> SEQ ID NO 63
<211> LENGTH: 8
<212> TYPE: PRT
<213> ORGANISM: Artificial Sequence
<220> FEATURE:
<223> OTHER INFORMATION: Synthetic sequence

<400> SEQUENCE: 63

Ser Gly Asp Asp Arg Trp Tyr Gly
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic sequence

<400> SEQUENCE: 64

Ser Asn Asp Lys Arg Pro Ser
1               5

<210> SEQ ID NO 65
<211> LENGTH: 10
<212> TYPE: PRT
<213> ORGANISM: Artificial Sequence
<220> FEATURE:
<223> OTHER INFORMATION: Synthetic sequence

<400> SEQUENCE: 65

Gly Ser Arg Asp Ser Ser Tyr Ala Gly Ile
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic sequence

<400> SEQUENCE: 66

Ser Gly Ser Ser Gly Ser Gly Tyr Tyr Gly
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic sequence

<400> SEQUENCE: 67

Asp Asn Asp Lys Arg Pro Ser
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic sequence

<400> SEQUENCE: 68

Gly Ser Ala Asp Asn Asn Tyr Thr Gly Ile
1               5                   10

<210> SEQ ID NO 69
<211> LENGTH: 4
<212> TYPE: PRT
<213> ORGANISM: Artificial Sequence
<220> FEATURE:
<223> OTHER INFORMATION: Synthetic sequence

<400> SEQUENCE: 69

Tyr Tyr Gly Gly
1

<210> SEQ ID NO 70
<211> LENGTH: 11
<212> TYPE: PRT
<213> ORGANISM: Artificial Sequence
<220> FEATURE:
<223> OTHER INFORMATION: Synthetic sequence

<400> SEQUENCE: 70

Ser Gly Gly Ser Gly Ser Tyr Gly Tyr Tyr Gly
1               5                   10

<210> SEQ ID NO 71
<211> LENGTH: 8
<212> TYPE: PRT
<213> ORGANISM: Artificial Sequence
<220> FEATURE:
<223> OTHER INFORMATION: Synthetic sequence

<400> SEQUENCE: 71

Ser Gly Asp Ser Ser Tyr Tyr Gly
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic sequence

<400> SEQUENCE: 72

Asp Asn Thr Asn Arg Pro Ser
1               5

<210> SEQ ID NO 73
<211> LENGTH: 11
<212> TYPE: PRT
<213> ORGANISM: Artificial Sequence
<220> FEATURE:
<223> OTHER INFORMATION: Synthetic sequence

<400> SEQUENCE: 73

Gly Ser Ala Asp Ser Ser Ser Thr Ala Gly Ile
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic sequence

<400> SEQUENCE: 74

Ser Gly Gly Tyr Asn Gly His Tyr Gly Tyr Gly
1               5                   10

```
<210> SEQ ID NO 75
<211> LENGTH: 11
<212> TYPE: PRT
<213> ORGANISM: Artificial Sequence
<220> FEATURE:
<223> OTHER INFORMATION: Synthetic sequence

<400> SEQUENCE: 75

Ser Gly Gly Gly Ser Trp Tyr Gly Ser Tyr Gly
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic sequence

<400> SEQUENCE: 76

Ser Gly Asp Asp Arg Trp Tyr Gly Tyr Tyr Gly
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Synthetic sequence

<400> SEQUENCE: 77

Tyr Asp Ser Asp Arg Pro Ser
1               5

<210> SEQ ID NO 78
<211> LENGTH: 11
<212> TYPE: PRT
<213> ORGANISM: Artificial Sequence
<220> FEATURE:
<223> OTHER INFORMATION: Synthetic sequence

<400> SEQUENCE: 78

Gln Val Trp Asp Ser Ser Ser Asp His Val Val
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Synthetic sequence

<400> SEQUENCE: 79

Lys Asp Ser Glu Arg Pro Ser
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic sequence

<400> SEQUENCE: 80

Gln Ser Ala Asp Ser Ser Gly Thr Tyr Val
1               5                   10

<210> SEQ ID NO 81
```

```
<211> LENGTH: 18
<212> TYPE: PRT
<213> ORGANISM: Artificial Sequence
<220> FEATURE:
<223> OTHER INFORMATION: Synthetic sequence

<400> SEQUENCE: 81

Gly Gln Ser Ser Arg Ser Ser Gly Gly Gly Gly Ser Ser Gly Gly Gly
1               5                   10                  15
Gly Ser

<210> SEQ ID NO 82
<211> LENGTH: 5
<212> TYPE: PRT
<213> ORGANISM: Artificial Sequence
<220> FEATURE:
<223> OTHER INFORMATION: Synthetic sequence

<400> SEQUENCE: 82

Gly Gly Gly Gly Ser
1               5

<210> SEQ ID NO 83
<211> LENGTH: 5
<212> TYPE: PRT
<213> ORGANISM: Artificial Sequence
<220> FEATURE:
<223> OTHER INFORMATION: Synthetic sequence

<400> SEQUENCE: 83

Gly Gly Gly Gly Ala
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic sequence

<400> SEQUENCE: 84

Ser Gly Gly Ser Gly Ser Tyr Gly
1               5
```